US012297496B2

(12) United States Patent
Webster

(10) Patent No.: US 12,297,496 B2
(45) Date of Patent: May 13, 2025

(54) INTEGRATED CIRCUIT WITH IMPROVED CHARGE TRANSFER EFFICIENCY AND ASSOCIATED TECHNIQUES

(71) Applicant: Quantum-Si Incorporated, Guilford, CT (US)

(72) Inventor: Eric A. G. Webster, Santa Clara, CA (US)

(73) Assignee: Quantum-Si Incorporated, Branford, CT (US)

( * ) Notice: Subject to any disclaimer, the term of this patent is extended or adjusted under 35 U.S.C. 154(b) by 404 days.

(21) Appl. No.: 17/548,428

(22) Filed: Dec. 10, 2021

(65) Prior Publication Data

US 2022/0190012 A1    Jun. 16, 2022

Related U.S. Application Data

(60) Provisional application No. 63/124,655, filed on Dec. 11, 2020.

(51) Int. Cl.
*C12Q 1/6869*    (2018.01)
*G01N 21/64*    (2006.01)
(Continued)

(52) U.S. Cl.
CPC ....... *C12Q 1/6869* (2013.01); *G01N 21/6408* (2013.01); *G01N 21/6428* (2013.01);
(Continued)

(58) Field of Classification Search
CPC ............. C12Q 1/6869; G01N 21/6408; G01N 21/6428; G01N 21/6458;
(Continued)

(56) References Cited

U.S. PATENT DOCUMENTS 4,801,987 A  *  1/1989  Otsubo ................. H01L 29/808
                                                         257/260
5,961,924 A    10/1999  Reichert et al.
(Continued)

FOREIGN PATENT DOCUMENTS

EP            3 483 938 A1    5/2019
WO    WO 2011/153962 A1    12/2011

OTHER PUBLICATIONS

U.S. Appl. No. 17/548,408, filed Dec. 10, 2021, Webster.
(Continued)

*Primary Examiner* — Kevin K Pyo
*Assistant Examiner* — Don J Williams
(74) *Attorney, Agent, or Firm* — Wolf, Greenfield & Sacks, P.C.

(57) ABSTRACT

The present disclosure provides techniques for improving the rate and efficiency of charge transfer within an integrated circuit configured to receive incident photons. Some aspects of the present disclosure relate to integrated circuits that are configured to induce one or more intrinsic electric fields that increase the rate and efficiency of charge transfer within the integrated circuits. Some aspects of the present disclosure relate to integrated circuits configured to induce a charge carrier depletion in the photodetection region(s) of the integrated circuits. In some embodiments, the charge carrier depletion in the photodetection region(s) may be intrinsic, in that the depletion is induced even in the absence of external electric fields applied to the integrated circuit. Some aspects of the present disclosure relate to processes for operating and/or manufacturing integrated devices as described herein.

21 Claims, 53 Drawing Sheets

(51) Int. Cl.
*H01L 27/146* (2006.01)
*H01L 27/148* (2006.01)
*H01S 3/1112* (2023.01)

(52) U.S. Cl.
CPC ... *G01N 21/6458* (2013.01); *H01L 27/14609* (2013.01); *H01L 27/14806* (2013.01); *H01L 27/14818* (2013.01); *H01S 3/1112* (2013.01); *G01N 2201/06113* (2013.01); *G01N 2201/0697* (2013.01)

(58) Field of Classification Search
CPC .. G01N 2201/06113; G01N 2201/0697; H01L 27/14609; H01L 27/14806; H01L 27/14818; H01S 3/1112
See application file for complete search history.

(56) References Cited

U.S. PATENT DOCUMENTS

| | | |
|---|---|---|
| 6,787,308 B2 | 9/2004 | Balasubramanian et al. |
| 6,917,726 B2 | 7/2005 | Levene et al. |
| 7,175,811 B2 | 2/2007 | Bach et al. |
| 7,426,322 B2 | 9/2008 | Hyde |
| 7,738,086 B2 | 6/2010 | Shepard et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 8,053,742 B2 | 11/2011 | Lundquist et al. |
| 8,207,509 B2 | 6/2012 | Lundquist et al. |
| 8,274,040 B2 | 9/2012 | Zhong et al. |
| 8,278,728 B2 | 10/2012 | Murshid |
| 8,465,699 B2 | 6/2013 | Fehr et al. |
| 8,471,219 B2 | 6/2013 | Lundquist et al. |
| 8,471,230 B2 | 6/2013 | Zhong et al. |
| 8,502,169 B2 | 8/2013 | Rigneault et al. |
| 8,618,507 B1 | 12/2013 | Lundquist et al. |
| 8,723,284 B1* | 5/2014 | Hynecek ............... H01L 31/103 257/292 |
| 9,029,802 B2 | 5/2015 | Lundquist et al. |
| 9,157,864 B2 | 10/2015 | Fehr et al. |
| 9,222,123 B2 | 12/2015 | Zhong et al. |
| 9,222,133 B2 | 12/2015 | Lundquist et al. |
| 9,223,084 B2 | 12/2015 | Grot et al. |
| 9,372,308 B1 | 6/2016 | Saxena et al. |
| 9,587,276 B2 | 3/2017 | Lundquist et al. |
| 9,606,060 B2 | 3/2017 | Chen et al. |
| 9,658,161 B2 | 5/2017 | Saxena et al. |
| 9,666,748 B2 | 5/2017 | Leobandung |
| 9,719,138 B2 | 8/2017 | Zhong et al. |
| 9,765,395 B2 | 9/2017 | Goldsmith |
| 9,946,017 B2 | 4/2018 | Saxena et al. |
| 10,018,764 B2 | 7/2018 | Grot et al. |
| 10,090,429 B2 | 10/2018 | Leobandung |
| 10,138,515 B2 | 11/2018 | Fehr et al. |
| 10,280,457 B2 | 5/2019 | Zhong et al. |
| 10,310,178 B2 | 6/2019 | Saxena et al. |
| 10,487,356 B2 | 11/2019 | Lundquist et al. |
| 10,578,788 B2 | 3/2020 | Grot et al. |
| 10,655,172 B2 | 5/2020 | Rank et al. |
| 10,724,090 B2 | 7/2020 | McCaffrey et al. |
| 2002/0182716 A1 | 12/2002 | Weisbuch et al. |
| 2003/0174992 A1 | 9/2003 | Levene et al. |
| 2009/0114919 A1 | 5/2009 | Kawahito et al. |
| 2010/0065726 A1 | 3/2010 | Zhong et al. |
| 2011/0101241 A1 | 5/2011 | Cottier et al. |
| 2011/0121423 A1 | 5/2011 | Forsyth et al. |
| 2012/0273654 A1 | 11/2012 | Hynecek et al. |
| 2013/0070131 A1 | 3/2013 | Ohkubo et al. |
| 2013/0116153 A1 | 5/2013 | Bowen et al. |
| 2015/0069217 A1* | 3/2015 | Taylor ............... H01L 27/14652 257/14 |
| 2017/0146479 A1 | 5/2017 | Levine et al. |
| 2017/0244921 A1 | 8/2017 | Velichko |
| 2017/0322153 A1 | 11/2017 | Rothberg et al. |
| 2018/0180546 A1 | 6/2018 | Rothberg et al. |
| 2019/0292590 A1 | 9/2019 | Zhong et al. |
| 2019/0391010 A1 | 12/2019 | Thurston et al. |
| 2020/0408690 A1 | 12/2020 | Yang et al. |
| 2021/0025823 A1 | 1/2021 | Rothberg et al. |
| 2021/0025824 A1 | 1/2021 | Rothberg et al. |
| 2021/0215605 A1 | 7/2021 | Schmid et al. |
| 2021/0217800 A1 | 7/2021 | Webster et al. |
| 2022/0128402 A1 | 4/2022 | Webster et al. |
| 2022/0128403 A1 | 4/2022 | Webster et al. |
| 2022/0186305 A1 | 6/2022 | Webster |

OTHER PUBLICATIONS

PCT/US2021/062929, Feb. 4, 2022, Invitation to Pay Additional Fees.
PCT/US2021/062929, Mar. 30, 2022, International Search Report and Written Opinion.
International Search Report and Written Opinion for International Application No. PCT/US2021/062929 mailed Mar. 30, 2022.
Invitation to Pay Additional Fees for International Application No. PCT/US2021/062929 mailed Feb. 4, 2022.
Hale, Fibre Optic Sensors using Adiabatically Tapered Single Mode Fibres. Dissertation submitted to the University of Cambridge. Feb. 1994. 209 pages.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Taitt et al., Evanescent wave fluorescence biosensors. Biosens Bioelectron. Jun. 2005;20(12):2470-87. Epub Dec. 8, 2004.
International Preliminary Report on Patentability for International Application No. PCT/US2021/062929 mailed Jun. 22, 2023.
Extended European Search Report dated Feb. 26, 2025, in connection with European Application No. 21904516.

\* cited by examiner

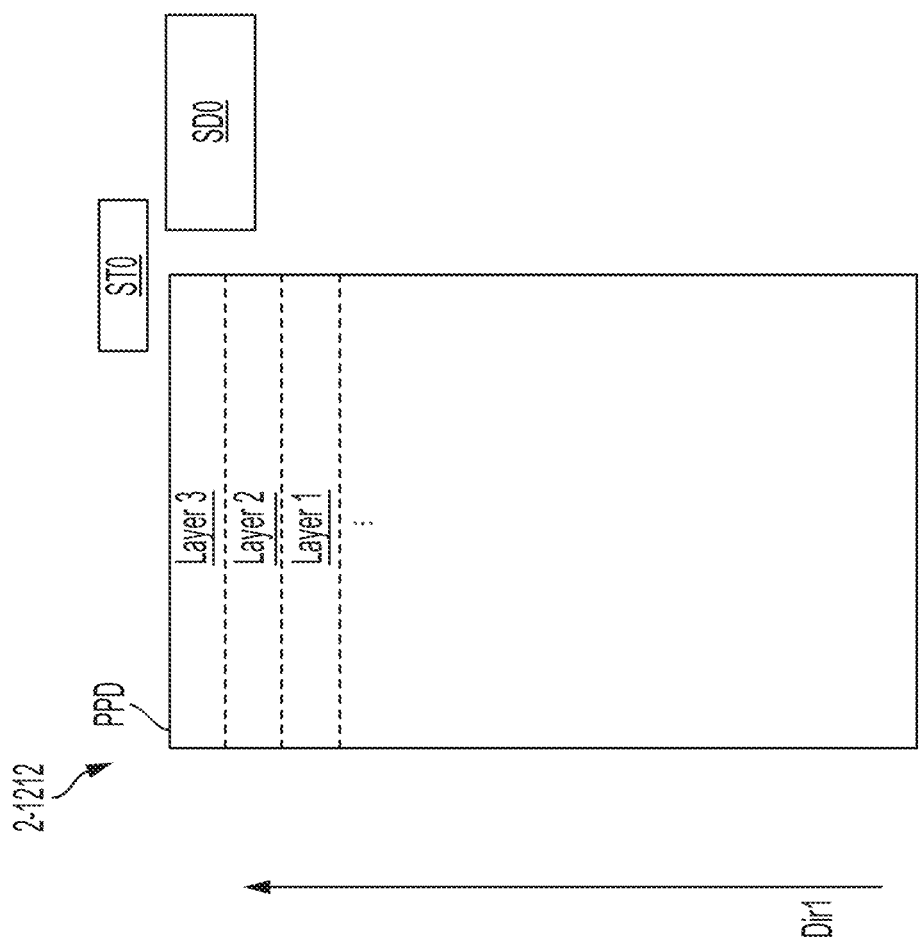

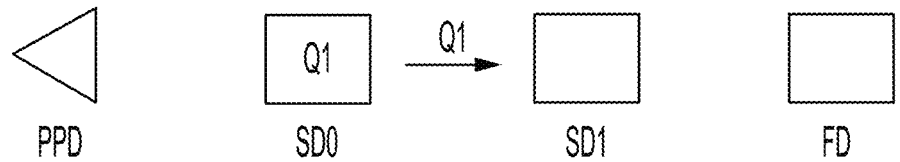
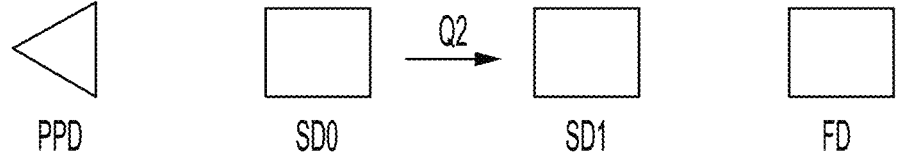
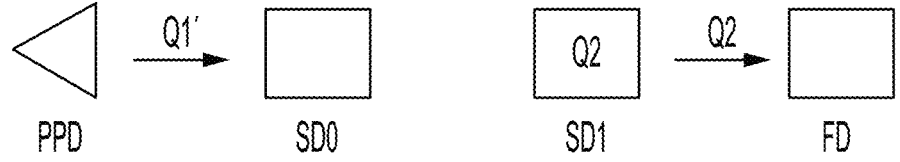
FIG. 2-14

INTEGRATED CIRCUIT WITH IMPROVED CHARGE TRANSFER EFFICIENCY AND ASSOCIATED TECHNIQUES

RELATED APPLICATIONS

This application claims priority under 35 U.S.C. § 119(e) to U.S. Provisional Application Ser. No. 63/124,655, filed Dec. 11, 2020, and titled, "INTEGRATED CIRCUIT WITH IMPROVED CHARGE TRANSFER EFFICIENCY AND ASSOCIATED TECHNIQUES," which is herein incorporated by reference in its entirety.

FIELD OF THE DISCLOSURE

The present disclosure relates to integrated devices and related instruments that can perform massively-parallel analyses of samples by providing short optical pulses to tens of thousands of sample wells or more simultaneously and receiving fluorescent signals from the sample wells for sample analyses. The instruments may be useful for point-of-care genetic sequencing and for personalized medicine.

BACKGROUND

Photodetectors are used to detect light in a variety of applications. Integrated photodetectors have been developed that produce an electrical signal indicative of the intensity of incident light. Integrated photodetectors for imaging applications include an array of pixels to detect the intensity of light received from across a scene. Examples of integrated photodetectors include charge coupled devices (CCDs) and Complementary Metal Oxide Semiconductor (CMOS) image sensors.

Instruments that are capable of massively-parallel analyses of biological or chemical samples are typically limited to laboratory settings because of several factors that can include their large size, lack of portability, requirement of a skilled technician to operate the instrument, power need, need for a controlled operating environment, and cost. When a sample is to be analyzed using such equipment, a common paradigm is to extract a sample at a point of care or in the field, send the sample to the lab and wait for results of the analysis. The wait time for results can range from hours to days.

SUMMARY OF THE DISCLOSURE

Some aspects of the present disclosure provide an integrated circuit comprising a photodetection region configured to receive, in a first direction, incident photons, generate, in response to receiving the incident photons, charge carriers, and induce, in the first direction, a first intrinsic electric field and one or more charge storage regions configured to receive the charge carriers from the photodetection region.

Some aspects of the present disclosure provide a method comprising inducing, in a first direction, a first intrinsic electric field in a photodetection region of an integrated circuit, receiving, in the first direction, incident photons at the photodetection region, and receiving, at one or more charge storage regions of the integrated circuit, charge carriers generated in the photodetection region in response to the incident photons.

Some aspects of the present disclosure provide an integrated circuit comprising a photodetection region configured to generate, in response to receiving incident photons, charge carriers and induce, in a first direction, a first intrinsic electric field, one or more charge storage regions configured to receive the charge carriers from the photodetection region, and one or more transfer gates positioned, in the first direction, after the photodetection region and the one or more charge storage regions, and configured to control transfer of charge carriers from the photodetection region to the one or more charge storage regions and/or from the one or more charge storage regions to a readout region.

Some aspects of the present disclosure provide a method comprising inducing, in a first direction, a first intrinsic electric field in a photodetection region of an integrated circuit, generating, in the photodetection region in response to receiving incident photons, charge carriers, receiving, at one or more charge storage regions, the charge carriers from the photodetection region, and controlling transfer of charge carriers from the photodetection region to the one or more charge storage regions and/or from the one or more charge storage regions to a readout region using one or more transfer gates positioned, in the first direction, after the photodetection region and the one or more charge storage regions.

Some aspects of the present disclosure provide an integrated circuit comprising a photodetection region configured to receive, in a first direction, incident photons and generate, in response to receiving the incident photons, charge carriers, one or more charge storage regions configured to receive the charge carriers from the photodetection region, and one or more charged and/or biased regions configured to induce a charge carrier depletion in the photodetection region for propagating the charge carriers, at least partially in the first direction, from the photodetection region toward the one or more charge storage regions.

Some aspects of the present disclosure provide a method comprising inducing in a photodetection region of an integrated circuit, a charge carrier depletion, receiving, in a first direction, incident photons at the photodetection region, generating, in the photodetection region in response to receiving the incident photons, charge carriers, propagating, at least partially in the first direction, and receiving, at one or more charge storage regions of the integrated circuit, the charge carriers from the photodetection region.

Some aspects of the present disclosure provide an integrated circuit comprising a photodetection region configured to receive, in a first direction, incident photons and generate, in response to receiving the incident photons, charge carriers, one or more charge storage regions configured to receive the charge carriers from the photodetection region, and one or more regions configured to induce an intrinsic charge carrier depletion in the photodetection region.

Some aspects of the present disclosure provide a method comprising inducing in a photodetection region of an integrated circuit, an intrinsic charge carrier depletion, receiving, in a first direction, incident photons at the photodetection region, generating, in the photodetection region in response to receiving the incident photons, charge carriers and receiving, at one or more charge storage regions of the integrated circuit, the charge carriers from the photodetection region.

Some aspects of the present disclosure provide a method of manufacturing an integrated circuit, the method comprising forming a photodetection region of the integrated circuit so as to induce, in the photodetection region in a first direction in which the photodetection region is configured to receive incident photons, a first electric field.

Some aspects of the present disclosure provide a method of manufacturing an integrated circuit, the method comprising forming a photodetection region of the integrated circuit and forming one or more charged regions to induce an intrinsic charge carrier depletion in the photodetection region.

Some aspects of the present disclosure provide a method of manufacturing an integrated circuit, the method comprising forming one or more charged and/or biased regions between a first photodetection region of a first pixel and a second photodetection region of a second pixel.

The foregoing summary is not intended to be limiting. Moreover, in accordance with various embodiments, aspects of the present disclosure may be implemented alone or in combination with other aspects.

BRIEF DESCRIPTION OF DRAWINGS

FIG. 1-2 is a cross-sectional view of a pixel of the integrated device of FIG. 1-1, according to some embodiments.

FIG. 1-3 is a circuit diagram of the pixel of FIG. 1-2, according to some embodiments.

FIG. 1-4 is a diagram showing example charge transfer in the pixel of FIG. 1-3, according to some embodiments.

FIG. 2-1A is a top view of an example array of pixels with shield portions that may be included in the integrated device of FIG. 1-1, according to some embodiments.

FIG. 2-1B is a top view of an example array of pixels that may be included in the integrated device of FIG. 1-1 including shield portions in an alternative configuration, according to some embodiments.

FIG. 2-1C is a top view of an example array of pixels that may be included in the integrated device of FIG. 1-1 including shield portions in a further alternative configuration, according to some embodiments.

FIG. 2-2A is a top view of a pixel of the array shown in FIG. 2-1A, according to some embodiments.

FIG. 2-2B is a top view of a pixel of the array shown in FIG. 2-1B, according to some embodiments.

FIG. 2-2C is a top view of a pixel of the array shown in FIG. 2-1C, according to some embodiments.

FIG. 2-3 is a layout sketch of an example pixel that may be included in the arrays of FIG. 2-1A, 2-1B, or 2-1C, according to some embodiments.

FIG. 2-4A is a layout sketch of an alternative example pixel that may be included in the arrays of FIGS. 2-1A, 2-1B, and 2-1C, according to some embodiments.

FIG. 2-4B is a layout sketch of the pixel of FIG. 2-4A, according to some embodiments.

FIG. 2-5A is a layout sketch of an example pixel having discontinuous C/B regions that may be included in the arrays of FIGS. 2-1A, 2-1B, and 2-1C, according to some embodiments.

FIG. 2-5B is a layout sketch of an alternative example pixel having discontinuous C/B regions that may be included in the arrays of FIGS. 2-1A, 2-1B, and 2-1C, according to some embodiments.

FIG. 2-6A is a cross-sectional schematic view of an example pixel that may be included in the arrays of FIGS. 2-1A and 2-1B, according to some embodiments.

FIG. 2-6B is a cross-sectional schematic view of an alternative example pixel that may be included in the arrays of FIGS. 2-1A and 2-1B according to some embodiments.

FIG. 2-7A is a cross-sectional schematic view of an example pixel that may be included in the arrays of FIGS. 2-1A and 2-1B with a photodetection region extending below the charge storage regions, according to some embodiments.

FIG. 2-7B is a cross-sectional schematic of a view of an alternative example pixel that may be included in the arrays of FIGS. 2-1A and 2-1B with a photodetection region extending below the charge storage regions, according to some embodiments.

FIG. 2-8 is a cross-sectional schematic view of an example pixel that may be included in the arrays of FIGS. 2-1A and 2-1B with barriers extending alongside only a portion of the photodetection region in the first direction, according to some embodiments.

FIG. 2-9 is a cross-sectional schematic view of the pixel of FIG. 2-2C, according to some embodiments.

FIG. 2-10 is a cross-sectional schematic view of an example pixel that may be included in the array of FIG. 2-1C having charged and/or biased regions extending alongside the photodetection region from the shields to the transfer gates in the first direction, according to some embodiments.

FIG. 2-11 is a cross-sectional schematic view of an example pixel that may be included in the array of FIG. 2-1C having multiple barriers positioned alongside the photodetection region in the first direction, according to some embodiments.

FIG. 2-12 is a cross-sectional schematic view of a portion of an example pixel that may be included in the arrays of FIGS. 2-1A, 2-1B, and 2-1C, according to some embodiments.

FIG. 2-13 is a layout sketch of an example pixel having multiple charge storage regions that may be included in the arrays of FIGS. 2-1A, 2-1B, and 2-1C, according to some embodiments.

FIG. 2-14 is a diagram showing example charge transfer in the pixel of FIG. 2-13, according to some embodiments.

FIG. 3-1 is a perspective view of an example pixel that may be included in the integrated device of FIG. 1-1 showing dopant concentration within the pixel, according to some embodiments.

FIG. 3-2 is a side view of a cross-section of the pixel of FIG. 3-1 showing dopant concentration within the pixel, according to some embodiments.

FIG. 3-3 is a graph of n-type and total dopant concentration versus depth in a first sub-cross-section of the pixel of FIG. 3-2, according to some embodiments.

FIG. 3-4 is a graph of p-type dopant concentration versus depth in a second sub-cross-section of the pixel of FIG. 3-2, according to some embodiments.

FIG. 3-5A is a side view of a cross-section of the pixel of FIG. 3-1 incorporating techniques described herein showing charge carrier density within the pixel, according to some embodiments.

FIG. 3-5B is a side view of a cross-section of another example pixel showing charge carrier density within the pixel, according to some embodiments.

FIG. 3-6A is a graph showing a number of charge carriers at different depths of the pixels of FIGS. 3-5A and 3-5B over time, according to some embodiments.

FIG. 3-6B is a magnified view of a portion of the graph of FIG. 3-6A, according to some embodiments.

FIG. 3-7A is a side view of a cross-section of the pixel of FIG. 3-1 incorporating techniques described herein showing electric fields within the pixel, according to some embodiments.

FIG. 3-7B is a side view of a cross-section of the pixel of FIG. 3-5B showing electric fields within the pixel, according to some embodiments.

FIG. 3-8 is a graph of electric field versus depth for sub-cross-sections of the pixels of FIGS. 3-1 and 3-5B, according to some embodiments.

FIG. 3-9A is a graph showing a number of charge carriers at different depths of the pixel of FIG. 3-1 over time, according to some embodiments.

FIG. 3-9B is a magnified view of a portion of the graph of FIG. 3-9A, according to some embodiments.

FIG. 3-9C is a further magnified view of a portion of the graph of FIG. 3-9B, according to some embodiments.

FIG. 3-10 is a graph showing a number of charge carriers over time for multiple pixels having different configurations, according to some embodiments.

FIG. 3-11A is a side view of a cross-section of the pixel of FIG. 3-1 showing charge carrier density within the pixel 1 nanosecond after an excitation pulse, according to some embodiments.

FIG. 3-11B is a side view of a cross-section of another example pixel showing charge carrier density within the pixel 1 nanosecond after an excitation pulse, according to some embodiments.

FIG. 3-12A is a side view of a cross-section of the pixel of FIG. 3-1 showing electric fields within the pixel, according to some embodiments.

FIG. 3-12B is a side view of a cross-section of the pixel of FIG. 3-11B showing electric fields within the pixel, according to some embodiments.

FIG. 3-13 is a graph of electric field versus depth for sub-cross-sections of the pixels of FIGS. 3-1 and 3-11B, according to some embodiments.

FIG. 4-1 is a side view of a cross-section of an example pixel with one or more charged regions that may be included in the integrated device of FIG. 1-1, according to some embodiments.

FIG. 4-2 is a side view of a cross-section of an example pixel with one or more metal regions that may be included in the integrated device of FIG. 1-1, according to some embodiments.

FIG. 4-3 is a side view of a cross-section of an example pixel with one or more charged regions and an optically directive structure that may be included in the integrated device of FIG. 1-1, according to some embodiments.

FIG. 5-1A is a block diagram of an integrated device and an instrument, according to some embodiments.

FIG. 5-1B is a schematic of an apparatus including an integrated device, according to some embodiments.

FIG. 5-1C is a block diagram depiction of an analytical instrument that includes a compact mode-locked laser module, according to some embodiments.

FIG. 5-1D depicts a compact mode-locked laser module incorporated into an analytical instrument, according to some embodiments.

FIG. 5-2 depicts a train of optical pulses, according to some embodiments.

FIG. 5-3 depicts an example of parallel reaction chambers that can be excited optically by a pulsed laser via one or more waveguides according to some embodiments.

FIG. 5-4 illustrates optical excitation of a reaction chamber from a waveguide, according to some embodiments.

FIG. 5-5 depicts further details of an integrated reaction chamber, optical waveguide, and time-binning photodetector, according to some embodiments.

FIG. 5-6 depicts an example of a biological reaction that can occur within a reaction chamber, according to some embodiments.

FIG. 5-7 depicts emission probability curves for two different fluorophores having different decay characteristics according to some embodiments.

FIG. 5-8 depicts time-binning detection of fluorescent emission, according to some embodiments.

FIG. 5-9 depicts a time-binning photodetector, according to some embodiments.

FIG. 5-10A depicts pulsed excitation and time-binned detection of fluorescent emission from a sample, according to some embodiments.

FIG. 5-10B depicts a histogram of accumulated fluorescent photon counts in various time bins after repeated pulsed excitation of a sample, according to some embodiments.

FIG. 5-11A depicts a histogram corresponding to a T nucleotide or nucleotide analog, according to some embodiments.

FIG. 5-11B depicts a histogram corresponding to an A nucleotide or nucleotide analog, according to some embodiments.

FIG. 5-11C depicts a histogram corresponding to a C nucleotide or nucleotide analog, according to some embodiments.

FIG. 5-11D depicts a histogram corresponding to a G nucleotide or nucleotide analog, according to some embodiments.

FIG. 5-12 is a flow diagram illustrating a method of sequencing a labeled polypeptide by Edman degradation according to some embodiments.

FIG. 5-13 includes a flow diagram illustrating a method of sequencing in which discrete binding events give rise to signal pulses of a signal output, and a graph illustrating the signal output according to some embodiments.

Figure 1:
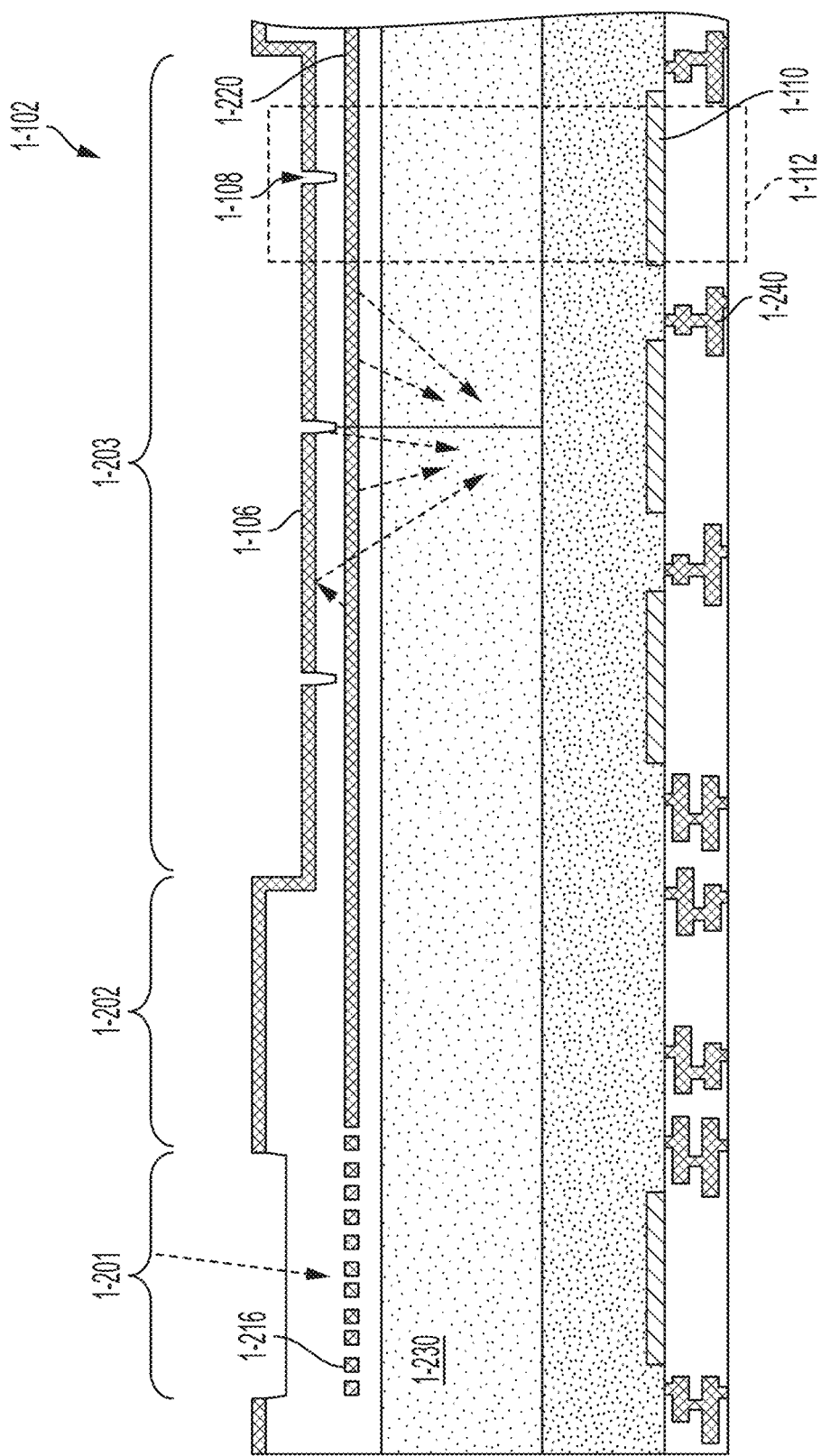
FIG. 1-1 is a cross-sectional schematic of an exemplary integrated device illustrating a row of pixels, according to some embodiments.

The features and advantages of the present disclosure will become more apparent from the detailed description set forth below when taken in conjunction with the drawings. When describing embodiments in reference to the drawings, directional references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of features of an embodied device. A device may be embodied using other orientations.

DETAILED DESCRIPTION

I. Introduction

Aspects of the present disclosure relate to integrated devices, instruments and related systems capable of analyzing samples in parallel, including identification of single molecules and nucleic acid sequencing. Such an instrument may be compact, easy to carry, and easy to operate, allowing a physician or other provider to readily use the instrument and transport the instrument to a desired location where care may be needed. Analysis of a sample may include labeling the sample with one or more fluorescent markers, which may be used to detect the sample and/or identify single molecules of the sample (e.g., individual nucleotide identification as part of nucleic acid sequencing). A fluorescent marker may become excited in response to illuminating the fluorescent marker with excitation light (e.g., light having a characteristic wavelength that may excite the fluorescent marker to an excited state) and, if the fluorescent marker becomes excited, emit emission light (e.g., light having a characteristic wavelength emitted by the fluorescent marker by returning to a ground state from an excited state). Detection of the emission light may allow for identification of the fluorescent marker, and thus, the sample or a molecule of the sample labeled by the fluorescent marker. According to some embodiments, the instrument may be capable of massively-parallel sample analyses and may be configured to handle tens of thousands of samples or more simultaneously.

The inventors have recognized and appreciated that an integrated device having sample wells configured to receive the sample and integrated optics formed on the integrated device and an instrument configured to interface with the integrated device may be used to achieve analysis of this number of samples. The instrument may include one or more excitation light sources, and the integrated device may interface with the instrument such that the excitation light is delivered to the sample wells using integrated optical components (e.g., waveguides, optical couplers, optical splitters) formed on the integrated device. The optical components may improve the uniformity of illumination across the sample wells of the integrated device and may reduce a large number of external optical components that might otherwise be needed. Furthermore, the inventors have recognized and appreciated that integrating photodetection regions (e.g., photodiodes) on the integrated device may improve detection efficiency of fluorescent emissions from the sample wells and reduce the number of light-collection components that might otherwise be needed.

In some embodiments, the integrated device may receive fluorescence emission photons and transmit charge carriers to one or more charge storage regions. For example, a photodetection region may be positioned on the integrated device to receive the fluorescent emission photons in an optical direction, and the photodetection region also may be coupled to one or more charge storage regions (e.g., storage diodes) of the integrated device, such that the charge storage region(s) may collect charge carriers generated in the photodetection region in response to the fluorescent emission photons. A number of charge carriers accumulated in the charge storage region(s) may be read out to obtain information about the sample from which the fluorescence emission photons were received.

The inventors have recognized that it is desirable to generate and transfer charge carriers from the photodetection region to the charge storage region(s) as quickly and efficiently as possible, but that it is challenging to do so quickly and efficiently when the charge storage region(s) are positioned far from where incident photons are received at the integrated device. For instance, it can take a long time for charge carriers generated in the integrated device in response to the incident photons to reach the charge storage region(s). The long travel time can cause charge carriers to reach the charge storage region(s) at a time that is too late to be useful, as the arrival times of the charge carriers may be used to obtain information about the sample. In such cases, a large quantity of late arriving charge carriers can indicate false timing information about the sample, causing inaccurate information to be extracted from the integrated device. Quick and efficient charge transfer is particularly challenging in integrated devices in which the integrated device receives the incident photons on one side of the integrated device and the charge storage region(s) and/or transfer gate(s) are on an opposite side of the integrated device.

To solve the above problems, the inventors have developed integrated devices and associated techniques that increase the rate and efficiency of charge carrier generation and transfer within the integrated devices. Some aspects of the present disclosure relate to integrated circuits that are configured to induce one or more intrinsic electric fields that increase the rate and efficiency of charge transfer within the integrated circuits. Electric fields are intrinsically induced when they are present even in the absence of any electric fields applied externally to the integrated circuit.

In some embodiments, an integrated circuit may have a photodetection region and one or more charge storage regions. The photodetection region may be configured to receive, in a first direction (e.g., a direction from the sample well towards the photodetection region), incident photons and induce, in the first direction, a first intrinsic electric field. For example, the photodetection region may have multiple layers positioned one after another in the first direction and each having different intrinsic electric potential levels, such as having different dopant concentrations. In this example, the first electric field may be induced intrinsically in that the layers of the photodetection region may be configured to induce the electric field even when no external electric fields are applied to the integrated circuit. The charge storage region(s) may be configured to receive charge carriers generated in the photodetection region in response to incident photons. By inducing the first intrinsic electric field in the first direction, charge carriers generated in the photodetection region can be transferred quickly and efficiently by the first intrinsic electric field in the first direction toward the charge storage region(s).

In accordance with various embodiments, intrinsic electric fields described herein may be induced in any direction, and/or in multiple directions, as appropriate for transferring charge carriers within an integrated device. For example, integrated devices described herein may be configured to induce intrinsic electric fields in first and second perpendicular directions where charge carriers are to be transferred in the first direction within the photodetection region and in the second direction from the photodetection region to the charge storage region(s). In some embodiments, intrinsic electric fields described herein may be supplemented with externally applied electric fields. For example, intrinsic electric fields may allow for externally applied electric fields of smaller magnitude to be applied to the integrated device, thereby reducing power consumption and/or heat dissipation in the integrated device.

In some embodiments, an integrated circuit may have a photodetection region configured to induce, in a first direction, a first intrinsic electric field, one or more charge storage regions configured to receive charge carriers generated in the photodetection region in response to incident photons, and one or more transfer gates positioned, in the first direction, after the photodetection region and the charge storage region(s) and configured to control transfer of charge carriers from the photodetection region to the charge storage region(s). The transfer gates may be positioned, in the first direction, after the photodetection region and the charge storage region(s) in that incident photons or charge carriers traveling along the first direction would reach the position(s) of the photodetection region and/or charge storage region(s) along the first direction before reaching the positions of the transfer gates along the first direction. For example, the transfer gate(s) and charge storage region(s) may be positioned on an opposite side of the integrated device from the side on which the photodetection region is configured to receive incident photons, such that charge carriers have a long distance to travel to reach the charge storage region(s). In this example, the first intrinsic electric field may quickly and efficiently transfer charge carriers to the charge storage region(s), thereby facilitating positioning the charge storage region(s) and transfer gate(s) on the opposite of the integrated device. The inventors recognized that this configuration is desirable because fewer incident photons may reach the charge storage region(s) and generate noise charge carriers therein than if the charge storage region(s), and the optical characteristics of the transfer gate(s) may have less effect on incident photons, than if the charge storage region(s) and transfer gate(s) were positioned on the side of the integrated device that receives incident photons.

Some aspects of the present disclosure relate to integrated circuits configured to induce a charge carrier depletion in the photodetection region(s) of the integrated circuits. The inventors have recognized that the presence of free charge carriers in the photodetection region can affect the rate and efficiency of charge transfer within the photodetection region and between the photodetection region and the charge storage region(s). In some embodiments, an integrated circuit may include a photodetection region configured to receive, in a first direction, incident photons, and generate, in response to receiving the incident photons, charge carriers and one or more charge storage regions configured to receive the charge carriers from the photodetection region. The integrated circuit may further include one or more charged and/or biased regions configured to induce a charge carrier depletion in the photodetection region for propagating the charge carriers, at least partially in the first direction, from the photodetection region toward the charge storage region(s). For example, the charged and/or biased regions may include a charge layer configured to deplete the photodetection region of charge carriers by attracting the charge carriers to the charge layer. In this example, the charge layer may be configured to induce an intrinsic charge carrier depletion in the photodetection region, in that the charge layer may deplete the photodetection region even when no external electric field or other external means of depletion is applied to the integrated device.

Alternatively or additionally, the charged and/or biased region may include a metal region configured to receive a voltage bias that induces the charge carrier depletion in the photodetection region. For example, the voltage bias may be supplied to the integrated device from an external power source, such as a ground connection to a power supply. By inducing a charge carrier depletion in the photodetection region, the photodetection region may receive generate and transfer charge carriers more quickly and efficiently in response to incident photons. In some embodiments, the photodetection region may have fewer than $10^{12}$ charge carriers per cubic centimeter (cm$^3$), fewer than $10^6$ charge carriers per cm$^3$, and/or fewer than $10^3$ charge carriers per cm$^3$ when the photodetection region is depleted of charge carriers.

The inventors have also developed processes for operating and/or manufacturing integrated devices as described herein. It should be appreciated that techniques described herein may be implemented alone or in combination, as the present disclosure is not so limited.

II. Integrated Device Overview

A cross-sectional schematic of integrated device 1-102 illustrating a row of pixels 1-112 is shown in FIG. 1-1, according to some embodiments. Integrated device 1-102 may include coupling region 1-201, routing region 1-202, and pixel region 1-203. Coupling region 1-201 may be configured to receive incident excitation light from an excitation light source. Routing region 1-202 may be configured to deliver the excitation light from coupling region 1-201 to pixel region 1-203. Pixel region 1-203 may include a plurality of sample wells 1-108 positioned on a surface at a location separate from coupling region 1-201. For example, coupling region 1-201 may include one or more grating couplers 1-216 and routing region 1-202 may include one or more waveguides 1-220 configured to propagate light from grating coupler(s) 1-216 under sample well(s) 1-108. For instance, evanescent coupling of excitation light from waveguide(s) 1-220 may excite samples in sample well(s) 1-108 to emit fluorescent light.

As shown in FIG. 1-1, one or more at least partially opaque (e.g., metal) layers 1-106 can be disposed over the surface to reflect incident excitation light coupled from waveguide(s) 1-220. Sample wells 1-108 may be free of layer(s) 1-106 to allow samples to be placed in sample well(s) 1-108. In some embodiments, the directionality of the emission light from a sample well 1-108 may depend on the positioning of the sample in the sample well 1-108 relative to metal layer(s) 1-106 because metal layer(s) 1-106 may act to reflect emission light. In this manner, a distance between metal layer(s) 1-106 and a fluorescent marker on a sample positioned in a sample well 1-108 may impact the efficiency of photodetector(s) 1-110, that are in the same pixel as the sample well, to detect the light emitted by the fluorescent marker. The distance between metal layer(s) 1-106 and the bottom surface of a sample well 1-108, which is proximate to where a sample may be positioned during operation, may be in the range of 100 nm to 500 nm, or any value or range of values in that range. In some embodiments the distance between metal layer(s) 1-106 and the bottom surface of a sample well 1-108 is approximately 300 nm.

As shown in FIG. 1-1, pixel region 1-203 can include one or more rows of pixels 1-112. One pixel 1-112, illustrated by the dotted rectangle, is a region of integrated device 1-102 that includes a sample well 1-108 and one or more photodetectors 1-110 (e.g., including a photodetection region) associated with the sample well 1-108. In some embodiments, each photodetector 1-110 can include a photodetection region and one or more charge storage regions configured to receive charge carriers generated in the photodetection region in response to incident light from the sample well 1-108. When excitation light coupled from waveguide(s) 1-220 illuminates a sample located within the sample well 1-108, the sample may reach an excited state and emit emission light. The emission light may be detected by one or more photodetectors 1-110 associated with the sample well 1-108. FIG. 1-1 schematically illustrates an optical axis of emission light (shown as the solid line) from a sample well 1-108 to photodetector(s) 1-110 of pixel 1-112. The photodetector(s) 1-110 of pixel 1-112 may be configured and positioned to detect emission light from sample well 1-108. For an individual pixel 1-112, a sample well 1-108 and its respective photodetector(s) 1-110 may be aligned along a common optical axis. In this manner, the photodetector(s) 1-110 may overlap with the sample well 1-108 within a pixel 1-112.

Also shown in FIG. 1-1, integrated device 1-102 can include one or more photonic structures 1-230 positioned between sample wells 1-108 and photodetectors 1-110. For example, photonic structures 1-230 may be configured to increase the amount of emission light that reaches photodetectors 1-110 from sample wells 1-108. Alternatively or additionally, photonic structures 1-230 may be configured to reduce or prevent excitation light from reaching photodetectors 1-110, which may otherwise contribute to signal noise in detecting the emission light. As shown in FIG. 1-1, photonic structures 1-230 may be positioned between waveguide(s) 1-220 and photodetectors 1-110. According to various embodiments, photonic structures 1-230 may include one or more optical rejection photonic structures including a spectral filter, a polarization filter, and a spatial filter. In some embodiments, photonic structures 1-230 may be positioned to align with individual sample wells 1-108 and their respective photodetector(s) 1-110 along a common axis.

As shown in FIG. 1-1, metal layers 1-240 may be positioned on an opposite side of photodetectors 1-110 from the side that faces sample wells 1-108. In some embodiments, metal layers 1-240 may be configured to route control signals to and/or from portions of integrated device 1-102. For example, the control signals may be received from a control circuit within and/or coupled to one or more conductive pads (not shown) of integrated device 1-102 and routed to pixels 1-112 via metal layers 1-240.

In some embodiments, the distance between the sample and the photodetector(s) may also impact efficiency in detecting emission light. By decreasing the distance light has to travel between the sample and the photodetector(s) 1-110, detection efficiency of emission light may be improved. In addition, smaller distances between the sample and the photodetector(s) 1-110 may allow for pixels that occupy a smaller area footprint of the integrated device, which can allow for a higher number of pixels to be included in the integrated device. At the same time, the substrate depth at which photodetectors 1-110 are disposed can affect the amount of generated charge carriers that flow through to the side on which metal layers 1-240 are disposed. The distance between the bottom surface of a sample well 1-108 and the photodetector(s) 1-110 may be in the range of 5 μm to 15 μm, or any value or range of values in that range, in some embodiments, but embodiments are not so limited. It should be appreciated that, in some embodiments, emission light may be provided through other means than an excitation light source and a sample well. Accordingly, some embodiments may not include sample well 1-108.

A sample to be analyzed may be introduced into sample well 1-108 of pixel 1-112. The sample may be a biological sample or any other suitable sample, such as a chemical sample. The sample may include multiple molecules and the sample well may be configured to isolate a single molecule. In some instances, the dimensions of the sample well 1-108 may act to confine a single molecule within the sample well 1-108, allowing measurements to be performed on the single molecule. Excitation light may be delivered into the sample well 1-108, so as to excite the sample or at least one fluorescent marker attached to the sample or otherwise associated with the sample while it is within an illumination area within the sample well 1-108.

In operation, parallel analyses of samples within the sample wells 1-108 are carried out by exciting some or all of the samples within the wells using excitation light and detecting signals from sample emission with the photodetectors 1-110. Emission light from a sample may be detected by a corresponding photodetector 1-110 and converted to at least one electrical signal. The electrical signals may be transmitted along conducting lines (e.g., metal layers 1-240) of integrated device 1-102, which may be connected to an instrument and/or control circuit interfaced with the integrated device 1-102. The electrical signals may be subsequently processed and/or analyzed by the instrument and/or control circuit.

Figures 1, 2:
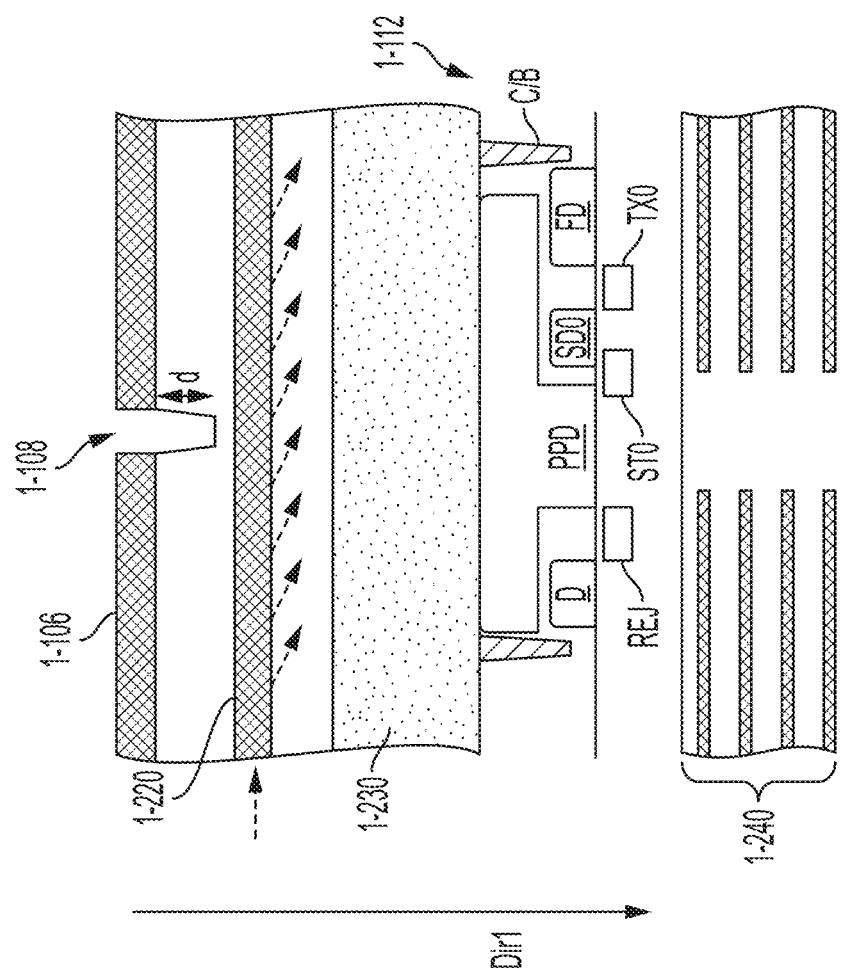

FIG. 1-2 illustrates a cross-sectional view of a pixel 1-112 of integrated device 1-102, according to some embodiments. As shown in FIG. 1-2, pixel 1-112 includes a photodetection region, which may be a pinned photodiode (PPD), a charge storage region, which may be a storage diode (SD0), a readout region, which may be a floating diffusion (FD) region, a drain region D, and transfer gates REJ, ST0, and TX0. In some embodiments, photodetection region PPD, charge storage region SD0, readout region FD, and/or drain region D may be formed in the integrated device 1-102 by doping portions of one or more substrate layers of the integrated device 1-102. For example, the integrated device 1-102 may have a lightly p-doped substrate, and photodetection region PPD, charge storage region SD0, readout region FD, and/or drain region D may be n-doped regions of the substrate. In this example, p-doped regions may be doped using boron and n-doped regions may be doped using phosphorus, although other dopants and configurations are possible. In some embodiments, pixel 1-112 may have an area smaller than or equal to 10 microns by 10 microns, such as smaller than or equal to 7.5 microns×5 microns. It should be appreciated that, in some embodiments, the substrate may be lightly n-doped and photodetection region PPD, charge storage region SD0, readout region FD, and/or drain region D may be p-doped, as embodiments described herein are not so limited.

In FIG. 1-2, photodetection region PPD is configured to receive incident photons in a first direction Dir1, and charge storage region SD0, drain region D, and readout region FD are positioned, in the first direction Dirt, after at least a portion of photodetection region PPD. For example, in FIG. 1-2, portions of photodetection region PPD are positioned between charge storage region SD0, drain region D, and readout region FD and sample well 1-108. Transfer gates ST0, TX0, and REJ are shown in FIG. 1-2 positioned, in the first direction Dir1, after photodetection region PPD, charge storage region SD0, readout region FD, and drain region D. Pixel 1-112 is also shown in FIG. 1-2 including one or more charged and/or biased (C/B) regions, which are described further herein including with reference to FIGS. 2-1A to 2-13.

In some embodiments, photodetection region PPD may be configured to generate charge carriers in response to incident light. For instance, during operation of pixel 1-112, excitation light may illuminate sample well 1-108 causing incident photons, including fluorescent emissions from a sample, to flow along the optical axis OPT to photodetection region PPD, which may be configured to generate fluorescent emission charge carriers in response to the incident photons from sample well 1-108. In some embodiments, the integrated device 1-102 may be configured to transfer the charge carriers to drain region D or to charge storage region SD0. For example, during a drain period following a pulse of excitation light, the incident photons reaching photodetection region PPD may be predominantly excitation photons to be transferred to drain region D to be discarded. In this example, during a collection period following the drain period, fluorescent emission photons may reach photodetection region PPD to be transferred to charge storage region SD0 for collection. In some embodiments, a drain period and collection period may follow each excitation pulse.

In some embodiments, charge storage region SD0 may be configured to receive charge carriers generated in photodetection region PPD in response to the incident light. For example, charge storage region SD0 may be configured to receive and store charge carriers generated in photodetection region PPD in response to fluorescent emission photons from the sample well 1-108. In some embodiments, charge storage region SD0 may be configured to accumulate charge carriers received from photodetection region PPD over the course of multiple collection periods, each preceded by an excitation pulse. In some embodiments, charge storage region SD0 may be electrically coupled to photodetection region PPD by a charge transfer channel. In some embodiments, the charge transfer channel may be formed by doping a region of pixel 1-112 between photodetection region PPD and charge storage region SD0 with a same conductivity type as photodetection region PPD and charge storage region SD0 such that the charge transfer channel is configured to be conductive when at least a threshold voltage is applied to the charge transfer channel and nonconductive when a voltage less than (or greater than, for some embodiments) the threshold voltage is applied to the charge transfer channel. In some embodiments, the threshold voltage may be a voltage above (or below) which the charge transfer channel is depleted of charge carriers, such that charge carriers from photodetection region PPD may travel through the charge transfer channel to charge storage region SD0. For example, the threshold voltage may be determined based on the materials, dimensions, and/or doping configuration of the charge transfer channel.

In some embodiments, transfer gate ST0 may be configured to control transfer of charge carriers from photodetection region PPD to charge storage region SD0. For instance, transfer gate ST0 may be configured to receive a control signal and responsively determine a conductivity of a charge transfer channel electrically coupling photodetection region PPD to charge storage region SD0. For example, when a first portion of a control signal is received at transfer gate ST0, transfer gate ST0 may be configured to bias the charge transfer channel to cause the charge transfer channel to be nonconductive, such that charge carriers are blocked from reaching charge storage region SD0. Alternatively, when a second portion of the control signal is received at transfer gate ST0, transfer gate ST0 may be configured to bias to the charge transfer channel to cause the charge transfer channel to be conductive, such that charge carriers may flow from photodetection region PPD to charge storage region SD0 via the charge transfer channel. In some embodiments, transfer gate ST0 may be formed using polysilicon.

In some embodiments, transfer gate TX0 may be configured to control transfer of charge carriers from charge storage region SD0 to readout region FD in the manner described for transfer gate ST0 in connection with photodetection region PPD and charge storage region SD0. For example, following a plurality of collection periods during which charge carriers are transferred from photodetection region PPD to charge storage region SD0, charge carriers stored in charge storage region SD0 may be transferred to readout region FD to be read out for processing.

In some embodiments, transfer gate REJ may be configured to control transfer of charge carriers from photodetection region PPD to drain region D in the manner described for transfer gate ST0 in connection with photodetection region PPD and charge storage region SD0. For example, excitation photons from the excitation light source may reach photodetection region PPD before fluorescent emission photons from the sample well 1-108 reach photodetection region PPD. In some embodiments, the integrated device 1-102 may be configured to control transfer gate REJ to transfer charge carriers generated in photodetection region PPD in response to the excitation photons to drain region D during a drain period following an excitation light pulse and preceding reception of fluorescent emission charge carriers.

In some embodiments, pixel 1-112 may be electrically coupled to a control circuit of integrated device 1-102, and/or of a system that includes integrated device 1-102, and configured to receive control signals at transfer gates REJ, ST0, and TX0. For example, metal lines of metal layers 1-240 may be configured to carry the control signals to pixels 1-112 of the integrated device 1-102. In some embodiments, a single metal line carrying a control signal may be electrically coupled to a plurality of pixels 1-112, such as an array, subarray, row, and/or column of pixels 1-112. For example, each pixel 1-112 in an array may be configured to receive a control signal from a same metal line and/or net such that the row of pixels 1-112 is configured to drain and/or collect charge carriers from photodetection region PPD at the same time. Alternatively or additionally, each row of pixels 1-112 in the array may be configured to receive different control signals (e.g., row-select signals) during a readout period such that the rows read out charge carriers one row at a time.

Figures 1, 2, 3:
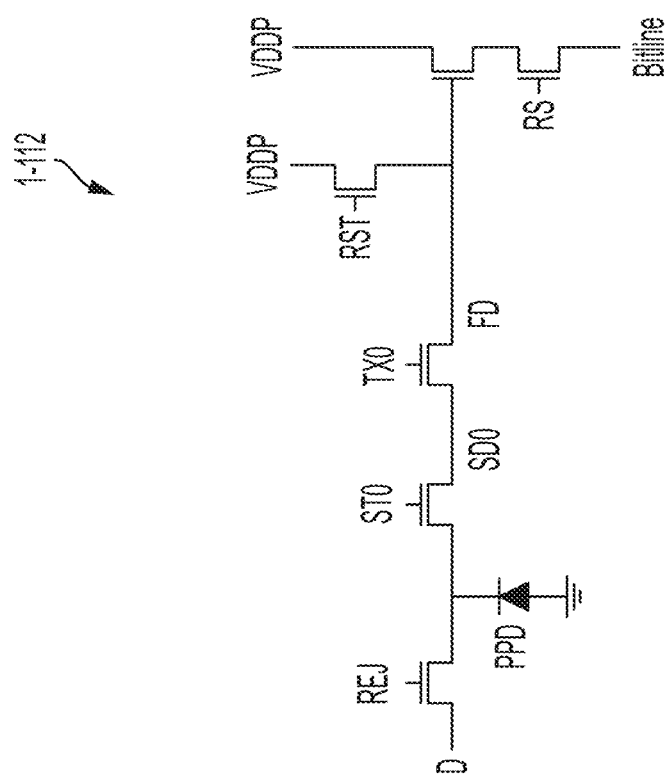

FIG. 1-3 is a circuit diagram of pixel 1-112, according to some embodiments. In FIG. 1-3, transfer gate REJ is the gate of a transistor coupling photodetection region PPD to drain region D, transfer gate ST0 is the gate of a transistor coupling photodetection region PPD to charge storage region SD0, and transfer gate TX0 is the gate of a transistor coupling charge storage region SD0 to readout region FD. As shown in FIG. 1-3, pixel 1-112 further includes a reset (RST) transfer gate coupled to readout region FD and configured for coupling to a power supply voltage VDDP, and a row select (RS) transfer gate coupled between readout region FD and a bitline. When the integrated device 1-102 is coupled to a power source (e.g., at least a DC power supply), transfer gate RST may be coupled to power supply voltage VDDP, which is supplied by the power source and/or regulated by a voltage regulator of integrated device 1-102. For example, transfer gate RST may be configured to cause charge carriers to flow from readout region FD and/or from charge storage region SD0 via transfer gate TX0 and readout region FD, to power supply voltage VDDP.

In some embodiments, transfer gate RST may be configured to reset a voltage of readout region FD. For example, when a reset signal is applied to transfer gate RST, transfer gate RST may bias the transfer channel electrically coupling readout region FD to power supply voltage VDDP, thereby increasing the conductivity of the transfer channel and transferring charge carriers from readout region FD to power supply voltage VDDP. In some embodiments, reset transfer gate RST may be further configured to reset the voltage of charge storage region SD0. For example, when a reset signal is applied to reset transfer gate RST and a control signal is applied to transfer gate TX0, transfer gate TX0 may transfer charge carriers in charge storage region SD0 to readout region FD and transfer gate RST may transfer the charge carriers to power supply voltage VDDP. In some embodiments, integrated device 1-102 may be configured to reset readout region FD and charge storage region SD0 before collecting and reading out charge carriers. For example, integrated device 1-102 may be configured to reset readout region FD and then reset charge storage region SD0 before collecting and reading out charge carriers.

In some embodiments, transfer gate RS may be configured to, in response to a row select control signal, transfer charge carriers from readout region FD to the bitline for processing. In some embodiments, the bitline may be coupled to processing circuitry on the integrated device 1-102 and/or an external circuit configured to receive a voltage level indicative of charge carriers read out to readout region FD. For example, one bitline may be electrically coupled between each pixel 1-112 of an array and processing circuitry. In some embodiments, the processing circuitry may include an analog-to-digital converter (ADC). In some embodiments, integrated device 1-102 may be configured to reset the voltage of readout region FD of each pixel before reading out charge carriers. For example, integrated device 1-102 may be configured to reset the voltage of readout region FD, sample the voltage, transfer charge carriers into readout region FD, and sample the voltage again. In this example, the second sampled voltage may be indicative of a number of the charge carriers transferred into readout region FD when compared to the first sampled voltage. In some embodiments, integrated device 1-102 may be configured to read out charge carriers from each pixel 1-112 to the bitline sequentially, such as row by row and/or column by column (e.g., in response to receiving row select control signals).

It should be appreciated that some arrays of pixels 1-112 may have multiple bitlines electrically coupled to different ones and/or groups of pixels 1-112, such as with one bitline coupling a first column of pixels 1-112 to first processing circuitry and another bitline coupling a second column of pixels 1-112 to second processing circuitry, and so on. In some embodiments, pixels of multiple columns may be read out to respective processing circuitry at the same time. For example, a first pixel of each column may be read out to the respective processing circuitry at the same time, and then a second pixel of each column may be read out to the respective processing circuitry at the same time. It should be appreciated that, in some embodiments, processing circuitry may be provided for each row of the array as an alternative or in addition to each column. In some embodiments, integrated device 1-102 may include multiple units of processing circuitry, such as each being electrically coupled to a bitline.

It should be appreciated that, in accordance with various embodiments, transfer gates described herein may include semiconductor material(s) and/or metal, and may include a gate of a field effect transistor (FET), a base of a bipolar junction transistor (BJT), and/or the like. It should be appreciated that control signals described herein applied to the various transfer gates may vary in shape and/or voltage, such as depending on the electric potential of the semiconductor region and of the regions electrically coupled to the semiconductor region (e.g., neighboring regions).

FIG. 1-4 is a diagram showing example charge transfer in pixel 1-112 in some embodiments. In some embodiments, operation of pixel 1-112 may include one or more collection sequences. An example collection sequence is shown in FIG. 1-4 including a first collection period 1-1, a first readout period 1-2, a second collection period 1-3, and a second readout period 1-4. In some embodiments, each collection period of the collection sequence may be preceded by a drain period, as described further herein. In some embodiments, operation of pixel 1-112 may include one or multiple iterations of the collection sequence shown in FIG. 1-4. In some embodiments, the collection sequence may be coordinated with the excitation of samples in the sample wells 1-108. For example, a single control circuit may be configured to control the excitation light source and operation of pixels 1-112.

In some embodiments, the first collection period 1-1 may include receiving a first plurality of fluorescent emission photons at photodetection region PPD. For example, first collection period 1-1 may occur in response to a pulse of excitation light that illuminates a sample well 1-108 configured to emit fluorescent emission photons toward photodetection region PPD. As shown in FIG. 1-4, photodetection region PPD may be configured to generate charge carriers Q1 in response to the incident fluorescent emission photons and transfer charge carriers Q1 to charge storage region SD0 during the first collection period 1-1. In some embodiments, excitation photons may reach photodetection region PPD during a drain period immediately following the excitation pulse but before first collection period 1-1, during which charge carriers generated in photodetection region PPD in response to the excitation photons may be transferred to drain region D. In some embodiments, collection period 1-1 may be repeated multiple times in response to multiple respective excitation pulses, and charge carriers Q1 may be accumulated in charge storage region SD0 over the course of the collection periods 1-1. In some such embodiments, each collection period 1-1 may be preceded by a drain period. In some embodiments, the collection periods 1-1 and/or drain periods preceding each collection period 1-1 may occur at the same time for each pixel of an array, subarray, row, and/or column of the integrated device 1-102.

In some embodiments, the first readout period 1-2 may occur following one or more collection periods 1-1 during which charge carriers Q1 are accumulated in charge storage region SD0. As shown in FIG. 1-4, during the first readout period 1-2, charge carriers Q1 stored in charge storage region SD0 may be transferred to readout region FD to be read out for processing. In some embodiments, the readout period 1-2 may be performed using correlated double sampling (CDS) techniques. For example, a first voltage of readout region FD may be read out at a first time, followed by a reset of the readout region FD (e.g., by applying a reset signal to transfer gate RST) and the transfer of charge carriers Q1 from charge storage region SD0 to readout region FD, and a second voltage of readout region FD may be read out at a second time following the transfer of charge carriers Q1. In this example, the difference between the first and second voltages may indicate a quantity of charge carriers Q1 transferred from charge storage region SD0 to readout region FD. In some embodiments, the first readout period 1-2 may occur at a different time for each row, column, and/or pixel of an array. For example, by reading out pixels one row or column at a time, a single processing line may be configured to process readout of each row or column in sequence rather than dedicating a processing line to each pixel to read out simultaneously. In other embodiments, each pixel of an array may be configured to read out at the same time, as a processing line may be provided for each pixel of the array. According to various embodiments, charge carriers read out from the pixels may indicate fluorescence intensity, lifetime, spectral, and/or other such fluorescence information of the samples in the sample wells 1-108.

In some embodiments, the second collection period 1-3 may occur in the manner described for collection period 1-1. For example, following the first readout period 1-2, one or more second collection periods 1-3 may follow one or more respective excitation pulses, such as with a drain period preceding each collection period 1-3. As shown in FIG. 1-4, during the second collection period(s) 1-3, charge carriers Q2 generated in photodetection region PPD may be transferred to charge storage region SD0. In some embodiments, a delay between each excitation pulse and corresponding collection period 1-3 may be different from a delay between each excitation pulse and corresponding collection period 1-1. For example, by collecting charge carriers during a different time period following the excitation pulse during different collection periods, charge carriers read out from the collection periods 1-1 and 1-3 may indicate fluorescence lifetime information of the samples in the sample wells 1-108. In some embodiments, the second collection period(s) 1-3 may be followed by a second readout period 1-4 during which charge carriers accumulated in charge storage region SD0 over the course of the second collection period(s) may be read out in the manner described herein for the first readout period 1-2.

According to various embodiments, pixels described herein may include more than one charge storage region, such as two, three, four, or five charge storage regions. For example, a pixel may include a second charge storage region electrically coupled between charge storage region SD0 and readout region FD, with transfer channels electrically coupling charge storage region SD0 to the second charge storage region and the second charge storage region to readout region FD. In this example, transfer gate TX0 may be configured to control the transfer of charge carriers from charge storage region SD0 to the second charge storage region, and the pixel may include another transfer gate configured to control the transfer of charge carriers from the second charge storage region to readout region FD.

III. Charge Carrier Depletion Techniques

The inventors have developed techniques for inducing a charge carrier depletion in the photodetection region of a pixel. In some embodiments, a pixel may have one or more charged and/or biased regions configured to induce the charge carrier depletion in the photodetection region. For example, the charged and/or biased region may include a charge layer configured to induce an intrinsic charge carrier depletion in the photodetection region. In this example, the charge layer may be positioned on one or more sides of the photodetection region and/or on one or more sides of the pixel boundary. Alternatively or additionally, the charged and/or biased region may include a metal region configured to receive a voltage bias to induce the charge carrier depletion. The metal region may be positioned on one or more sides of the photodetection region and/or on one or more sides of the pixel boundary. In either example, the charged and/or biased region may attract charge carriers from within the photodetection region, thereby depleting the photodetection region of charge carriers. In some embodiments, the photodetection region may have fewer than $10^{12}$ charge carriers per cubic centimeter ($cm^3$), fewer than $10^6$ charge carriers per $cm^3$, and/or fewer than $10^3$ charge carriers per $cm^3$ when the photodetection region is depleted of charge carriers. In some embodiments, a pixel may include multiple charged and/or biased regions positioned on respective sides of the photodetection region. In accordance with various embodiments, the multiple charged and/or biased regions may form a continuous structure or may be separate from one another.

Figures 1A, 2:
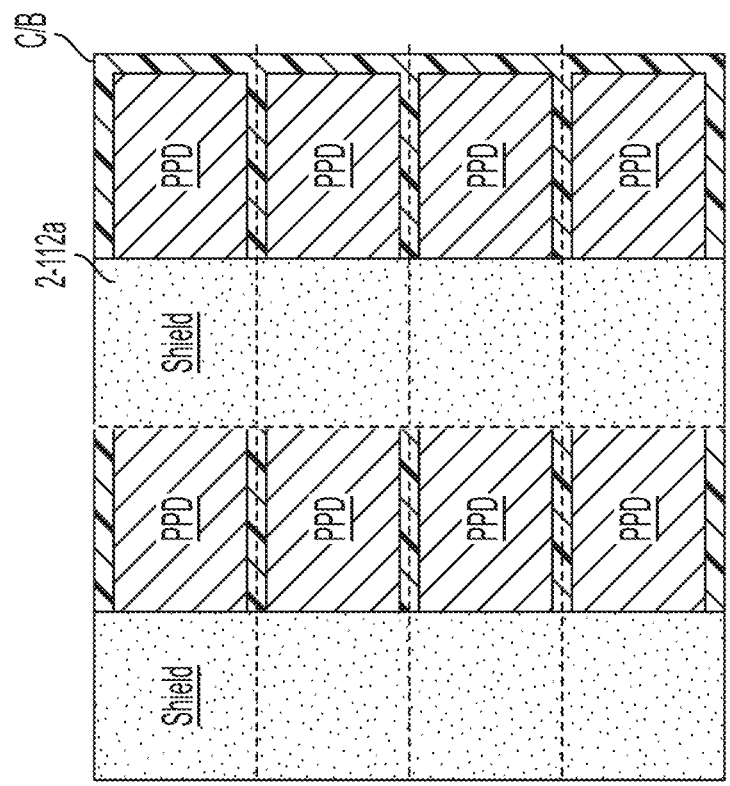

FIG. 2-1A is a top view of an array of pixels 2-112a with shield portions that may be included in the integrated device 1-102, according to some embodiments. In some embodiments, pixels 2-112a may be configured in the manner described herein for pixel 1-112. For example, as shown in FIG. 2-1A, each pixel 2-112a includes a photodetection region PPD. In FIG. 2-1A, each pixel 2-112a also includes multiple C/B regions positioned about the pixel 2-112a and a shield portion.

In some embodiments, photodetection regions PPD pixels 2-112a may be configured to receive incident photons at the top side shown in FIG. 2-1A. In some embodiments, the shield portions may be configured to block incident photons from reaching other components of pixels 2-112a disposed below the shield portions, such as charge storage regions, readout regions, transfer gates, and/or circuitry. For example, the shield portions may be formed using an optically opaque material such as metal (e.g., aluminum or tungsten).

In FIG. 2-1A, the C/B regions of each pixel are positioned on multiple respective sides of the photodetection region PPD. The C/B regions may be alternatively or additionally positioned on multiple respective sides of the boundary of each pixel 2-112a. In some embodiments, the C/B regions of each pixel may be configured to induce a charge carrier depletion in photodetection region PPD. For example, one or more of the C/B regions may include a charge layer configured to induce an intrinsic charge carrier depletion in photodetection region PPD. In some embodiments, the charge layer may include an oxide layer and a metal-oxide compound. In this example, the oxide layer may provide isolation between the photodetection region PPD and the metal-oxide compound. In accordance with various embodiments, the metal-oxide compound may be aluminum oxide ($Al_2O_3$), hafnium dioxide ($HfO_2$), titanium dioxide ($TiO_2$), tantalum pentoxide ($Ta_2O_5$), or any combination thereof. It should be appreciated that other charged oxide materials, such as any other metal-oxides, configured to generate an accumulation layer of free charge carriers, may be used. In some embodiments, C/B regions positioned between two or more pixels may be configured to induce a charge carrier depletion in the photodetection region of some or each of the pixels.

Alternatively or additionally, the C/B regions may include one or more metal regions configured to receive a voltage bias that induces the charge carrier depletion in photodetection region PPD. For example, the metal region(s) may be configured for electrically coupling to a voltage source and/or voltage regulator of integrated device 1-102 and/or an external power supply when the integrated device 1-102 is connected to the power supply. In some embodiments, a pixel may have a combination of charge layers and metal regions configured to receive a voltage bias with the combination configured to induce the charge carrier depletion in photodetection region PPD.

Figures 1B, 2:
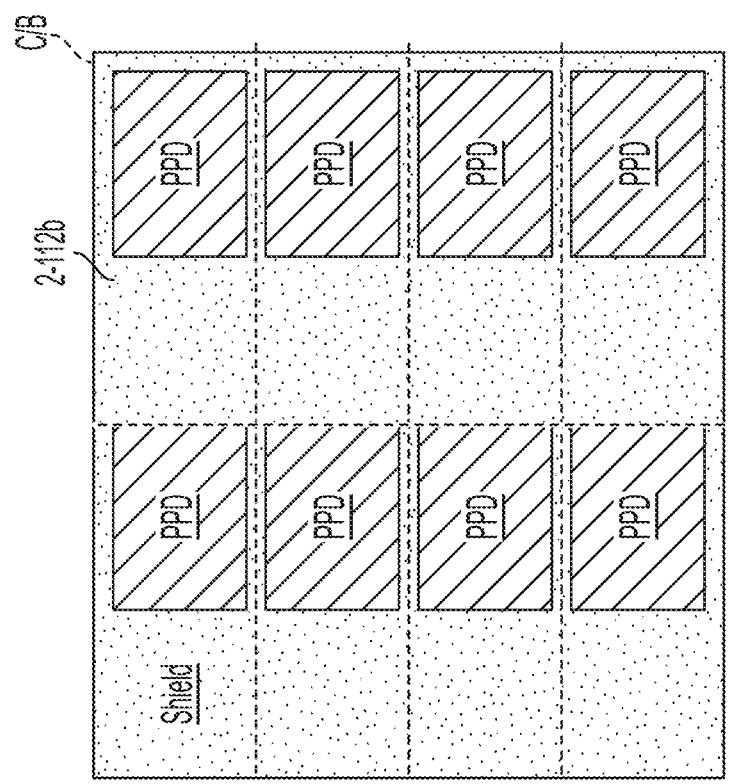

FIG. 2-1B is a top view of an array of pixels 2-112b that may be included in the integrated device 1-102 including shield portions in an alternative configuration, according to some embodiments. Pixels 2-112b may be configured in the manner described herein for pixels 2-112a in connection with FIG. 2-1A. For example, pixels 2-112b include photodetection regions PPD and shield portions. In some embodiments, pixels 2-112b may also include C/B regions below the shield portions and configured in the manner described herein in connection with FIG. 2-1A. In some embodiments, the shield portions shown in FIG. 2-1B may be configured to block incident photons from reaching the C/B regions. For example, in FIG. 2-1B, the shield portions may cover the C/B regions such that the shield portions block photons incident on the C/B regions in the first direction Dir1 (FIG. 1-2) from reaching the C/B regions.

Figures 1C, 2:
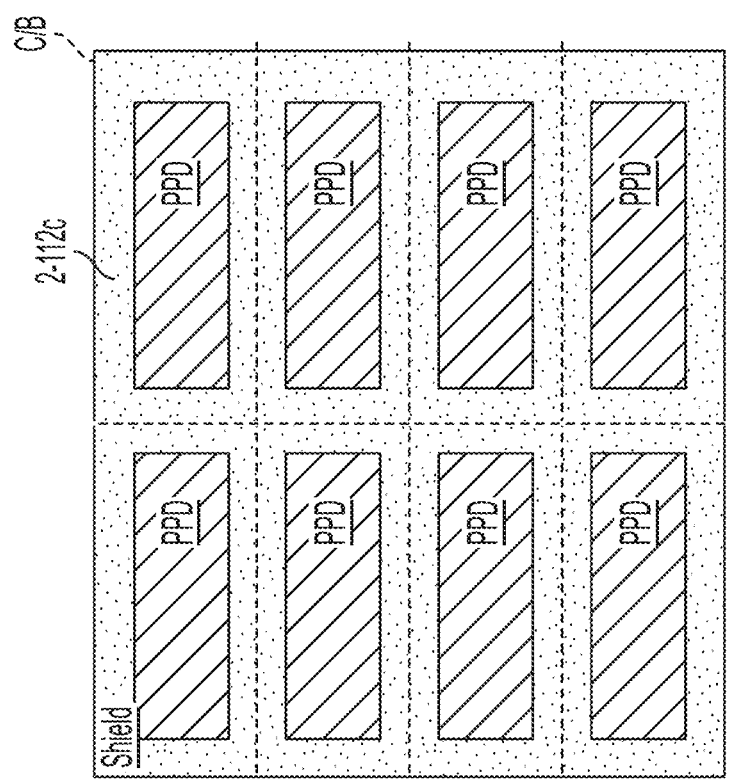

FIG. 2-1C is a top view of an array of pixels 2-112c that may be included in the integrated device 1-102 including shield portions in a further alternative configuration, according to some embodiments. Pixels 1-112c may be configured in the manner described herein for pixels 2-112b in connection with FIG. 2-1B. For example, the shield portions shown in FIG. 2-1C are shown in a manner configured to block incident photons from reaching the C/B regions of the pixels 1-112c. Also shown in FIG. 2-1C, the shield portions leave additional portions of the pixels 1-112c exposed to incident photons. For example, the shield portions may not block incident photons from reaching the charge storage region(s) of the pixel. The inventors recognized that, in some cases, incident photons may be absorbed in the depth of the pixel before reaching the charge storage region(s). Moreover, the inventors recognized that leaving the additional portions of the pixel exposed to incident photons through the shield portions increases the amount of photons received in photodetection region PPD, thereby increasing the number of fluorescent photons that can be received and fluorescent charge carriers that can be collected in the charge storage region(s).

Figures 2, 2A:
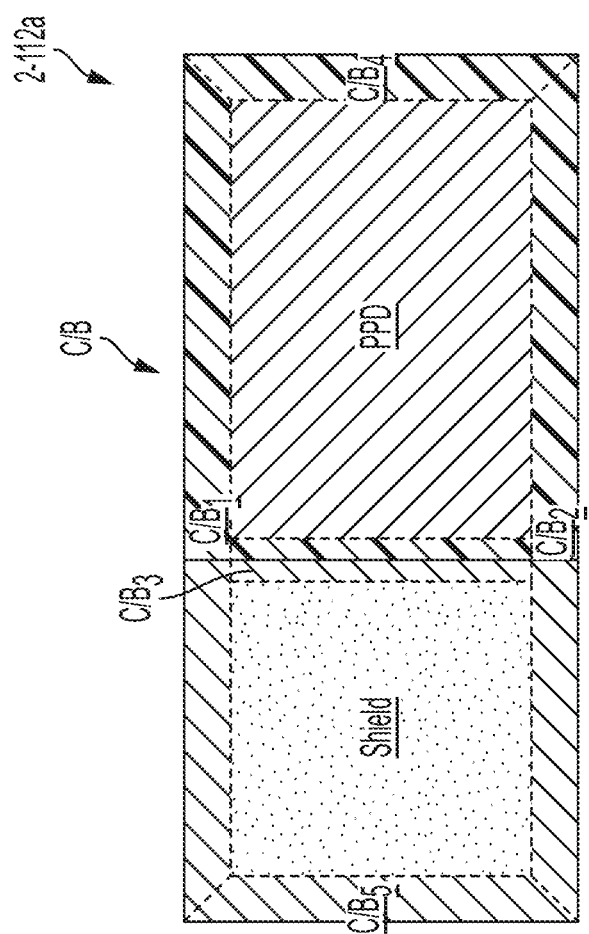

FIG. 2-2A is a top view of a pixel 2-112a of the array shown in FIG. 2-1A, according to some embodiments. As shown in FIG. 2-2A, the C/B regions of the pixel 2-112a include a first region $C/B_1$ positioned on a first side of the photodetection region PPD, a second region $C/B_2$ positioned on a second side of the photodetection region PPD, a third region $C/B_3$ positioned on a third side of the photodetection region PPD, and a fourth region $C/B_4$ positioned on a fourth side of the photodetection region PPD. The first region $C/B_1$ is also positioned on a first side of the boundary of the pixel 2-112a, the second region $C/B_2$ is positioned on a second side of the boundary of the pixel 2-112a, the fourth region $C/B_4$ is positioned on a third side of the boundary of the pixel 2-112a, and a fifth region $C/B_5$ is positioned on a fourth side of the boundary of the pixel 2-112a. The fifth region $C/B_5$ is also positioned on the third side of the photodetection region PPD. For example, in embodiments that do not include third region $C/B_3$, photodetection region PPD may be surrounded on four sides by regions $C/B_1$, $C/B_2$, $C/B_4$, and $C/B_5$, respectively. In some embodiments, a sixth region $C/B_6$ may be positioned on a fifth side of the boundary of pixel 2-112a and/or of photodetection region PPD, such as before photodetection region PPD in the direction in which photodetection region PPD is configured to receive incident photons (e.g., the first direction Dir1). In FIG. 2-2A, C/B regions positioned around the shield portion are covered by the shield portion, which may be configured to block incident photons from reaching the regions covered by the shield portion.

Figures 2, 2B:
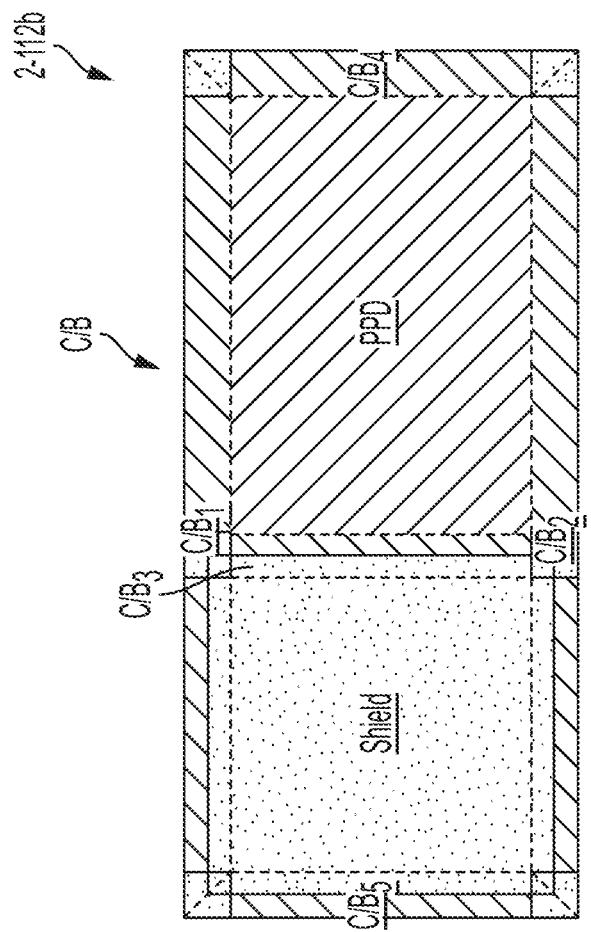

FIG. 2-2B is a top view of a pixel 2-112b of the array shown in FIG. 2-1B, according to some embodiments. As shown in FIG. 2-2A, the C/B regions are configured as described herein for pixel 2-112a in connection with FIG. 2-2A, and the shield portion also covers the first, second, third, and fourth regions $C/B_1$, $C/B_2$, $C/B_3$, and $C/B_4$ on the first, second, third, and fourth sides of the photodetection region PPD.

Figures 2, 2C:
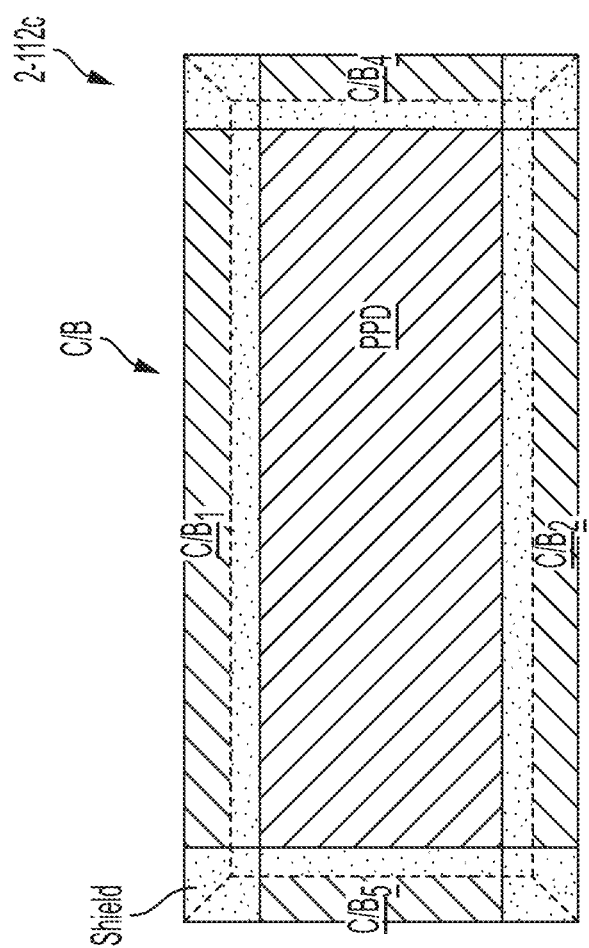
Figures 2, 3:
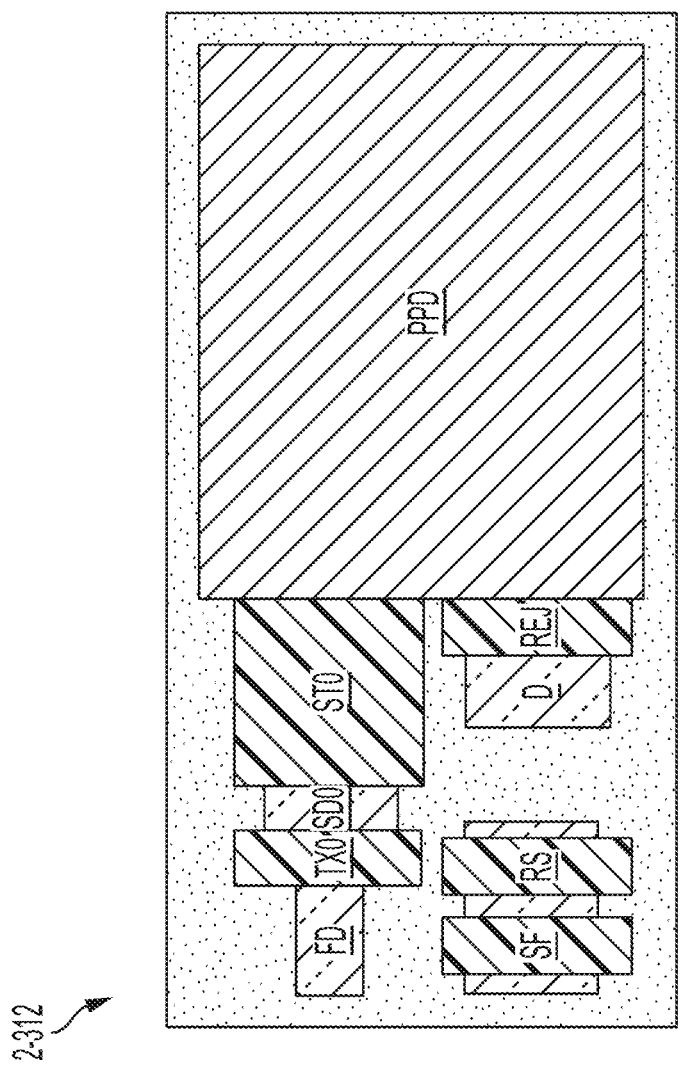
Figures 2, 3, 4, 4A:
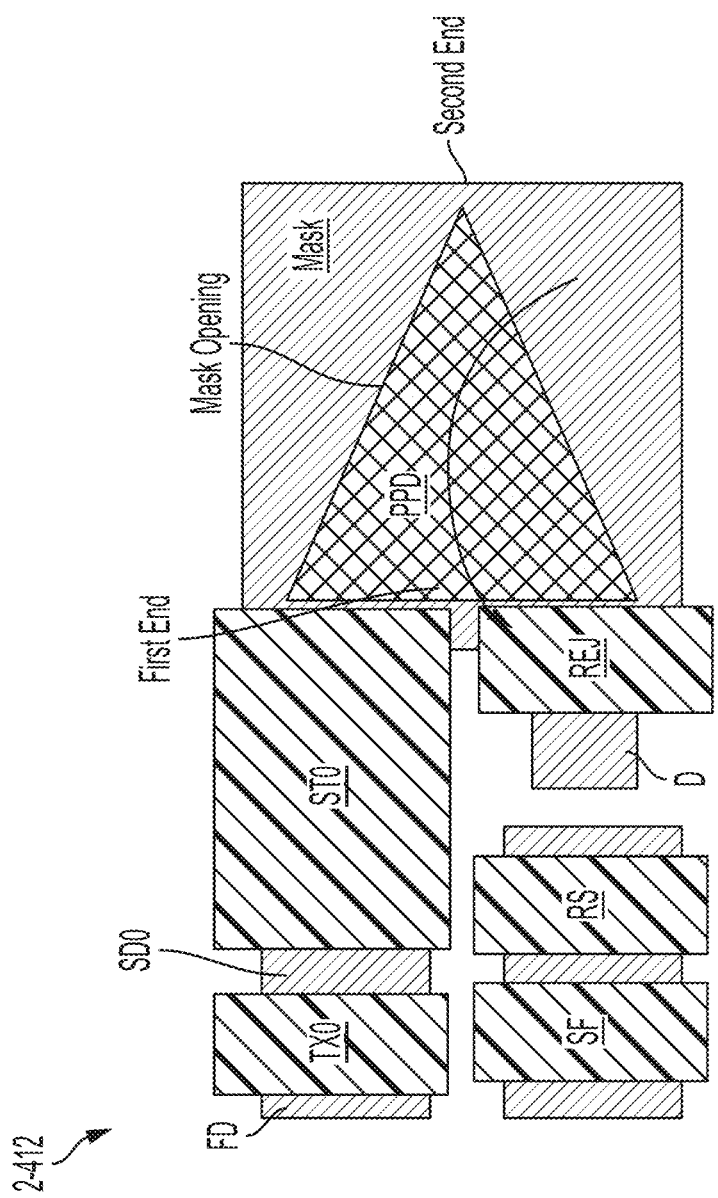
Figures 2, 3, 4, 4B:
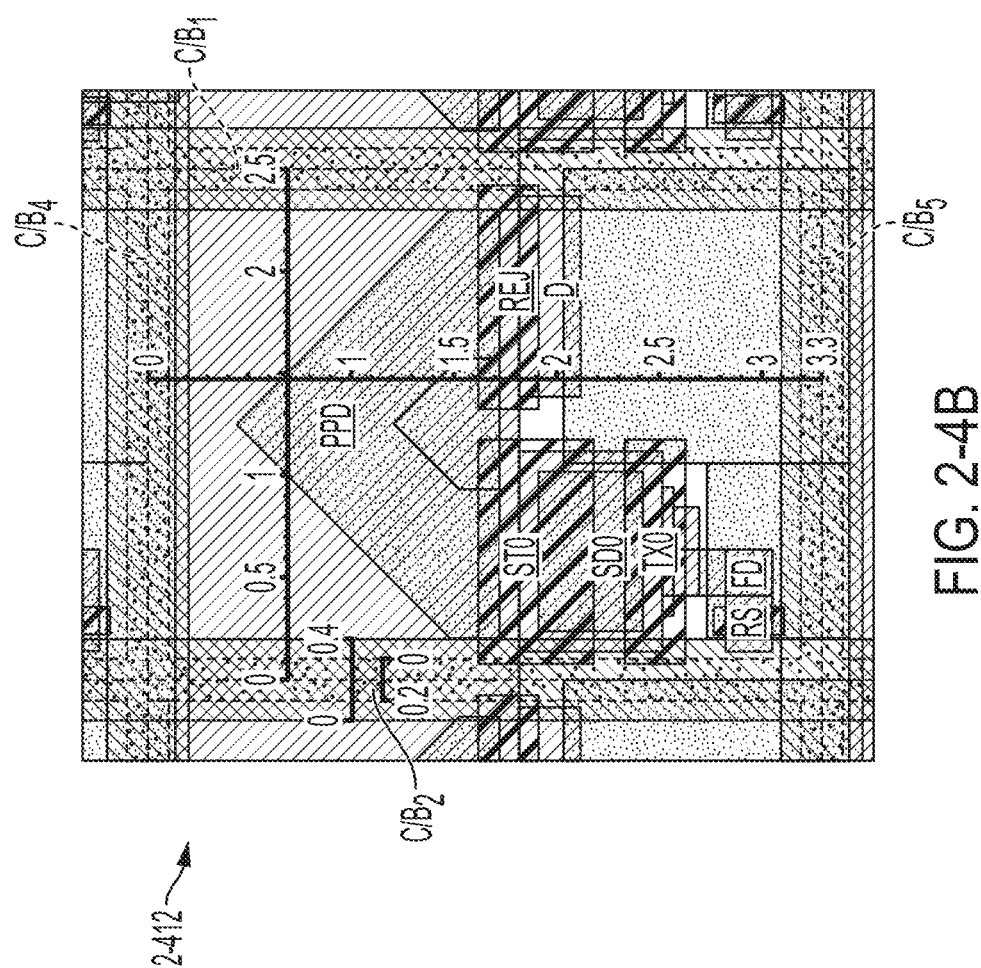

FIG. 2-2C is a top view of a pixel 2-112c of the array shown in FIG. 2-1C, according to some embodiments. As shown in FIG. 2-2C, the C/B regions may be configured as described herein for pixel 2-112a in connection with FIG. 2-2A, except that pixel 2-112c does not include region $C/B_3$. Also shown in FIG. 2-2C, the photodetection region PPD extends from region $C/B_4$ to region $C/B_5$. In some embodiments, the shield portions shown in FIG. 2-2C may be configured to block incident photons from reaching the C/B regions while exposing more of photodetection region PPD to incident photons. In FIG. 2-2C, the opening in the shield portions is rectangular, but the opening may have any shape such as a square according to various embodiments.

It should be appreciated that, in some embodiments, pixels 2-112a and 2-112b may not include region $C/B_3$ and/or may have photodetection region PPD extend from region $C/B_4$ to region $C/B_5$.

FIG. 2-3 is a layout sketch of an example pixel 2-312 that may be included in the arrays of FIG. 2-1A, 2-1B, or 2-1C, according to some embodiments. For example, in some embodiments, pixels 2-112a and 2-112b may be further configured in the manner described herein for pixel 2-312. As shown in FIG. 2-3, pixel 2-312 includes photodetection region PPD, charge storage region SD0, drain region D, and transfer gates ST0, TX0, and REJ. In some embodiments, transfer gate RS may be configured as described herein for FIG. 1-3. In some embodiments, the source follower (SF) transfer gate may be electrically coupled to readout region FD such that a voltage level of readout region FD may be sampled via transfer gate RS. In some embodiments, the shield portion of pixel 2-312 may be configured to block incident photons from reaching charge storage region SD0, drain region D, and transfer gates ST0, TX0, REJ, RS, and SF.

In some embodiments, photodetection region PPD of pixel 2-312 may be configured to induce an intrinsic electric field in a direction from photodetection region PPD toward charge storage region SD0, as described further herein with reference to FIGS. 2-4A and 2-4B. FIG. 2-4A is a layout sketch of an alternative example pixel 2-412 that may be included in the arrays of FIG. 2-1A, 2-1B, or 2-1C, according to some embodiments. Pixel 2-412 may be configured in the manner described herein for pixel 2-312. As shown in FIG. 2-4A, pixel 2-412 similarly includes photodetection region PPD, charge storage region SD0, drain region D, readout region FD, and transfer gates ST0, TX0, REJ, RS, and SF.

In some embodiments, photodetection region PPD may have a triangular dopant configuration configured to induce an intrinsic electric field from photodetection region PPD toward charge storage region SD0 and drain region D. As shown in FIG. 2-4A, photodetection region PPD includes a mask having a triangular opening, with a base of the triangular opening positioned at a first end of photodetection region PPD adjacent charge storage region SD0 and drain region D and an apex of the triangular opening positioned on a second end of photodetection region PPD opposite charge storage region SD0 and drain region D. In some embodiments, photodetection region PPD may be doped through the triangular opening, resulting in a triangular dopant configuration having the shape of the triangular opening. In some embodiments, the triangular dopant configuration may induce an intrinsic electric field in a direction from the second end toward the first end, thereby increasing the rate and efficiency of transferring charge carriers from photodetection region PPD to charge storage region SD0 and drain region D.

FIG. 2-4B is a layout sketch of pixel 2-412, according to some embodiments. FIG. 2-4B further illustrates regions $C/B_1$, $C/B_2$, $C/B_4$, and $C/B_5$ positioned on the sides of the boundary of pixel 2-412, as described herein for pixels 2-112a and 2-112b in connection with FIGS. 2-1A to 2-2B. Although not shown in FIG. 2-4A, pixel 2-412 may also include Row Select (RS) and/or Source Follower (SF) transfer gates and/or a $C/B_3$ region positioned on the side of photodetection region PPD between photodetection region PPD and charge storage region SD0 and drain region D. Although not shown in FIG. 2-4B, it should be appreciated that, in some embodiments, the charge layer(s) of the C/B regions of pixels described herein may be configured for coupling to a power supply voltage, such as at ground potential, to deplete photodetection region PPD of charge carriers. For example, the charge layer(s) may be exposed at the face of the integrated device that supports the transfer gates to allow connections between the charge layer(s) and metal routing to receive the power supply voltage. Alternatively or additionally, some or all pixels of the integrated device may include trenches for conductively coupling the power supply voltage to an edge of the pixel array where the pixels of the array may be connected to the power supply voltage.

FIG. 2-5A is a layout sketch of an example pixel 2-512a having discontinuous C/B regions that may be included in the arrays of FIGS. 2-1A, 2-1B, and 2-1C, according to some embodiments. Pixel 2-512a may be configured in the manner described herein for pixel 2-312 and/or any other pixel described herein. For example, pixel 2-512a is shown in FIG. 2-5A including photodetection region PPD, drain region D, charge storage region SD0, readout region FD, and transfer gates REJ, ST0, RST, RS, and SF. Also shown in FIG. 2-5A, pixel 2-512a includes barrier BPW, which may be configured to block incident charge carriers from reaching charge storage region SD0, as described further herein. Also shown in FIG. 2-5A, pixel 2-512a includes a p-doped well that may support some or all of the transistors having transfer gates RST, RS, SF, and TX0. In some embodiments, the p-well may be configured (e.g., expanded by doping a larger area of pixel 2-512a) to block incident charge carriers from reaching charge storage region SD0. Also shown in FIG. 2-5A, pixel 2-512a includes barriers DPI positioned between pixel 2-512a and adjacent pixels of the array including pixel 2-512a. For example, barriers DPI may be configured to block charge carriers from traveling between adjacent pixels of the array, as described further herein.

In some embodiments, some or all C/B regions may be discontinuous on at least one side of a pixel. For example, as shown in FIG. 2-5A, regions $C/B_1$ and $C/B_2$ of pixel 2-512a running parallel to the direction from photodetection region PPD to charge storage region SD0 are continuous and regions $C/B_4$ and $C/B_5$ running perpendicular to the direction of regions $C/B_1$ and $C/B_2$ are discontinuous, with gaps separating regions $C/B_4$ and $C/B_5$ from regions $C/B_1$ and $C/B_2$.

FIG. 2-5B is a layout sketch of an alternative example pixel 2-512b having discontinuous C/B regions that may be included in the arrays of FIGS. 2-1A, 2-1B, and 2-1C, according to some embodiments. Pixel 2-512b may be configured in the manner described herein for pixel 2-512a and/or any other pixel described herein. As shown in FIG. 2-5B, pixel 2-512b further includes an auxiliary gate REJ' coupled to drain region D. In some embodiments, auxiliary gate REJ' may be part of a diode-connected transistor connected between drain region D and a metal line configured to electrically couple drain region D to a power supply voltage. It should be appreciated that other pixels described herein may additionally include auxiliary gate REJ'.

Similar to pixel 2-512a shown in FIG. 2-5A, some C/B regions of pixel 2-512b are discontinuous. For example, shown in FIG. 2-5B, regions $C/B_1$ and $C/B_2$ of pixel 2-512b running parallel to the direction from photodetection region PPD to charge storage region SD0 are discontinuous and the regions $C/B_4$ and $C/B_5$ running perpendicular to the direction of regions $C/B_1$ and $C/B_2$ are continuous, with gaps separating regions $C/B_1$ and $C/B_2$ from regions $C/B_4$ and $C/B_5$. It should be appreciated that other pixels described herein may have discontinuous C/B regions as described herein for pixels 2-512a and 2-512b.

Also shown in FIG. 2-5B, pixel 2-512b region $C/B_3$ is positioned between photodetection region and charge storage region SD0 and terminates before drain region D. In some embodiments, region $C/B_3$ of other pixels described herein may be configured as shown in FIG. 2-5B for pixel 2-512b. In some embodiments, region $C/B_3$ may be omitted, such as shown in FIG. 2-2C.

FIG. 2-6A is a cross-sectional schematic view of an example pixel 2-612a that may be included in the arrays of FIG. 2-1A or 2-1B, according to some embodiments. In FIG. 2-6A, regions $C/B_3$-$C/B_5$, charge storage region SD0, readout region FD, and transfer gates TX0 and ST0 are positioned, in the first direction Dir1, after the shield portion of pixel 2-612a. In some embodiments, pixel 2-612a may have a thickness in the first direction Dir1 between the shield portion and transfer gates ST0 and TX0 of less than 10 microns, such as less than 6 microns, and/or between 3 and 6 microns.

In some embodiments, photodetection region PPD may include multiple sub-regions positioned after one another in the first direction Dir1. For example, in FIG. 2-6A, photodetection region PPD includes a first sub-region and a second sub-region positioned after the first sub-region in the first direction Dir1. The first sub-region extends, in the first direction Dir1, until the ends of regions $C/B_3$ and $C/B_4$. It should be appreciated that, in some embodiments, the first sub-region may end, in the first direction Dir1, before or after the ends of regions $C/B_3$ and $C/B_4$. In FIG. 2-6A, the C/B regions are elongated, in the first direction Dir1, alongside photodetection region PPD.

In some embodiments, regions $C/B_3$ and/or $C/B_4$ may be configured to induce a charge carrier depletion in the first sub-region of photodetection region PPD. For example, regions $C/B_3$ and/or $C/B_4$ may include charge layers configured to induce an intrinsic charge carrier depletion in the first sub-region. Alternatively or additionally, regions $C/B_3$ and/or $C/B_4$ may include metal regions configured to induce a charge carrier depletion in the first sub-region when a voltage bias is received at the metal regions. In some embodiments, transfer gate ST0 (and/or drain gate REJ, not shown in FIG. 2-6A) may be configured to induce a charge carrier depletion in the second sub-region when a control signal is received at the transfer gate. In some embodiments, the charge carrier depletion may facilitate propagation of charge carriers from photodetection region PPD toward charge storage region SD0.

In FIG. 2-6A, pixel 2-612a also includes barrier LPW, with readout region FD positioned, in the first direction Dirt, after barrier LPW, and barrier BPW, with charge storage region SD0 positioned, in the first direction Dir1, after barrier BPW. In some embodiments, barriers LPW and BPW may be configured to block charge carriers in pixel 2-612a from reaching readout region FD and charge storage region SD0, respectively, other than along transfer channels electrically coupling the regions to one another. In some embodiments, barriers LPW and BPW may be formed by doping regions of pixel 2-612a to have an opposite conductivity type from photodetection region PPD, charge storage region SD0, and readout region FD. For example, photodetection region PPD, charge storage region SD0, and readout region FD may be n-type doped, and barriers LPW and BPW may be p-type doped.

In FIG. 2-6A, pixel 2-612a also includes barriers DPI positioned between the C/B regions and other regions of pixel 2-612a, such as between region $C/B_4$ and photodetection region PPD, between region $C/B_3$ and photodetection region PPD, and between region $C/B_5$ and readout region FD. In some embodiments, barriers LPW and BPW may be formed by doping regions of pixel 2-612a to have an opposite conductivity type from photodetection region PPD, charge storage region SD0, and readout region FD.

Pixel 2-612a also includes a filter layer and an optical component. In some embodiments, the filter layer may be formed by doping a region of the pixel 2-612a before the shield in the first direction Dir1 with a same conductivity type as photodetection region PPD, charge storage region SD0, and readout region FD. In some embodiments, the optical component may be a microdisk. For example, the microdisk may be a dielectric structure configured to couple in florescence emission photons emitted by a sample and re-emit photons toward the photodetection region PPD. In some embodiments, the microdisk may efficiently couple photons incident along oblique directions with respect to the first direction Dirt and re-emit the photons toward the photodetection region PPD in the first direction Dir1.

In some embodiments, a pixel including C/B regions may be manufactured by forming C/B regions to induce a charge carrier depletion in the photodetection region. For example, one or more charge layers (e.g., metal-oxide compounds) may be deposited in the pixel to form the C/B regions. In some embodiments, an oxide layer may be deposited in the pixel, and the charge layer(s) may be deposited over the oxide layer. For example, the oxide layer may include silicon dioxide (SiO2). In some embodiments, after the charge layer(s) have been deposited over the oxide layer, additional oxide (e.g., $SiO_2$) may be deposited in the pixel. In some embodiments, metal-oxide compounds described herein may be deposited conformally, such as by conformal atomic layer deposition (ALD), and/or by chemical vapor deposition (CVD). For example, ALD of metal-oxide compounds described herein may have a thickness of 50 Angstroms, and CVD metal-oxide compounds described herein may have a thickness of 500 Angstroms. In some embodiments, prior to deposition, a masked etch may be performed to form at least one trench for deposition into the trench. It should be appreciated that any suitable charged materials (e.g., positively charged for depleting electrons) may be used to form the C/B regions for depleting photodetection region PPD, such as materials compatible with conformal deposition processes (e.g., ALD). As one example, such materials may be substantially or entirely free of electrons from atomic bonding and/or lattice sites, resulting in positive charge.

In some embodiments, one or more metal regions may be deposited in the pixel to form the C/B regions, with the one or more metal regions being configured for coupling to a voltage bias to induce the charge carrier depletion in the photodetection region. In some embodiments, barriers DPI may be formed by doping regions around the C/B regions to have an opposite conductivity type from the photodetection region. In some embodiments, the C/B regions may induce an intrinsic charge carrier depletion in the photodetection region (e.g., in the first sub-region) upon formation of the pixel (e.g., without applying an external electric field to the pixel). In some embodiments, C/B regions of some or all pixels in an integrated device may be formed simultaneously. For example, any or each of regions $C/B_1$, $C/B_2$, $C/B_3$, $C/B_4$, and/or $C/B_5$ may be formed during a same manufacturing step, such as a same conformal ALD and/or CVD step. In some embodiments, a sixth region $C/B_6$ may be formed during an ALD and/or CVD step preceding or following the step during which the other C/B regions are formed.

In some embodiments, the C/B regions may be formed from an opposite side of the integrated device, in the first direction Dir1, than the photodetection region, charge storage region(s), and/or readout region. For example, the photodetection region, charge storage region(s), and/or readout regions may be doped on a first face, in the first direction Dir1, of the integrated device, and the C/B/regions may be formed from (e.g., deposited from) a second face, in the first direction Dir1, of the integrated device.

FIG. 2-6B is a cross-sectional schematic view of an alternative example pixel 2-612b that may be included in the arrays of FIG. 2-1A or 2-1B, according to some embodiments. As shown in FIG. 2-6B, pixel 2-612b may be configured in the manner described herein for pixel 2-612a in connection with FIG. 2-6A, except pixel 2-612b may not include a filter. The inventors recognized that, in some embodiments, pixels described herein may not include a filter, such as when charge transfer occurs in the pixel at a fast enough rate.

FIG. 2-7A is a cross-sectional schematic view of an example pixel 2-712a that may be included in the arrays of FIG. 2-1A or 2-1B, according to some embodiments. In some embodiments, pixel 2-712a may be configured in the manner described herein for pixel 2-312. In FIG. 2-7A, photodetection region PPD extends between region $C/B_4$ to region $C/B_5$. For example, pixel 2-712a may not include region $C/B_3$. The inventors have recognized that positioning photodetection region PPD to extend between region $C/B_4$ to region $C/B_5$, and/or such that at least a portion of photodetection region PPD is positioned, in the first direction Dir1, before charge storage region SD0 and/or readout region FD, prevents incident photons and/or charge carriers from entering undesired portions of pixel 2-712a. For example, the incident photons and/or charge carriers may be transferred to the drain region D and/or to charge storage region SD0 via photodetection region PPD.

As shown in FIG. 2-7A, photodetection region PPD of pixel 2-712a includes first and second sub-regions, with the first sub-region extending, in the first direction Dirt, to the ends of regions $C/B_4$ and $C/B_5$ and/or to the barriers LPW and/or BPW. For example, the first sub-region may end, in the first direction Dir1, at a barrier or at the end of region $C/B_4$ or $C/B_5$, whichever the first sub-region reaches first. In FIG. 2-7A, regions $C/B_4$ and/or $C/B_5$ may be configured to induce a charge carrier depletion in the first sub-region as described herein in connection with FIG. 2-6A. In FIG. 2-7A, the C/B regions are elongated, in the first direction Dir1, alongside photodetection region PPD.

FIG. 2-7B is a cross-sectional schematic of a view of an alternative example pixel 2-712b that may be included in the array of FIG. 2-1A or 2-1B, according to some embodiments. As shown in FIG. 2-7B, pixel 2-712b may be configured in the manner described herein for pixel 2-712a in connection with FIG. 2-7A, except that pixel 2-712b may not include a filter, such as described herein for pixel 2-612b in connection with FIG. 2-6B.

FIG. 2-8 is a cross-sectional schematic view of an example pixel 2-812 that may be included in the array of FIG. 2-1A or 2-1B, according to some embodiments. As shown in FIG. 2-8, pixel 2-812 may be configured in the manner described herein for pixel 2-612a including in connection with FIG. 2-6A. Additionally, as shown in FIG. 2-8, barriers DPI may extend in the first direction Dir1 only part away along a depth of pixel 2-812. For example, barriers DPI may terminate alongside photodetection region PPD part-way through a depth of photodetection region PPD in the first direction Dir1.

FIG. 2-9 is a cross-sectional schematic view of pixel 2-112c shown in FIG. 2-2C, according to some embodiments. As shown in FIG. 2-9, pixel 2-112c may be configured in the manner described herein for pixel 2-712a including in connection with FIG. 2-7A, but with photodetection region PPD exposed through the shield portions on the side, in the first direction Dir1, that is configured to receive incident photons. It should be appreciated that some embodiments may include a filter as described herein for pixel 2-612a.

FIG. 2-10 is a cross-sectional schematic view of an example pixel 2-1012, which may be included in the array of FIG. 2-1C, according to some embodiments. As shown in FIG. 2-10, pixel 2-1012 may be configured in the manner described herein for pixel 2-112c including in connection with FIG. 2-9. As shown in FIG. 2-10, barriers DPI extend only part way through a depth of pixel 2-1012, as described herein for pixel 2-812 in connection with FIG. 2-8. Also shown in FIG. 2-10, the C/B regions of pixel 2-812 may extend, in the first direction Dir1, alongside photodetection region PPD from a first end of photodetection region PPD proximate the shield portions to a second end of photodetection region PPD proximate the transfer gates ST0 and TX0. In some embodiments, the C/B regions may terminate before a pinning layer of the photodetection region PPD at the second end. The inventors recognized that having the C/B regions extend from a first end of photodetection region PPD to a second end of photodetection region PPD provides greater optical and electrical isolation between adjacent pixels. In some embodiments, pixel 2-1012 may include a filter such as described herein for pixel 2-612a in connection with FIG. 2-6A.

FIG. 2-11 is a cross-sectional schematic view of an example pixel 2-1112 that may be included in the array of FIG. 2-1C, according to some embodiments. As shown in FIG. 2-11, pixel 2-1112 may be configured in the manner described herein for pixel 2-1012 including in connection with FIG. 2-10. In FIG. 2-11, pixel 2-1112 includes multiple barriers STI and DPI elongated, in the first direction Dir1, alongside the photodetection region PPD. For example, barriers DPI and the C/B regions may terminate, in the first direction Dir1, at barriers STI. In some embodiments, one set of tools may be used to form the C/B regions from the side of pixel 2-1112 configured to receive incident photons, and a different set of tools may be used to form barrier STI at the other side of pixel 2-1112 where the transfer gates are positioned.

It should be appreciated that techniques described herein in connection with pixels 2-112a and/or 2-112b may be used in embodiments of pixel 2-112c, and vice versa.

FIG. 2-13 is a layout sketch of an example pixel 2-1312 having multiple charge storage regions that may be included in the arrays of FIGS. 2-1A, 2-1B, and 2-1C, according to some embodiments. In some embodiments, pixel 2-1312 may be configured in the manner described herein for pixel 2-512a and/or any other pixel described herein. For example, in FIG. 2-13, regions $C/B_4$ and $C/B_5$ of pixel 2-1312 are shown discontinuous and regions $C/B_1$ and $C/B_2$ are shown continuous.

As shown in FIG. 2-13, pixel 2-1312 includes first and second charge storage regions SD0 and SD1, with second charge storage regions including sub-regions SD1-0 and SD1-1, and with transfer gate TX0 is positioned between first charge storage region SD0 and second charge storage region SD1. Also shown in FIG. 2-13, pixel 2-1312 includes transfer gate TX1 positioned between second charge storage region SD1 and readout region FD.

In some embodiments, charge storage region SD0 and sub-regions SD1-0 and SD1-1 of second charge storage region SD1 may have different electric potential levels. For example, charge storage region SD0 may have a first doping concentration, sub-region SD1-0 may have a second doping concentration higher than the first doping concentration, and sub-region SD1-1 may have a third doping concertation higher than the second doping concentration.

FIG. 2-14 is a diagram showing example charge transfer in pixel 2-1312, according to some embodiments. As shown in FIG. 2-14, operation of pixel 2-1312 may include multiple charge collection and transfer steps performed in time periods 2-1, 2-2, 2-3, 2-4, and 2-5.

In FIG. 2-14, operation of pixel 2-1312 may be cyclical. For example, as described further herein, each operation cycle may be performed during time periods 2-1 to 2-4, and pixel operation during time period 2-5 may be performed during time period 2-1 of a subsequent cycle (e.g., simultaneously with steps performed during time 2-1 of the subsequent cycle). 01701 In some embodiments, time period 2-1 may include one or more collection sequences such as described herein for time period 1-1 in connection with FIG. 1-4. For example, as shown in FIG. 2-14, charge carriers Q1 are received at charge storage region SD0 from photodetection region PPD during period 2-1. In some embodiments, the transfer channel electrically coupling charge storage region SD0 to charge storage region SD1 may be biased during time period 2-1 such that an intrinsic electric potential barrier prevents charge carriers from reaching charge storage region SD1.

In some embodiments, time period 2-2 may include one or more transfer sequences. For example, in FIG. 2-14, charge carriers Q1 are transferred from storage region SD0 to SD1 during time period 2-2. In some embodiments, the transfer channel electrically coupling photodetection region PPD to charge storage region SD0 may be biased during time period 2-2 such that charge carriers are not received in charge storage region SD0 from photodetection region PPD.

In some embodiments, time period 2-3 may include one or more readout sequences. For example, during each readout sequence, integrated device 1-102 may read out charge carriers from charge storage region SD1. For example, in FIG. 2-14, charge carriers Q1 are transferred from charge storage region SD1 to readout region FD during period 2-3. In some embodiments, time period 2-3 may also include one or more collection sequences performed in the manner described herein for time period 2-1. For example, In FIG. 2-14, charge carriers Q2 are received in charge storage region SD0 from photodetection region PPD during time period 2-3. In some embodiments, collection sequences performed during time period 2-3 may include collection periods that are offset in time with respect to the collection periods of time period 2-1. For example, the collection periods of time period 2-3 may be timed to capture charge carriers indicative of different characteristics (e.g., fluorescence lifetime) than the collection periods of time period 2-1.

In some embodiments, time period 2-4 may include one or more transfer sequences performed in the manner described herein for time period 2-2. For example, in FIG. 2-14, charge carriers Q2 are transferred from charge storage region SD0 to charge storage region SD1 during time period 2-4.

In some embodiments, time period 2-5 may include one or more readout sequences and one or more collection sequences performed in the manner described herein for time period 2-3. For example, in FIG. 2-14, charge carriers Q2 are transferred from charge storage region SD1 to readout region FD and charge carriers Q1' are received at charge storage region SD0 from photodetection region PPD during time period 2-5. In this example, receiving charge carriers Q1' also occurs during time period 2-1 of a subsequent cycle of operation, as time period 2-5 of the illustrated operation cycle overlaps, at least in part, with time period 2-1 of the subsequent cycle (e.g., when charge carriers Q2 are read out from the particular pixel).

It should be appreciated that, in some embodiments, operation of pixels described herein may include time periods between the time periods described herein and/or may omit certain time periods described herein. It should also be appreciated that, in some embodiments, operation of pixels described herein may not be cyclical, for example, by moving to a new time period (e.g., not any of time periods 2-1 through 2-5) after time period 2-5 is complete. In some embodiments, time periods described herein may occur in a different order than described herein.

IV. Intrinsic Electric Field Techniques

The inventors have also developed techniques for inducing intrinsic electric fields in a photodetection region of a pixel. In some embodiments, the photodetection region may be configured to induce an intrinsic electric field in a first direction (e.g., a direction from the sample well toward the photodetection region). For example, the photodetection region may be configured to induce an intrinsic electric field in a direction in which incident photons are received such that charge carriers generated in the photodetection region in response to the incident photons may be transferred quickly and efficiently in the first direction. In some embodiments, the photodetection region may include multiple layers positioned one after another in the first direction and having different intrinsic electric potential layers (e.g., due to having different dopant concentrations), thereby producing in an intrinsic electric field in the first direction.

In some embodiments, intrinsic electric fields may be combined with charge carrier depletion, each facilitating propagation of charge carriers from the photodetection region toward the charge storage region(s). It should be appreciated, however, that these techniques may be used alone or in any suitable combination, as embodiments described herein are not so limited.

In some embodiments, pixels described herein may include a photodetection region configured to induce an intrinsic electric field in the photodetection region in a first direction, as described further herein including with reference to FIG. 2-12. FIG. 2-12 is a cross-sectional schematic view of a portion of a pixel 2-1212 that may be included in the array of FIG. 2-1A, 2-1B, or 2-1C, according to some embodiments. In FIG. 2-12, the portion of pixel 2-1212 includes photodetection region PPD, charge storage region SD0, and transfer gate ST0. In some embodiments, photodetection region PPD includes multiple layers, such as Layers 1-3 indicated in FIG. 2-12, positioned one after another in the first direction Dir1. It should be appreciated that photodetection region PPD can have any number of layers, such as 4-10 layers or any number of layers therein, as suitable for the particular application.

In some embodiments, photodetection region PPD may be configured to induce an intrinsic electric field in the first direction Dir1. For example, the layers of photodetection region PPD may be configured to have different intrinsic electric potential levels, such that the difference between the electric potential levels induces an intrinsic electric field. In this example, Layer 2 may have a higher dopant concentration than Layer 1, and Layer 3 may have a higher dopant concentration than Layer 2. In some embodiments, photodetection region PPD may be n-type doped, and the intrinsic electric potential level of Layer 3 may be higher than the intrinsic electric potential level of Layer 2, and the intrinsic electric potential level of Layer 2 may be higher than the intrinsic electric potential level of Layer 1. As a result, photoelectrons generated in photodetection region PPD may be transferred more quickly and efficiently in the first direction Dir1. In some embodiments, photodetection region PPD may be p-type doped, and the intrinsic electric potential level of Layer 3 may be higher than the intrinsic electric potential level of Layer 2, and the intrinsic electric potential level of Layer 2 may be higher than the intrinsic electric potential level of Layer 1. As a result, photo-holes generated in photodetection region PPD may be transferred more quickly and efficiently in the first direction Dir1.

In some embodiments, layer within a first sub-region of photodetection region PPD may have different electric potential levels from layers within a second sub-region of photodetection region PPD. For example, layers of a second sub-region positioned, in the first direction Dir1, after a first sub-region may have a higher dopant concentration than layers of the first sub-region.

In some embodiments, photodetection region PPD may be manufactured by forming the layers of photodetection region PPD to have different intrinsic electric potential levels, such as by forming Layer 3 to have a higher dopant concentration than Layer 2, Layer 2 to have a higher dopant concentration than Layer 1, and so on. For example, each layer may be doped in a separate doping step, and/or some layers may be formed over multiple steps that at least partially overlap (e.g., such that some layers have higher dopant concentrations than other layers). It should be appreciated that, in some embodiments, layers of photodetection region PPD may be formed without photoresist-defined boundaries, such that the delineation between layers may be inferred by gradual rather than abrupt differences in dopant concentration.

V. Simulation Results

Some exemplary simulation results of pixels incorporating techniques described herein are presented below. It should be appreciated that the pixel configurations (e.g., doping concentrations) and simulated results for the exemplary pixels presented herein are not intended to be limiting, but rather to generally demonstrate the effectiveness of the techniques described herein in the context of a few exemplary pixels.

FIG. 3-1 is a perspective view of an exemplary pixel 3-112 that may be included in the integrated device 1-102, showing dopant concentration within the pixel 3-112, according to some embodiments. In some embodiments, pixel 3-112 may be configured in the manner described herein for pixel 2-112 and/or any other pixel described herein. For instance, in FIG. 3-1, pixel 3-112 includes photodetection region PPD, transfer gates ST0, TX0, REJ, and RS, and C/B regions, of which regions C/$B_1$ and C/$B_4$ are shown in FIG. 3-1. In FIG. 3-1, photodetection region PPD includes a first sub-region extending, in the first direction Dir1, from first ends of regions C/$B_1$ and C/$B_4$ past second ends of regions C/$B_1$ and C/$B_4$, and a second sub-region extending, in the first direction Dir1, from the first sub-region to drain region D and the transfer gates.

Figures 1, 2, 3, 4:
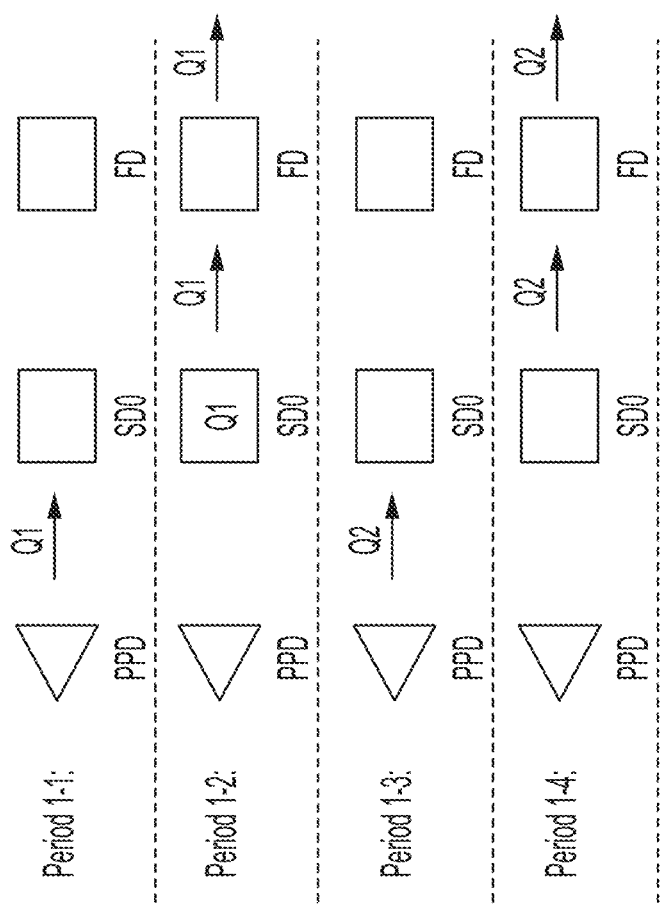

FIG. 3-2 is a side view of a cross-section of the pixel 3-112 showing dopant concentration within the pixel 3-112, according to some embodiments. FIG. 3-2 also indicates two sub-cross-sections of pixel 3-112 along the first direction Dir1, Slice1 and Slice2. Slice1 cuts through photodetection region PPD in the first direction Dir1. Slice2 cuts through region $C/B_4$ in the first direction Dir1. FIG. 3-3 is a graph 3-300 of total dopant concentration and n-type dopant concentration versus depth X in Slice1 of pixel 3-112 shown in FIG. 3-2, according to some embodiments. FIG. 3-4 is a graph 3-400 of p-type dopant concentration versus depth X in Slice2 of pixel 3-112 shown in FIG. 3-2, according to some embodiments. FIG. 3-2 also shows a region $C/B_6$ positioned, in the first direction Dir1, before photodetection region PPD. It should be appreciated that any pixels described herein may also include region $C/B_6$. In some embodiments, region $C/B_6$ may include a charge layer within an oxide layer. In FIG. 3-2, region $C/B_6$ is optically transparent. In some embodiments, region $C/B_6$ may not be completely optically transparent, as some optical loss and/or reflection may occur at region $C/B_6$.

As shown in FIGS. 3-2 and 3-3, photodetection region PPD extends, in the first direction Dir1, from X=6 microns to X=0 microns and regions $C/B_5$ and $C/B_4$ extend alongside photodetection region PPD, in the first direction Dir1, from X=6 microns to X=2 microns. The first sub-region extends, in the first direction Dir1, from X=6 microns to X=2.5 microns, and the second sub-region extends, in the first direction Dir1, from X=2.5 microns to X=0 microns. Drain gate REJ is positioned, in the first direction Dir1, after X=0 microns. It should be appreciated that, in some embodiments, the first sub-region may extend, in the first direction Dir1, from X=6 microns to X=2 microns, and the second sub-region may extend, in the first direction Dir1, from X=2 microns to X=0 microns.

As shown in FIG. 3-2, photodetection region PPD has multiple layers 1-5 having different dopant concentrations, with the dopant concentrations of the layers increasing from layer to layer in the first direction Dir1. For instance, layer 1 has a higher dopant concentration than layer 2, layer 2 has a higher dopant concentration than layer 3, layer 3 has a higher dopant concentration than layer 4, and layer 4 has a higher dopant concentration than layer 5. In FIG. 3-2, layers 3-5 are in the second sub-region of photodetection region PPD, and layers 1-2 are in the first and second sub-regions. In FIGS. 3-2 and 3-3, the dopant concentration of photodetection region PPD along Slice1 decreases from $1.3 \times 10^{18}$ total dopants per $cm^3$ ($1.1 \times 10^{17}$ n-type dopants per $cm^3$) to $1.6 \times 10^{14}$ total dopants per $cm^3$ ($0.9 \times 10^{13}$ n-type dopants per $cm^3$) between X=0.1 microns and X=4 microns. In some embodiments, the n-type dopants used may be arsenic. It should be appreciated that dopant concentrations described herein are exemplary and may vary according to the particular embodiment. For example, a larger pixel may be configured with a lower dopant concentration to obtain a charge carrier depletion as described herein at a particular bias voltage, whereas smaller pixels may be configured with higher dopant concentrations.

As shown in FIG. 3-4, the p-type dopant concentration along Slice2 is highest at X=0.6 microns, reaching about $3 \times 10^{20}$ dopants per $cm^3$. The dopant concentration along Slice2 is lower than $10^{14}$ dopants per $cm^3$ between X=2 microns and X=6 microns proximate region $C/B_4$. In some embodiments, the high p-type dopant concentration along Slice2 may isolate photodetection region PPD of pixel 3-112 from adjacent pixels. In some embodiments, the p-type dopants used may be boron.

FIG. 3-5A is a side view of a cross-section of pixel 3-112 showing charge carrier density within the pixel 3-112, according to some embodiments. Although region $C/B_6$ is not shown in FIG. 3-5A, region $C/B_6$ is still included in pixel 3-112. FIG. 3-5B is a side view of a cross-section of another pixel 3-112' showing charge carrier density within the pixel, according to some embodiments. Pixel 3-112' may be configured in the manner described herein for pixel 3-112, except that pixel 3-112' does not include C/B regions (although outlines of the C/B regions are shown in FIG. 3-5B, the illustrated regions are not charged or biased). FIGS. 3-5A and 3-5B each show the respective pixels 3-112 and 3-112' hundreds of nanoseconds after control signals have been applied to transfer gate REJ, thereby inducing at least a partial charge carrier depletion in at least part of the second sub-region of photodetection region PPD in each pixel.

As shown in FIG. 3-5A, photodetection region PPD of pixel 3-112 has fewer than $5 \times 10^3$ charge carriers per $cm^3$. For instance, photodetection region PPD of pixel 3-112 has fewer than $2 \times 10^{-6}$ charge carriers per $cm^3$ in the first sub-region, including fewer than $8 \times 10^{-14}$ charge carriers per $cm^3$ between X=5 microns and X=6 microns. In contrast, in FIG. 3-5B, photodetection region PPD of pixel 3-112' has greater than $1.5 \times 10^{12}$ charge carriers per $cm^3$ in photodetection region PPD, including greater than $10^{14}$ charge carriers per $cm^3$ throughout the portion of the first sub-region from X=3.7 microns to X=6 microns.

FIG. 3-6A is a graph 3-600a showing a number of charge carriers at different depths of pixels 3-112 and 3-112' over time, according to some embodiments. FIG. 3-6B is a magnified view of a portion 3-600b of the graph of FIGS. 3-6A, according to some embodiments. While some portions of FIGS. 3-6A to 3-6B purport to show fractions of a charge carrier in a region of photodetection region PPD, it should be appreciated that fractions of a charge carrier shown in the figures represent quantum mechanical probabilities of the presence of a charge carrier that are less than 1.

As shown in FIGS. 3-6A and 3-6B, pixel 3-112 has fewer than 10 charge carriers in the first sub-region and $8.25 \times 10^3$ charge carriers in the second sub-region at time 0, and pixel 3-112' has $1.15 \times 10^4$ charge carriers in the first sub-region and $9 \times 10^3$ charge carriers in the second sub-region at time 0. For instance, at time 0, substantially all of the charge carriers in the second sub-region of the photodetection region PPD of each pixel may be generated in response to incident photons, and substantially all of the charge carriers in the first sub-region of each pixel may be free charge carriers. In FIGS. 3-6A and 3-6B, pixel 3-112 has a same order of magnitude of charge carriers in the second sub-region as pixel 3-112', but pixel 3-112 has 4 orders of magnitude fewer charge carriers in the first sub-region than pixel 3-112'.

After $10^{-8}$ seconds, pixel 3-112 has $10^{-13}$ charge carriers in the first sub-region and fewer than $0.5 \times 10^3$ charge carriers in the second sub-region, and pixel 3-112' has $9.5 \times 10^3$ charge carriers in the first sub-region and $10^3$ charge carriers in the second sub-region. For instance, after $10^{-8}$ seconds, many charge carriers may have been transferred from photodetection region PPD to the drain region D and/or to charge storage regions. Since pixel 3-112 has fewer charge carriers in the first sub-region at time 0, charge carriers are transferred faster and more efficiently to drain and charge storage regions in pixel 3-112 than in pixel 3-112', leaving even fewer charge carriers in pixel 3-112 over time than in pixel 3-112'. Moreover, since pixel 3-112' has many more free charge carriers in the first sub-region at time 0, the free charge carriers may be transferred to charge storage regions as noise that pollutes the number of charge carriers generated in response to incident photons. Moreover, in some applications, excitation charge carriers generated in response to an excitation pulse may need to be transferred to the drain region within 1 nanosecond of the excitation pulse in order for fluorescence charge carriers generated following the excitation pulse to be quickly and efficiently transferred to the charge storage regions. Thus, pixel 3-112' may not be suitable for such applications because many excitation charge carriers remain in the pixel after 1 nanosecond has passed. It should be appreciated that the number of charge carriers at any given time within pixels described herein may vary according to the pixel configuration, mode of operation, and operating environment.

FIG. 3-7A is a side view of a cross-section of pixel 3-112 showing electric fields within the pixel 3-112, according to some embodiments. FIG. 3-7B is a side view of a cross-section of pixel 3-112' showing electric fields within the pixel 3-112', according to some embodiments. FIG. 3-8 is a graph 3-800 of electric field versus depth X for sub-cross-sections Slice1 and Slice1' of pixels 3-112 and 3-112', respectively, according to some embodiments.

As shown in FIGS. 3-7A and 3-7B, the photodetection regions PPD of pixels 3-112 and 3-112' have an electrical field between $4 \times 10^4$ V/cm and $4 \times 10^5$ V/cm between X=0 microns and X=0.1 microns as well as in the drain transfer channels between the photodetection regions PPD and drain regions D. In the sub-cross-sections represented in FIG. 3-8, each pixel has an electric field of $1.1 \times 10^5$ between X=0 microns and X=0.2 microns. In FIGS. 3-7A and 3-7B, pixel 3-112 has an electric field greater than $1.2 \times 10^4$ in photodetection region PPD at regions $C/B_5$ and $C/B_4$ from X=6 microns to X=2 microns, whereas pixel 3-112' has an electric field less than $1.2 \times 10^{-2}$ V/cm between X=6 microns and X=3.6 microns. Slice1 of pixel 3-112 represented in FIG. 3-8 has an electric field greater than $1.1 \times 10^3$ V/cm from X=0.5 microns to X=6 microns, including greater than $10^4$ at X=6 microns. Slice1' of pixel 3-112' represented in FIG. 3-8 has an electric field lower than $1.3 \times 10^3$ V/cm from X=0.5 microns to X=6 microns, including lower than $10^3$ V/cm from X=3 microns to X=6 microns, and lower than $10^2$ V/cm from X=3.6 microns to X=6 microns. The electric fields shown in photodetection region PPD of pixel 3-112 at regions $C/B_5$ and $C/B_4$ may deplete at least the first sub-region of photodetection region PPD of charge carriers, such as shown in FIG. 3-5A.

FIG. 3-9A is a graph 3-900a showing a number of charge carriers at different depths and in total within photodetection region PPD of pixel 3-112 over time, according to some embodiments. FIG. 3-9B is a magnified view of a portion 3-900b of the graph of FIG. 3-9A, according to some embodiments. FIG. 3-9C is a further magnified view of a portion 3-900c of the graph of FIG. 3-9B, according to some embodiments. In FIGS. 3-9A to 3-9C, the number of charge carriers is shown for the first and second sub-regions of photodetection region PPD and in total for photodetection region PPD. While some portions of FIGS. 3-9A to 3-9C purport to show fractions of a charge carrier in a region of photodetection region PPD, it should be appreciated that fractions of a charge carrier shown in the figures represent quantum mechanical probabilities of the presence of a charge carrier that are less than 1. As shown in FIGS. 3-9A to 3-9C, photodetection region PPD of pixel 3-112 has 0 charge carriers in total at time 0.

In some embodiments, during operation of pixel 3-112, charge carriers received at the first sub-region may be transferred to the drain region or charge storage region via the second sub-region of photodetection region PPD. At time $0.5 \times 10^{-10}$ seconds, photodetection region PPD has 0.8 total charge carriers, with 0.75 charge carriers in the first sub-region and 0.05 charge carriers in the second sub-region. At time $3.2 \times 10^{-10}$ seconds, photodetection region PPD has 0.4 total charge carriers, with 0.2 charge carriers in each of the first and second sub-regions. After $1.3 \times 10^{-9}$ seconds, the total number of charge carriers in photodetection region PPD asymptotically approaches $10^{-4}$, with more than an order of magnitude fewer charge carriers in the first sub-region than in the second sub-region after $1.5 \times 10^{-9}$ seconds. After $10^{-8}$ seconds, the ratio of charge carriers in the second sub-region versus in the first sub-region is greater than 8,000.

FIG. 3-10 is a graph 3-1000 showing a number of charge carriers over time for multiple pixels having different configurations, according to some embodiments. FIG. 3-10 shows a number of charge carriers of pixels having thicknesses of 3 microns, 4.5 microns, and 6 microns, in the first direction Dir1. For each thickness, the number of charge carriers is shown for a backside illuminated (BSI) pixel and a front-side illuminated (FSI) pixel having the given thickness. As described herein, a BSI pixel may be configured to receive incident photons in the first direction Dir1, and the charge storage regions and transfer gates of the BSI pixel may be positioned on an opposite side of the BSI pixel, in the first direction Dir1, from where incident photons are received. An FSI pixel may be configured to receive incident photons in the first direction Dir1, with the charge storage regions and transfer gates positioned on the same side of the FSI pixel, in the first direction Dir1, as where incident photons are received. As shown in FIG. 3-10, pixels having smaller thicknesses have fewer charge carriers, as smaller pixels have fewer free charge carriers by virtue of their smaller size. Also shown in FIG. 3-10, for FSI pixels and BSI pixels having the same thicknesses, FSI pixels have fewer charge carriers at least in part due to the charge storage regions and transfer gates of the FSI pixel being positioned at the side of the pixel that receives the incident photons, such that the charge carriers generated in the FSI pixel have a shorter travel distance to reach the charge storage regions.

FIG. 3-11A is a side view of a cross-section of a pixel 3-112, having a depth X of 6 microns, showing charge carrier density of the pixel 1 nanosecond after an excitation pulse, according to some embodiments. FIG. 3-11B is a side view of a cross-section of a pixel 3-112", having a depth X of 4.5 microns, showing charge carriers within the pixel 3-112" 1 nanosecond after an excitation pulse, according to some embodiments. Pixel 3-112" may be configured in the manner described herein for pixel 3-112, except for the difference in depth X.

1 nanosecond after an excitation pulse, pixel 3-112 may be transferring charge carriers generated in response to the excitation or resulting fluorescence emissions to the drain region or charge storage regions. As shown in FIG. 3-11A, some portions of photodetection region PPD of pixel 3-112 have greater than $1 \times 10^8$ charge carriers per $cm^3$, and substantially all of photodetection region PPD between X=6 microns and X=3.4 microns has greater than 30 charge carrier per $cm^3$. In contrast, after 1 nanosecond, pixel 3-112" may have transferred substantially all of the generated charge carriers to the drain or charge storage regions. In FIG. 3-11B, pixel 3-112" has fewer than 2 charge carriers per $cm^3$ from X=1.5 microns to X=4.5 microns. Because pixel 3-112" has a smaller depth X than pixel 3-112, pixel 3-112" has fewer free charge carriers and may have stronger electric fields that cause the transfer of charge carriers within photodetection region PPD to be faster and more efficient than in pixel 3-112.

FIG. 3-12A is a side view of the cross-section of pixel 3-112 showing electric fields within the pixel 3-112, according to some embodiments. FIG. 3-12B is a side view of the cross-section of pixel 3-112" showing electric fields within the pixel 3-112", according to some embodiments. FIG.

3-12B indicates a sub-cross-section Slice1' of pixel 3-112. FIG. 3-13 is a graph 3-1300 of electric field versus depth X for Slice1 of pixel 3-112 and Slice2 of pixel 3-112", respectively, according to some embodiments. As shown in FIGS. 3-12A, 3-12B, and 3-13, pixels 3-112 and 3-112" have substantially equal electric fields throughout the second sub-region in pixel 3-112 from X=0 microns to X=2.5 microns (corresponding to the second sub-region and much of the first sub-region of pixel 3-112"). In the first sub-region of pixel 3-112, between X=2.6 microns and X=4.5 microns, the electric fields in Slice1 of pixel 3-112 decrease to below $10^3$ V/cm, whereas the electric fields in Slice1' of pixel 3-112" only decrease to $1.2 \times 10^3$ V/cm before increasing above $10^4$ V/cm. The electric fields in Slice1 of pixel 3-112 increase above $10^4$ V/cm closer to X=6 microns. As a result of the smaller depth of pixel 3-112", the electric fields of pixel 3-112" do not dip as low as the electric fields of pixel 3-112 at depths greater than X=2.6 microns, thereby increasing the rate of charge transfer in pixel 3-112" as compared to pixel 3-112.

VI. Optical Rejection Techniques

The inventors have also developed techniques to direct, refract, and/or reflect incident photons and/or charge carriers toward the photodetection region of a pixel and/or away from the charge storage region(s) of the pixel. By directing, refracting, and/or reflecting photons and/or charge carriers toward the photodetection region, fewer incident photons and/or charge carriers may reach undesired portions of the pixel and/or adjacent pixels, such as charge storage regions, where the charge carriers and/or photons may add noise to the charge storage regions. Similarly, by directing, refracting, and/or reflecting incident photons and/or charge carriers away from the charge storage region(s) of the pixel, fewer noise photons and/or charge carriers may add noise to the charge storage region(s) of the pixel. In some embodiments, C/B regions of a pixel may be further configured to prevent incident photons and/or charge carriers from leaving the photodetection region and/or reaching the charge storage regions by paths other than via transfer gates, as described herein.

FIG. 4-1 is a side view of a cross-section of a pixel 4-112 incorporating optical rejection techniques that may be included in the integrated device 1-102, according to some embodiments. In some embodiments, pixel 4-112 may be configured in the manner described herein for any of pixels 1-112, 2-112, and 3-112. For instance, as shown in FIG. 4-1, pixel 4-112 includes photodetection region PPD, charge storage region SD0, and transfer gate ST0.

In some embodiments, pixel 4-112 may include one or more barriers. As shown in FIG. 4-1, pixel 4-112 includes a region C/B$_a$ positioned at a first end of photodetection region PPD and elongated parallel to the first direction Dir1. In some embodiments, region C/B$_a$ may be configured to block charge carriers. For example, in some embodiments, the first barrier region C/B$_a$ may be configured to block charge carriers in photodetection region PPD from reaching other portions of integrated device 1-102, such that the charge carriers may be transferred to drain region D or charge storage region SD0 as appropriate (e.g., depending on arrival time). In some embodiments, region C/B$_a$ may include a dielectric material (e.g., an oxide layer and/or oxide compound) with a charge layer. In some embodiments, a barrier including a doped region having an opposite conductivity type from photodetection region PPD and charge storage region SD0 may be disposed around at least a portion of region C/B$_a$. By blocking charge carriers at region C/B$_a$, pixel 4-112 may be configured to generate and transfer charge carriers to drain region D and/or charge storage region SD0 at a higher rate and with greater efficiency.

Also shown in FIG. 4-1, pixel 4-112 includes region C/B$_b$ positioned before charge storage region SD0 in the first direction Dir1. In some embodiments, region C/B$_b$ may be configured to block charge carriers from reaching charge storage region SD0. For example, in some embodiments, region C/B$_b$ may be configured to block charge carriers in photodetection region PPD or elsewhere in pixel 4-112 or integrated device 1-102 from reaching charge storage region SD0. In some embodiments, region C/B$_b$ may include a dielectric material and/or a doped region having a dopant concentration opposite that of photodetection region PPD and charge storage region SD0. By blocking charge carriers from reaching charge storage region SD0, fewer noise charge carriers may reach or be generated in charge storage region SD0, increasing the signal to noise ratio of charge carriers stored in charge storage region SD0.

Also shown in FIG. 4-1, pixel 4-112 includes a first metal layer positioned before region C/B$_a$ in the first direction Dir1 and a second metal layer positioned before region C/B$_b$ in the first direction Dir1. In some embodiments, the first layer may be configured to block incident photons from entering the interior of region C/B$_a$. In some embodiments, the second metal layer may be configured to block incident photons from entering the interior of region C/B$_b$ and/or from reaching charge storage region SD0.

FIG. 4-2 is a side view of a cross-section of an alternative pixel 4-212 incorporating optical rejection techniques that may be included in the integrated device 1-102, according to some embodiments. In some embodiments, pixel 4-212 may be configured in the manner described herein for pixel 4-112. In some embodiments, pixel 4-212 may include one or more metal barriers configured to block incident photons and/or charge carriers. In FIG. 4-2, pixel 4-212 includes a first metal barrier positioned at the first end of photodetection region PPD and elongated in the first direction Dir1. In some embodiments, the first metal barrier may be configured to reflect photons and/or charge carriers incident on the first metal barrier, such that the incident photons and/or charge carriers remain in photodetection region PPD. In some embodiments, the first metal barrier may be configured to induce a charge carrier depletion in photodetection region PPD and/or a photodetection region PPD of an adjacent pixel. For example, the first metal barrier may be configured to receive a voltage bias that induces the charge carrier depletion in the photodetection region PPD and/or a photodetection region of an adjacent pixel.

Also shown in FIG. 4-2, pixel 4-212 includes second metal barriers positioned at first and second ends of charge storage region SD0 and elongated in the first direction Dir1. In some embodiments, the second metal barriers may be configured to reflect photons and/or charge carriers incident on charge storage region SD0. In some embodiments, one or each second metal barrier may be configured to induce a charge carrier depletion in the photodetection region PPD of pixel 4-212 and/or of an adjacent pixel. In FIG. 4-2, the two second metal barriers are connected by a metal layer that may be configured in the manner described herein for the metal layer positioned, in the first direction Dir1, after the second barrier BPW in FIG. 4-1.

FIG. 4-3 is a side view of a cross-section of a further alternative pixel 4-312 incorporating optical rejection techniques that may be included in the integrated device 1-102, according to some embodiments. In some embodiments, pixel 4-312 may be configured in the manner described herein for pixel 4-212. In FIG. 4-3, photodetection region PPD of pixel 4-312 includes multiple layers, PD1 and PD2, with layer PD1 spaced from layer PD2 in the first direction Dir1. In some embodiments, layers PD1 and PD2 may have different intrinsic electric potential levels. For example, layer PD1 may have a higher dopant concentration than layer PD2.

In some embodiments, pixel 4-312 may also include an optically directive structure configured to direct incident photons toward photodetection region PPD. For example, the optically directive structure may be configured to refract photons incident on pixel 4-312 in oblique directions with respect to the first direction Dir1. In FIG. 4-3, pixel 4-312 includes an optically directive structure at a surface that is positioned before photodetection region PPD in the first direction Dir1, the optically directive structure including a plurality of openings positioned along the surface. In some embodiments, the openings may include a dielectric material such as air and/or oxide.

In FIG. 4-3, pixel 4-312 also includes regions $C/B_a$ and $C/B_b$, which may be configured in the manner described herein for the C/B regions shown in FIG. 4-1, including metal layers positioned before the C/B regions in the first direction Dir1.

VII. DNA and/or RNA Sequencing Applications

An analytic system described herein may include an integrated device and an instrument configured to interface with the integrated device. The integrated device may include an array of pixels, where a pixel includes a reaction chamber and at least one photodetector. A surface of the integrated device may have a plurality of reaction chambers, where a reaction chamber is configured to receive a sample from a suspension placed on the surface of the integrated device. A suspension may contain multiple samples of a same type, and in some embodiments, different types of samples. In this regard, the phrase "sample of interest" as used herein can refer to a plurality of samples of a same type that are dispersed in a suspension, for example. Similarly, the phrase "molecule of interest" as used herein can refer to a plurality of molecules of a same type that are dispersed in a suspension. The plurality of reaction chambers may have a suitable size and shape such that at least a portion of the reaction chambers receive one sample from a suspension. In some embodiments, the number of samples within a reaction chamber may be distributed among the reaction chambers such that some reaction chambers contain one sample with others contain zero, two or more samples.

In some embodiments, a suspension may contain multiple single-stranded DNA templates, and individual reaction chambers on a surface of an integrated device may be sized and shaped to receive a sequencing template. Sequencing templates may be distributed among the reaction chambers of the integrated device such that at least a portion of the reaction chambers of the integrated device contain a sequencing template. The suspension may also contain labeled nucleotides which then enter in the reaction chamber and may allow for identification of a nucleotide as it is incorporated into a strand of DNA complementary to the single-stranded DNA template in the reaction chamber. In some embodiments, the suspension may contain sequencing templates and labeled nucleotides may be subsequently introduced to a reaction chamber as nucleotides are incorporated into a complementary strand within the reaction chamber. In this manner, timing of incorporation of nucleotides may be controlled by when labeled nucleotides are introduced to the reaction chambers of an integrated device.

Excitation light is provided from an excitation source located separate from the pixel array of the integrated device. The excitation light is directed at least in part by elements of the integrated device towards one or more pixels to illuminate an illumination region within the reaction chamber. A marker may then emit emission light when located within the illumination region and in response to being illuminated by excitation light. In some embodiments, one or more excitation sources are part of the instrument of the system where components of the instrument and the integrated device are configured to direct the excitation light towards one or more pixels.

Emission light emitted from a reaction chamber (e.g., by a fluorescent label) may then be detected by one or more photodetectors within a pixel of the integrated device. Characteristics of the detected emission light may provide an indication for identifying the marker associated with the emission light. Such characteristics may include any suitable type of characteristic, including an arrival time of photons detected by a photodetector, an amount of photons accumulated over time by a photodetector, and/or a distribution of photons across two or more photodetectors. In some embodiments, a photodetector may have a configuration that allows for the detection of one or more timing characteristics associated with emission light (e.g., fluorescence lifetime). The photodetector may detect a distribution of photon arrival times after a pulse of excitation light propagates through the integrated device, and the distribution of arrival times may provide an indication of a timing characteristic of the emission light (e.g., a proxy for fluorescence lifetime). In some embodiments, the one or more photodetectors provide an indication of the probability of emission light emitted by the marker (e.g., fluorescence intensity). In some embodiments, a plurality of photodetectors may be sized and arranged to capture a spatial distribution of the emission light. Output signals from the one or more photodetectors may then be used to distinguish a marker from among a plurality of markers, where the plurality of markers may be used to identify a sample or its structure. In some embodiments, a sample may be excited by multiple excitation energies, and emission light and/or timing characteristics of the emission light from the reaction chamber in response to the multiple excitation energies may distinguish a marker from a plurality of markers.

Figures 2, 3, 4, 5, 5A:
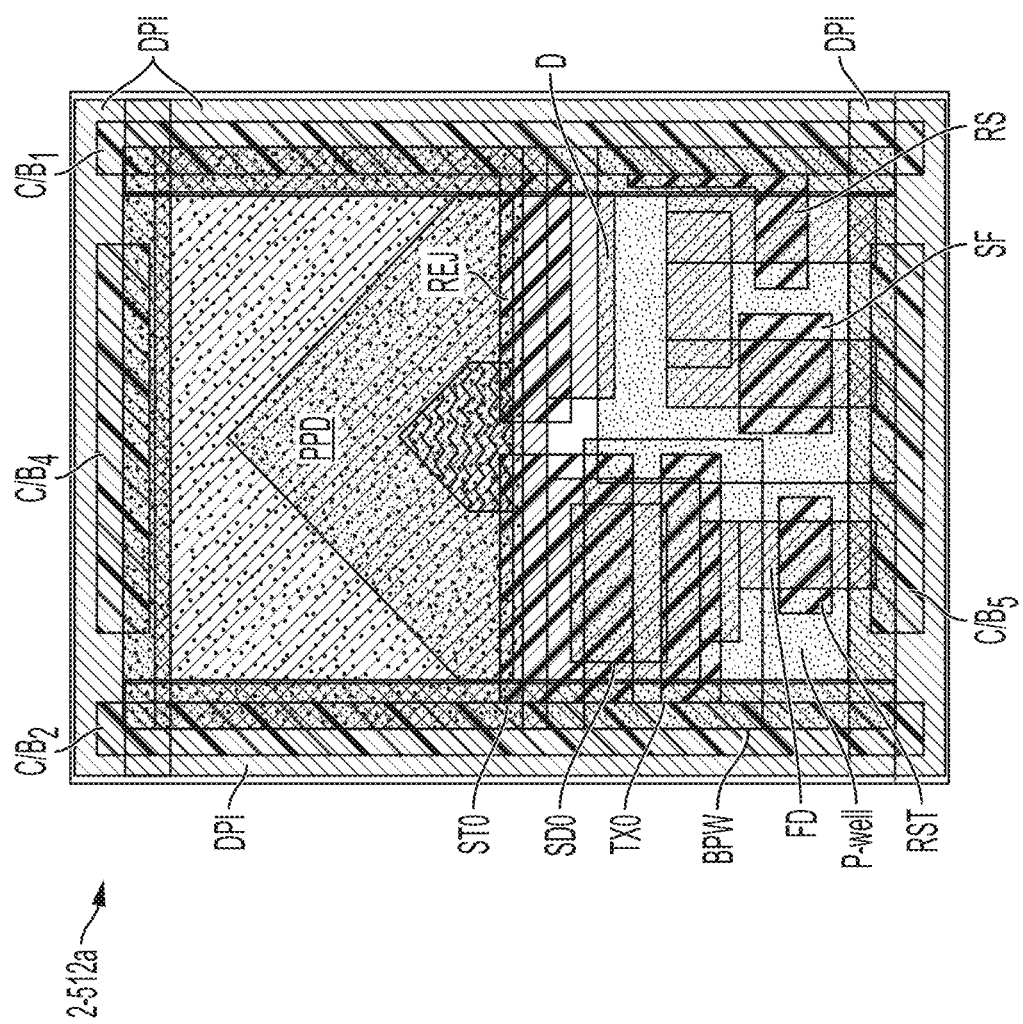
Figures 2, 3, 4, 5, 5B:
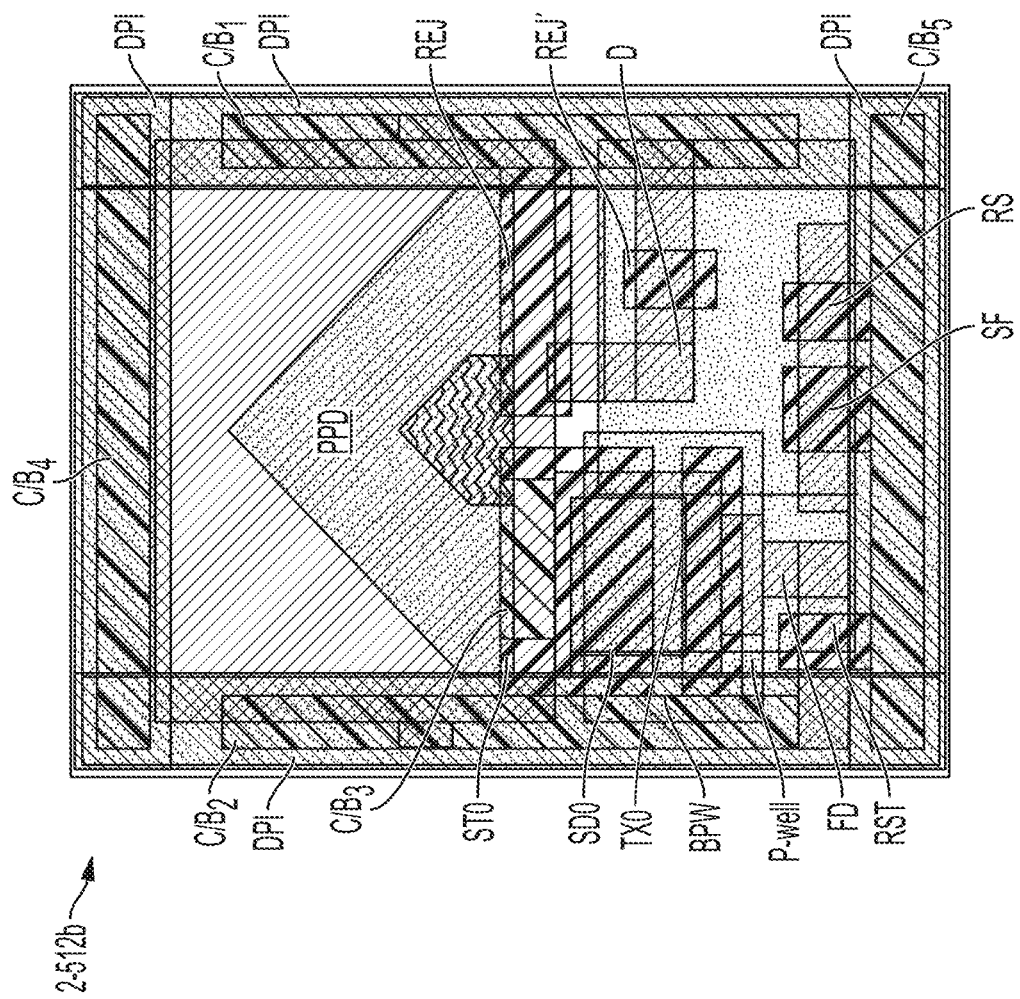

A schematic overview of the system 5-100 is illustrated in FIG. 5-1A. The system comprises an integrated device 5-102 that interfaces with an instrument 5-104. It should be appreciated that any or all integrated devices described herein may be used in place of or or in addition to integrated device 5-102. In some embodiments, instrument 5-104 may include one or more excitation sources 5-106 integrated as part of instrument 5-104. In some embodiments, an excitation source may be external to both instrument 5-104 and integrated device 5-102, and instrument 5-104 may be configured to receive excitation light from the excitation source and direct excitation light to the integrated device. The integrated device may interface with the instrument using any suitable socket for receiving the integrated device and holding it in precise optical alignment with the excitation source. The excitation source 5-106 may be configured to provide excitation light to the integrated device 5-102. As illustrated schematically in FIG. 5-1A, the integrated device 5-102 has a plurality of pixels 5-112, where at least a portion of pixels may perform independent analysis of a sample of interest. Such pixels 5-112 may be referred to as "passive source pixels" since a pixel receives excitation light from a source 5-106 separate from the pixel, where excitation light from the source excites some or all of the pixels 5-112. Excitation source 5-106 may be any suitable light source. Examples of suitable excitation sources are described in U.S. patent application Ser. No. 14/821,688, filed Aug. 7, 2015, titled "INTEGRATED DEVICE FOR PROBING, DETECTING AND ANALYZING MOLECULES," which is incorporated by reference in its entirety. In some embodiments, excitation source 5-106 includes multiple excitation sources that are combined to deliver excitation light to integrated device 5-102. The multiple excitation sources may be configured to produce multiple excitation energies or wavelengths.

A pixel 5-112 has a reaction chamber 5-108 configured to receive a single sample of interest and a photodetector 5-110 for detecting emission light emitted from the reaction chamber in response to illuminating the sample and at least a portion of the reaction chamber 5-108 with excitation light provided by the excitation source 5-106. In some embodiments, reaction chamber 5-108 may retain the sample in proximity to a surface of integrated device 5-102, which may ease delivery of excitation light to the sample and detection of emission light from the sample or a reaction component (e.g., a labeled nucleotide).

Optical elements for coupling excitation light from excitation light source 5-106 to integrated device 5-102 and guiding excitation light to the reaction chamber 5-108 are located both on integrated device 5-102 and the instrument 5-104. Source-to-chamber optical elements may comprise one or more grating couplers located on integrated device 5-102 to couple excitation light to the integrated device and waveguides to deliver excitation light from instrument 5-104 to reaction chambers in pixels 5-112. One or more optical splitter elements may be positioned between a grating coupler and the waveguides. The optical splitter may couple excitation light from the grating coupler and deliver excitation light to at least one of the waveguides. In some embodiments, the optical splitter may have a configuration that allows for delivery of excitation light to be substantially uniform across all the waveguides such that each of the waveguides receives a substantially similar amount of excitation light. Such embodiments may improve performance of the integrated device by improving the uniformity of excitation light received by reaction chambers of the integrated device.

Reaction chamber 5-108, a portion of the excitation source-to-chamber optics, and the reaction chamber-to-photodetector optics are located on integrated device 5-102. Excitation source 5-106 and a portion of the source-to-chamber components are located in instrument 5-104. In some embodiments, a single component may play a role in both coupling excitation light to reaction chamber 5-108 and delivering emission light from reaction chamber 5-108 to photodetector 5-110. Examples of suitable components, for coupling excitation light to a reaction chamber and/or directing emission light to a photodetector, to include in an integrated device are described in U.S. patent application Ser. No. 14/821,688, filed Aug. 7, 2015, titled "INTEGRATED DEVICE FOR PROBING, DETECTING AND ANALYZING MOLECULES," and U.S. patent application Ser. No. 14/543,865, filed Nov. 17, 2014, titled "INTEGRATED DEVICE WITH EXTERNAL LIGHT SOURCE FOR PROBING, DETECTING, AND ANALYZING MOLECULES," both of which are incorporated by reference in their entirety.

Pixel 5-112 is associated with its own individual reaction chamber 5-108 and at least one photodetector 5-110. The plurality of pixels of integrated device 5-102 may be arranged to have any suitable shape, size, and/or dimensions. Integrated device 5-102 may have any suitable number of pixels. The number of pixels in integrated device 5-102 may be in the range of approximately 10,000 pixels to 1,000,000 pixels or any value or range of values within that range. In some embodiments, the pixels may be arranged in an array of 512 pixels by 512 pixels. Integrated device 5-102 may interface with instrument 5-104 in any suitable manner. In some embodiments, instrument 5-104 may have an interface that detachably couples to integrated device 5-102 such that a user may attach integrated device 5-102 to instrument 5-104 for use of integrated device 5-102 to analyze at least one sample of interest in a suspension and remove integrated device 5-102 from instrument 5-104 to allow for another integrated device to be attached. The interface of instrument 5-104 may position integrated device 5-102 to couple with circuitry of instrument 5-104 to allow for readout signals from one or more photodetectors to be transmitted to instrument 5-104. Integrated device 5-102 and instrument 5-104 may include multi-channel, high-speed communication links for handling data associated with large pixel arrays (e.g., more than 10,000 pixels).

A cross-sectional schematic of integrated device 5-102 illustrating a row of pixels 5-112 is shown in FIG. 5-1B. Integrated device 5-102 may include coupling region 5-201, routing region 5-202, and pixel region 5-203. Pixel region 5-203 may include a plurality of pixels 5-112 having reaction chambers 5-108 positioned on a surface at a location separate from coupling region 5-201, which is where excitation light (shown as the dashed arrow) couples to integrated device 5-102. Reaction chambers 5-108 may be formed through metal layer(s) 5-116. One pixel 5-112, illustrated by the dotted rectangle, is a region of integrated device 5-102 that includes a reaction chamber 5-108 and a photodetection region having one or more photodetectors 5-110.

FIG. 5-1B illustrates the path of excitation (shown in dashed lines) by coupling a beam of excitation light to coupling region 5-201 and to reaction chambers 5-108. The row of reaction chambers 5-108 shown in FIG. 5-1B may be positioned to optically couple with waveguide 5-220. Excitation light may illuminate a sample located within a reaction chamber. The sample or a reaction component (e.g., fluorescent label) may reach an excited state in response to being illuminated by the excitation light. When in an excited state, the sample or reaction component may emit emission light, which may be detected by one or more photodetectors associated with the reaction chamber. FIG. 5-1B schematically illustrates the path of emission light (shown as the solid line) from a reaction chamber 5-108 to photodetector(s) 5-110 of pixel 5-112. The photodetector(s) 5-110 of pixel 5-112 may be configured and positioned to detect emission light from reaction chamber 5-108. Examples of suitable photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated by reference in its entirety. For an individual pixel 5-112, a reaction chamber 5-108 and its respective photodetector(s) 5-110 may be aligned along a common axis (along the y-direction shown in FIG. 5-1B). In this manner, the photodetector(s) may overlap with the reaction chamber within a pixel 5-112.

The directionality of the emission light from a reaction chamber 5-108 may depend on the positioning of the sample in the reaction chamber 5-108 relative to metal layer(s) 5-116 because metal layer(s) 5-116 may act to reflect emission light. In this manner, a distance between metal layer(s) 5-116 and a fluorescent marker positioned in a reaction chamber 5-108 may impact the efficiency of photodetector(s) 5-110, that are in the same pixel as the reaction chamber, to detect the light emitted by the fluorescent marker. The distance between metal layer(s) 5-116 and the bottom surface of a reaction chamber 5-108, which is proximate to where a sample may be positioned during operation, may be in the range of 100 nm to 500 nm, or any value or range of values in that range. In some embodiments the distance between metal layer(s) 5-116 and the bottom surface of a reaction chamber 5-108 is approximately 300 nm.

The distance between the sample and the photodetector(s) may also impact efficiency in detecting emission light. By decreasing the distance light has to travel between the sample and the photodetector(s), detection efficiency of emission light may be improved. In addition, smaller distances between the sample and the photodetector(s) may allow for pixels that occupy a smaller area footprint of the integrated device, which can allow for a higher number of pixels to be included in the integrated device. The distance between the bottom surface of a reaction chamber 5-108 and photodetector(s) may be in the range of 1 µm to 15 µm, or any value or range of values in that range.

Photonic structure(s) 5-230 may be positioned between reaction chambers 5-108 and photodetectors 5-110 and configured to reduce or prevent excitation light from reaching photodetectors 5-110, which may otherwise contribute to signal noise in detecting emission light. As shown in FIG. 5-1B, the one or more photonic structures 5-230 may be positioned between waveguide 5-220 and photodetectors 5-110. Photonic structure(s) 5-230 may include one or more optical rejection photonic structures including a spectral filter, a polarization filter, and a spatial filter. Photonic structure(s) 5-230 may be positioned to align with individual reaction chambers 5-108 and their respective photodetector(s) 5-110 along a common axis. Metal layers 5-240, which may act as a circuitry for integrated device 5-102, may also act as a spatial filter, in accordance with some embodiments. In such embodiments, one or more metal layers 5-240 may be positioned to block some or all excitation light from reaching photodetector(s) 5-110.

Coupling region 5-201 may include one or more optical components configured to couple excitation light from an external excitation source. Coupling region 5-201 may include grating coupler 5-216 positioned to receive some or all of a beam of excitation light. Examples of suitable grating couplers are described in U.S. patent application Ser. No. 15/844,403, filed Dec. 15, 2017, titled "OPTICAL COUPLER AND WAVEGUIDE SYSTEM," which is incorporated by reference in its entirety. Grating coupler 5-216 may couple excitation light to waveguide 5-220, which may be configured to propagate excitation light to the proximity of one or more reaction chambers 5-108. Alternatively, coupling region 5-201 may comprise other well-known structures for coupling light into a waveguide.

Components located off of the integrated device may be used to position and align the excitation source 5-106 to the integrated device. Such components may include optical components including lenses, mirrors, prisms, windows, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. patent application Ser. No. 15/161,088, filed May 20, 2016, titled "PULSED LASER AND SYSTEM," which is incorporated by reference in its entirety. Another example of a beam-steering module is described in U.S. patent application Ser. No. 15/842,720, filed Dec. 14, 2017, titled "COMPACT BEAM SHAPING AND STEERING ASSEMBLY," which is incorporated herein by reference.

A sample to be analyzed may be introduced into reaction chamber 5-108 of pixel 5-112. The sample may be a biological sample or any other suitable sample, such as a chemical sample. In some cases, the suspension may include multiple molecules of interest and the reaction chamber may be configured to isolate a single molecule. In some instances, the dimensions of the reaction chamber may act to confine a single molecule within the reaction chamber, allowing measurements to be performed on the single molecule. Excitation light may be delivered into the reaction chamber 5-108, so as to excite the sample or at least one fluorescent marker attached to the sample or otherwise associated with the sample while it is within an illumination area within the reaction chamber 5-108.

In operation, parallel analyses of samples within the reaction chambers are carried out by exciting some or all of the samples within the reaction chambers using excitation light and detecting signals with the photodetectors that are representative of emission light from the reaction chambers. Emission light from a sample or reaction component (e.g., fluorescent label) may be detected by a corresponding photodetector and converted to at least one electrical signal. The electrical signals may be transmitted along conducting lines (e.g., metal layers 5-240) in the circuitry of the integrated device, which may be connected to an instrument interfaced with the integrated device. The electrical signals may be subsequently processed and/or analyzed. Processing or analyzing of electrical signals may occur on a suitable computing device either located on or off the instrument.

Instrument 5-104 may include a user interface for controlling operation of instrument 5-104 and/or integrated device 5-102. The user interface may be configured to allow a user to input information into the instrument, such as commands and/or settings used to control the functioning of the instrument. In some embodiments, the user interface may include buttons, switches, dials, and a microphone for voice commands. The user interface may allow a user to receive feedback on the performance of the instrument and/or integrated device, such as proper alignment and/or information obtained by readout signals from the photodetectors on the integrated device. In some embodiments, the user interface may provide feedback using a speaker to provide audible feedback. In some embodiments, the user interface may include indicator lights and/or a display screen for providing visual feedback to a user.

In some embodiments, instrument 5-104 may include a computer interface configured to connect with a computing device. Computer interface may be a USB interface, a FireWire interface, or any other suitable computer interface. Computing device may be any general purpose computer, such as a laptop or desktop computer. In some embodiments, computing device may be a server (e.g., cloud-based server) accessible over a wireless network via a suitable computer interface. The computer interface may facilitate communication of information between instrument 5-104 and the computing device. Input information for controlling and/or configuring the instrument 5-104 may be provided to the computing device and transmitted to instrument 5-104 via the computer interface. Output information generated by instrument 5-104 may be received by the computing device via the computer interface. Output information may include feedback about performance of instrument 5-104, performance of integrated device 5-102, and/or data generated from the readout signals of photodetector 5-110.

In some embodiments, instrument 5-104 may include a processing device configured to analyze data received from one or more photodetectors of integrated device 5-102 and/or transmit control signals to excitation source(s) 5-106. In some embodiments, the processing device may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from one or more photodetectors may be performed by both a processing device of instrument 5-104 and an external computing device. In other embodiments, an external computing device may be omitted and processing of data from one or more photodetectors may be performed solely by a processing device of integrated device 5-102.

Referring to FIG. 5-1C, a portable, advanced analytic instrument 5-100 can comprise one or more pulsed optical sources 5-106 mounted as a replaceable module within, or otherwise coupled to, the instrument 5-100. The portable analytic instrument 5-100 can include an optical coupling system 5-115 and an analytic system 5-160. The optical coupling system 5-115 can include some combination of optical components (which may include, for example, none, one from among, or more than one component from among the following components: lens, mirror, optical filter, attenuator, beam-steering component, beam shaping component) and be configured to operate on and/or couple output optical pulses 5-122 from the pulsed optical source 5-106 to the analytic system 5-160. The analytic system 5-160 can include a plurality of components that are arranged to direct the optical pulses to at least one reaction chamber for sample analysis, receive one or more optical signals (e.g., fluorescence, backscattered radiation) from the at least one reaction chamber, and produce one or more electrical signals representative of the received optical signals. In some embodiments, the analytic system 5-160 can include one or more photodetectors and may also include signal-processing electronics (e.g., one or more microcontrollers, one or more field-programmable gate arrays, one or more microprocessors, one or more digital signal processors, logic gates, etc.) configured to process the electrical signals from the photodetectors. The analytic system 5-160 can also include data transmission hardware configured to transmit and receive data to and from external devices (e.g., one or more external devices on a network to which the instrument 5-100 can connect via one or more data communications links). In some embodiments, the analytic system 5-160 can be configured to receive a bio-optoelectronic chip 5-140, which holds one or more samples to be analyzed.

Figures 1A, 5:
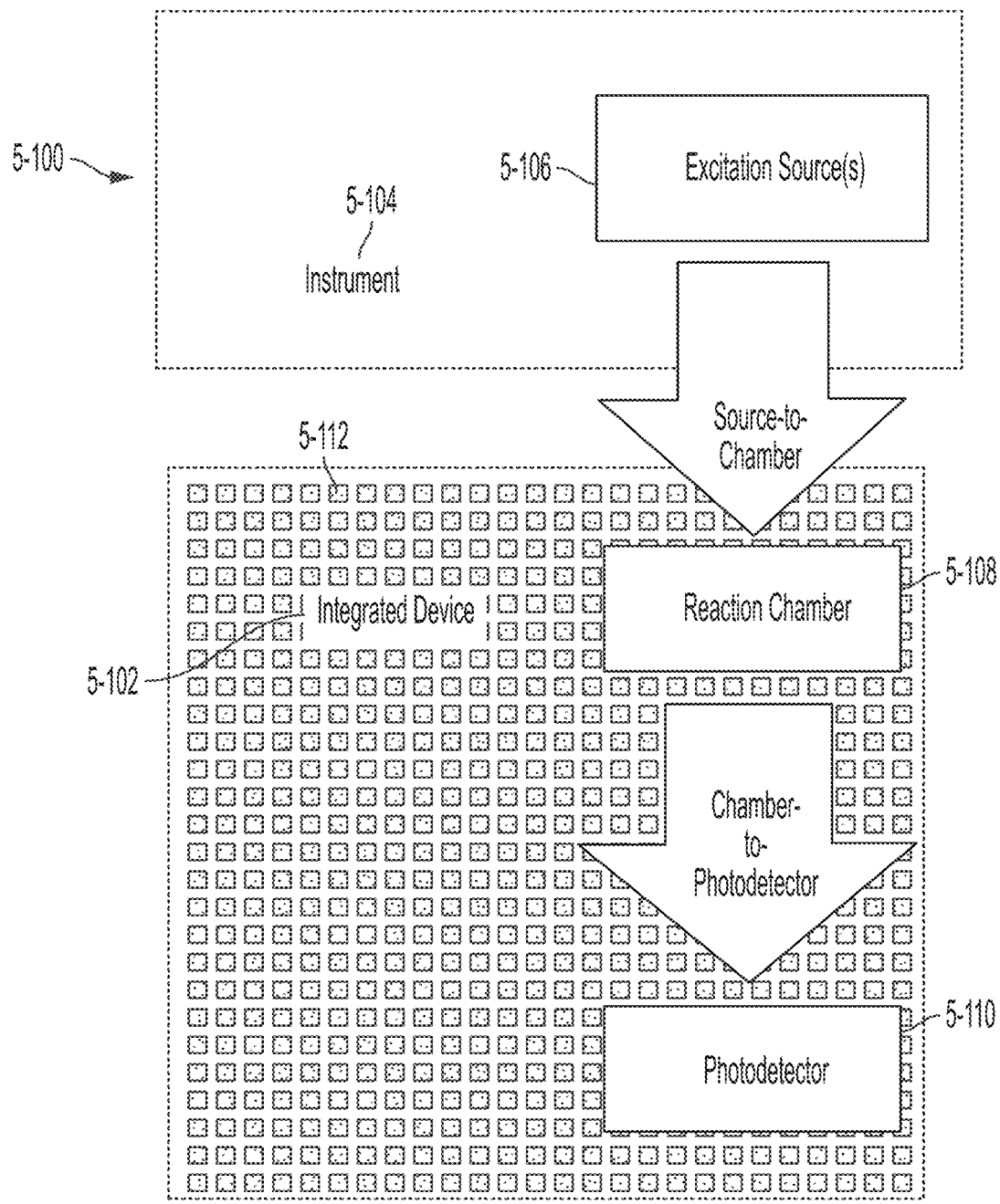
Figures 1B, 5:
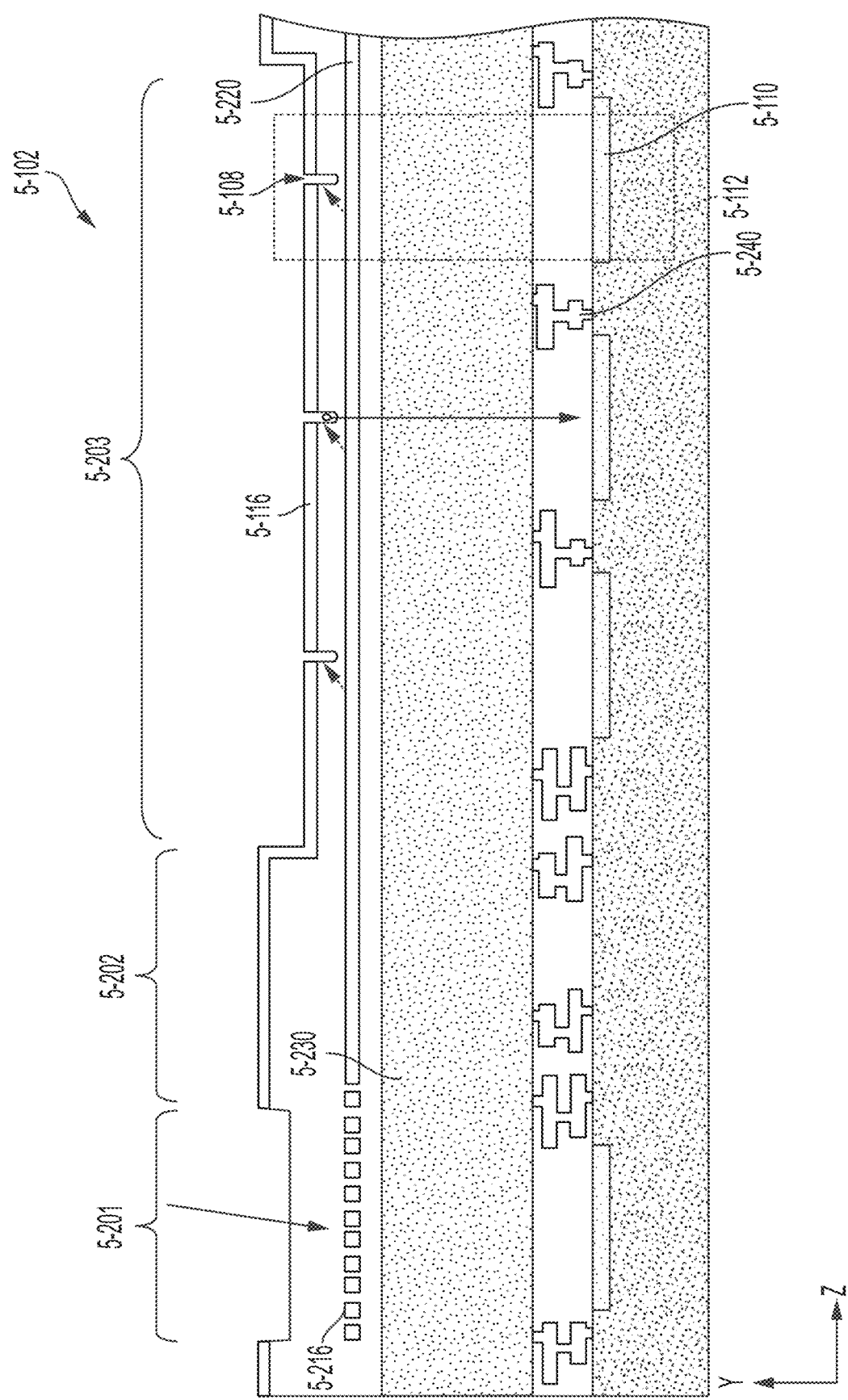
Figures 1C, 5:
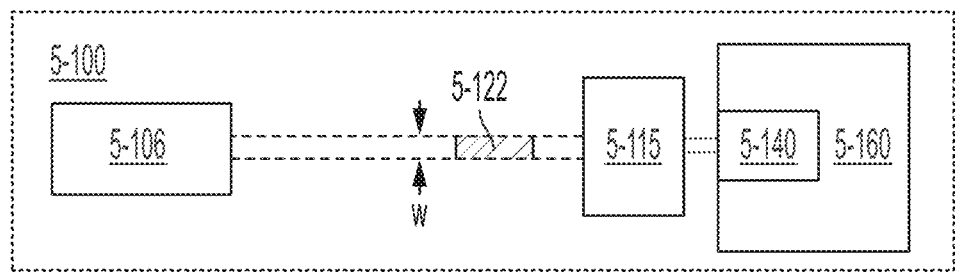
Figures 1D, 5:
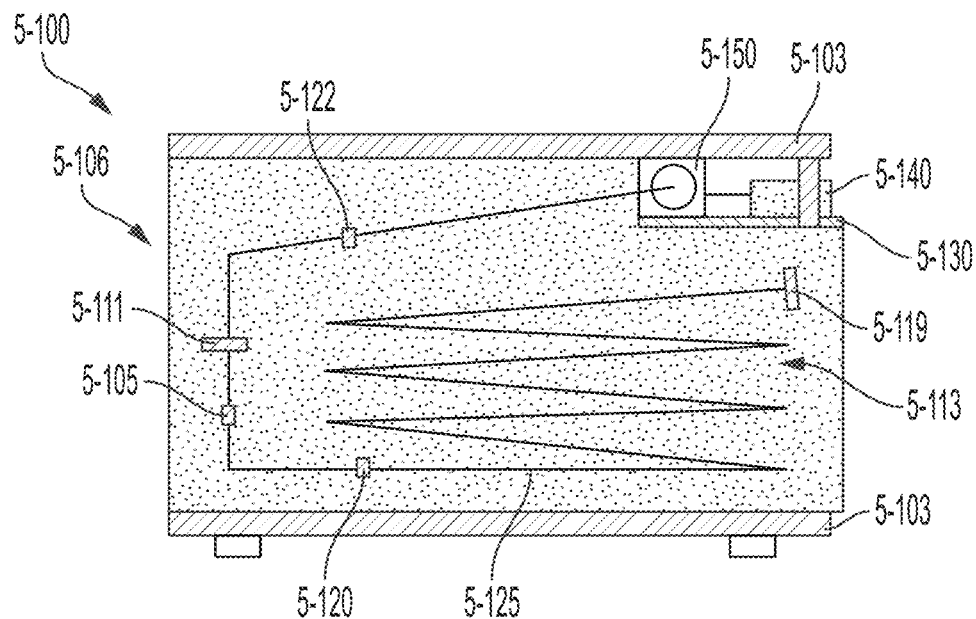
Figures 2, 5:
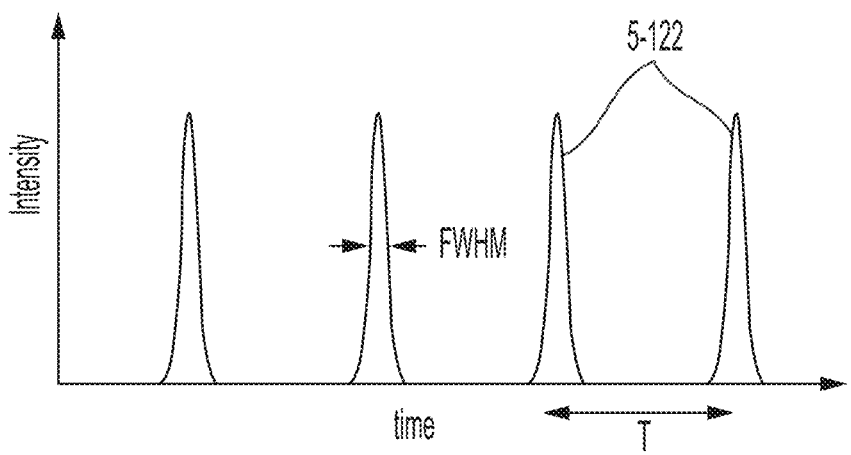
Figures 3, 5:
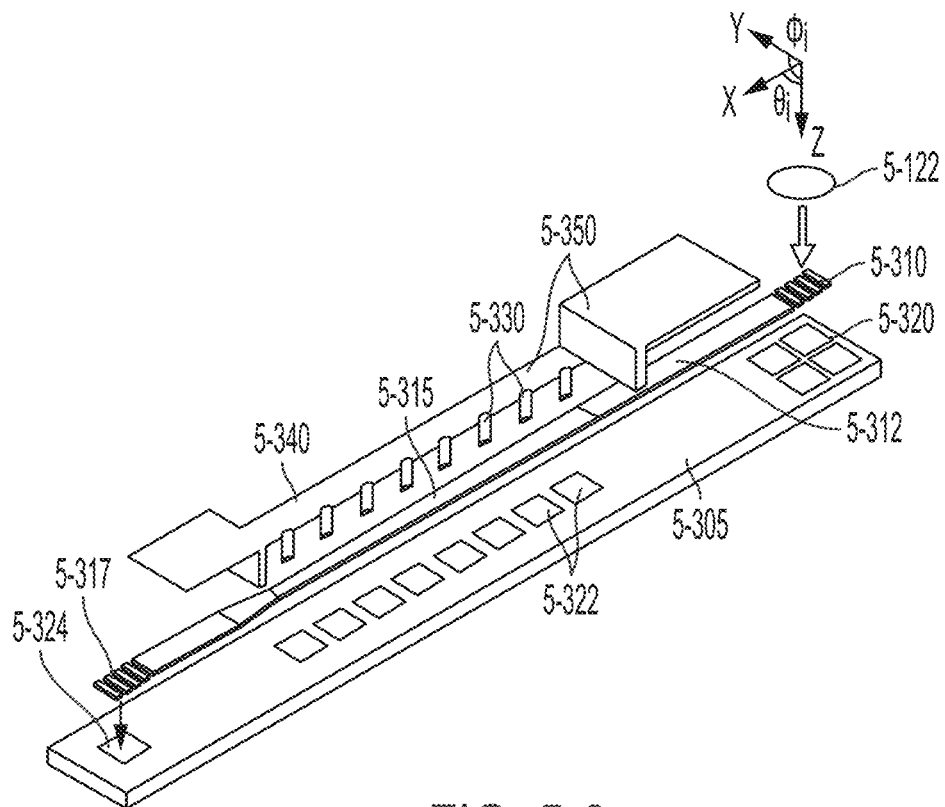
Figures 4, 5:
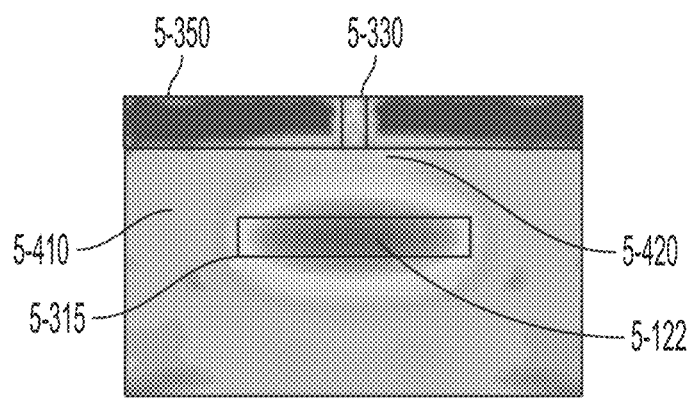
Figure 5:
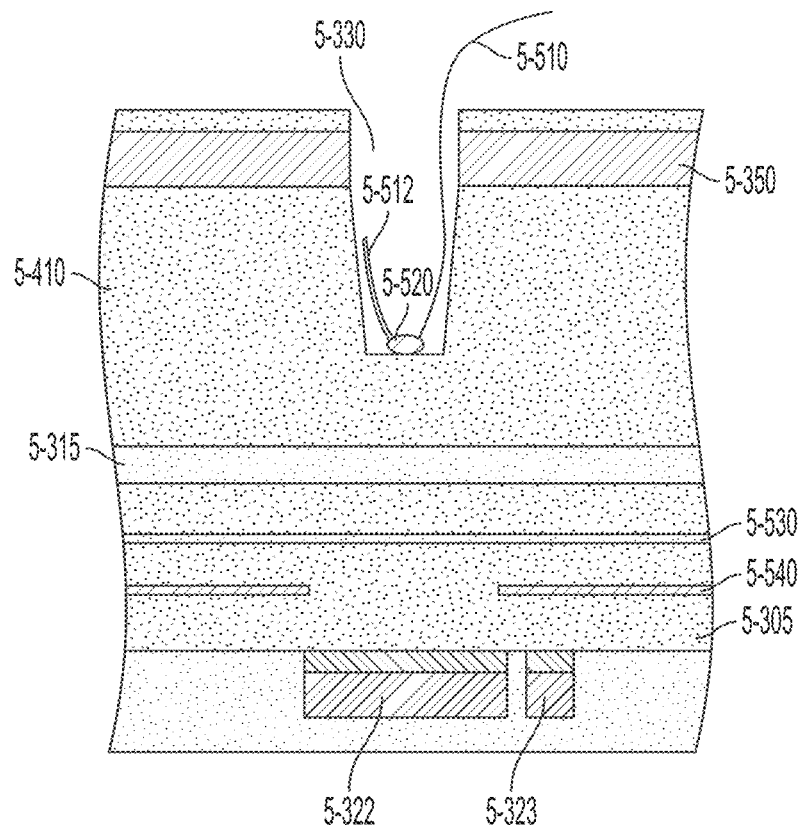
Figures 5, 6:
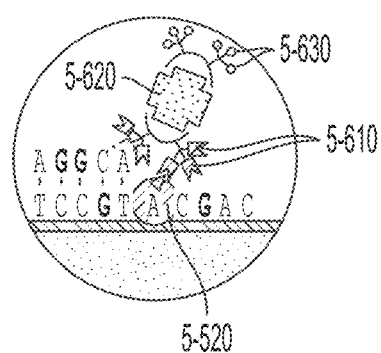
Figures 5, 6, 7:
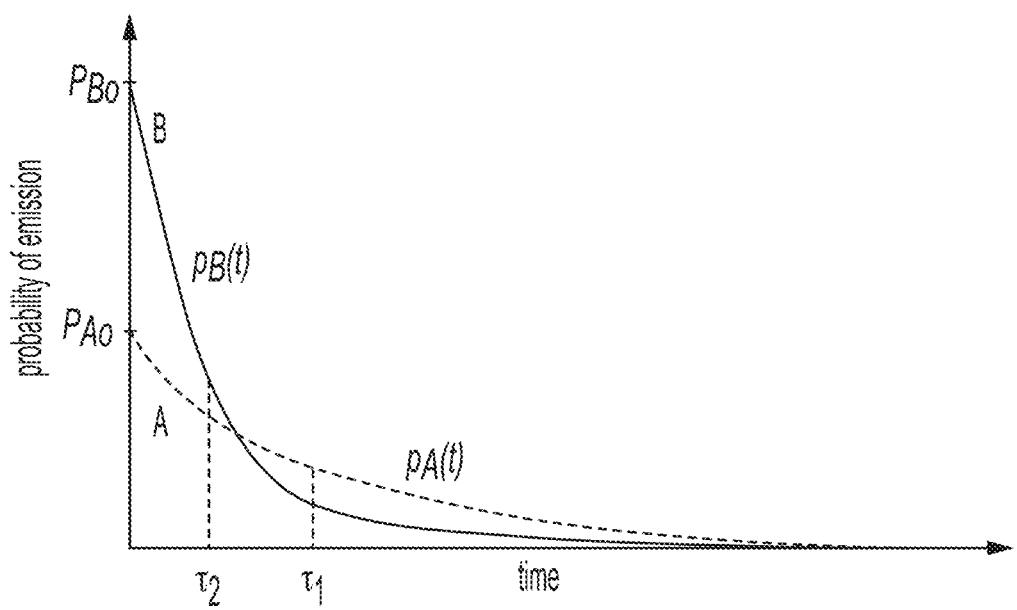
Figures 5, 6, 7, 8:
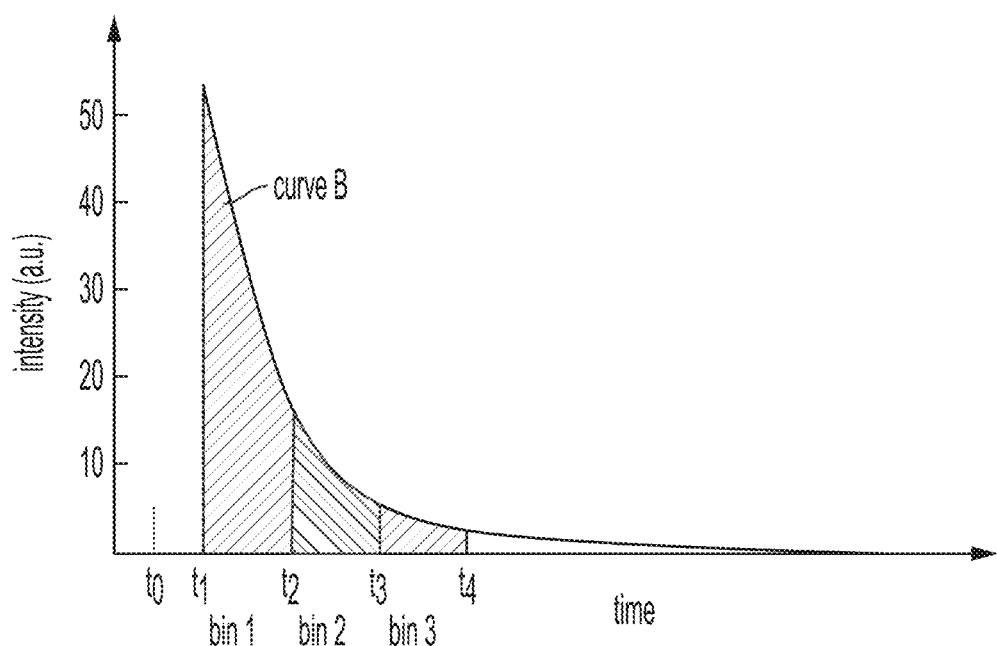
Figures 5, 6, 7, 8, 9:
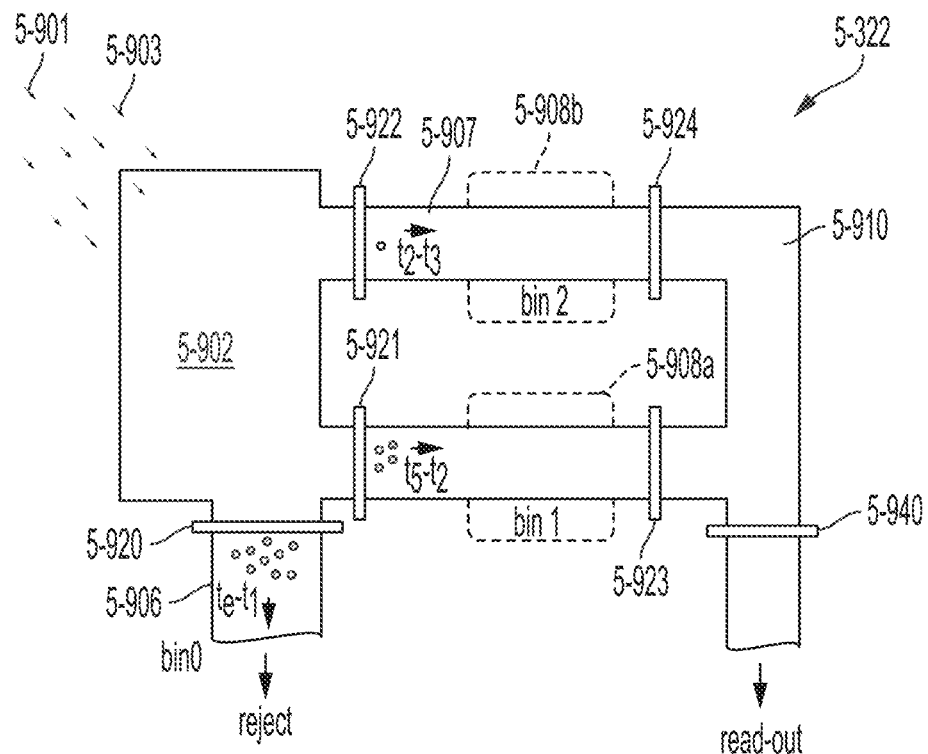
Figures 5, 6, 7, 8, 9, 10, 10A:
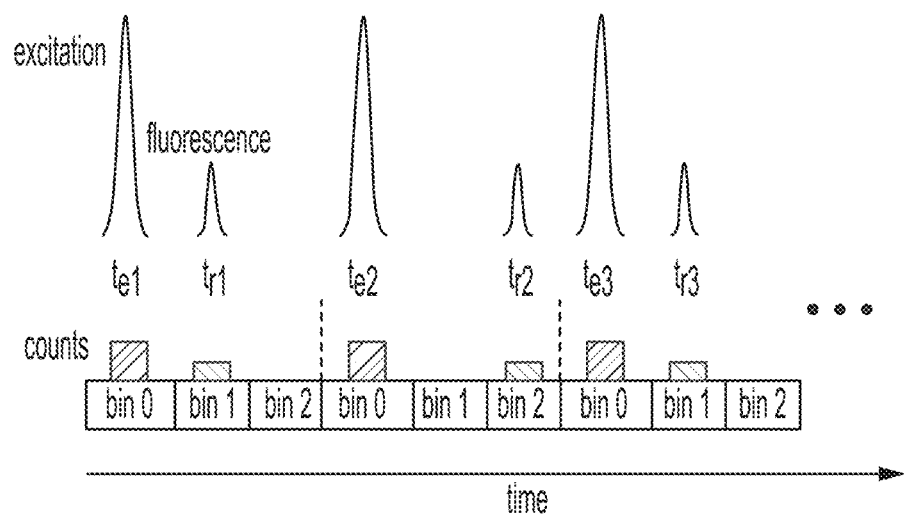
Figures 5, 6, 7, 8, 9, 10, 10B:
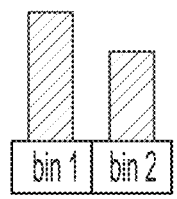
Figures 5, 6, 7, 8, 9, 10, 11, 11A:
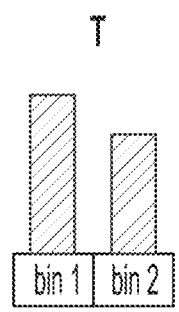
Figures 5, 6, 7, 8, 9, 10, 11, 11B:
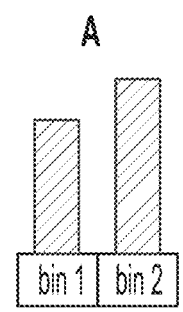
Figures 5, 6, 7, 8, 9, 10, 11, 11C:
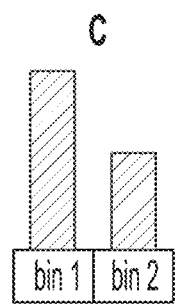
Figures 5, 6, 7, 8, 9, 10, 11, 11D:
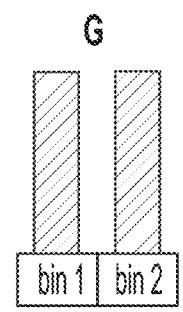
Figures 5, 6, 7, 8, 9, 10, 11, 12:
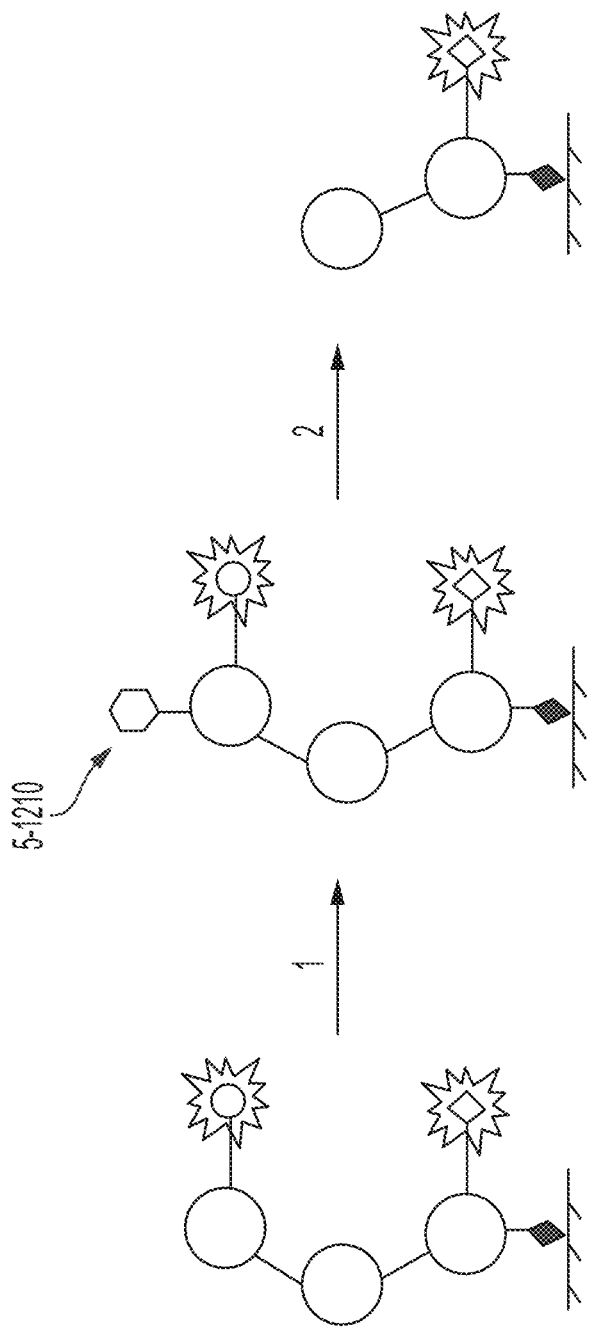
Figures 5, 6, 7, 8, 9, 10, 11, 12, 13:
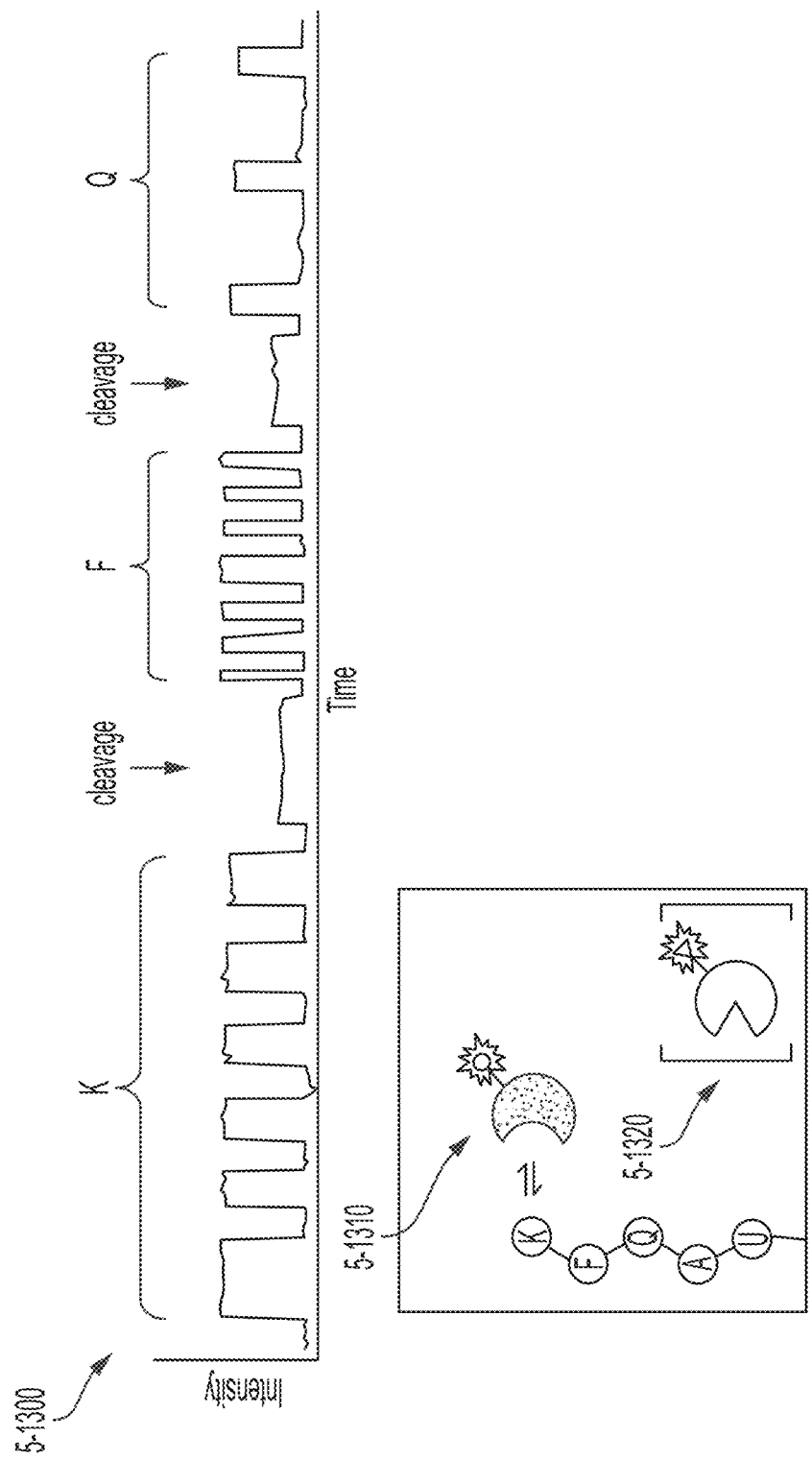

FIG. 5-1D depicts a further detailed example of a portable analytical instrument 5-100 that includes a compact pulsed optical source 5-106. In this example, the pulsed optical source 5-106 comprises a compact, passively mode-locked laser module 5-113. A passively mode-locked laser can produce optical pulses autonomously, without the application of an external pulsed signal. In some implementations, the module can be mounted to an instrument chassis or frame 5-103, and may be located inside an outer casing of the instrument. According to some embodiments, a pulsed optical source 5-106 can include additional components that can be used to operate the optical source and operate on an output beam from the optical source 5-106. A mode-locked laser 5-113 may comprise an element (e.g., saturable absorber, acousto-optic modulator, Kerr lens) in a laser cavity, or coupled to the laser cavity, that induces phase locking of the laser's longitudinal frequency modes. The laser cavity can be defined in part by cavity end mirrors 5-111, 5-119. Such locking of the frequency modes results in pulsed operation of the laser (e.g., an intracavity pulse 5-120 bounces back-and-forth between the cavity end mirrors) and produces a stream of output optical pulses 5-122 from one end mirror 5-111 which is partially transmitting.

In some cases, the analytic instrument 5-100 is configured to receive a removable, packaged, bio-optoelectronic or optoelectronic chip 5-140 (also referred to as a "disposable chip"). The disposable chip can include a bio-optoelectronic chip, for example, that comprises a plurality of reaction chambers, integrated optical components arranged to deliver optical excitation energy to the reaction chambers, and integrated photodetectors arranged to detect fluorescent emission from the reaction chambers. In some implementations, the chip 5-140 can be disposable after a single use, whereas in other implementations the chip 5-140 can be reused two or more times. When the chip 5-140 is received by the instrument 5-100, it can be in electrical and optical communication with the pulsed optical source 5-106 and with apparatus in the analytic system 5-160. Electrical communication may be made through electrical contacts on the chip package, for example.

In some embodiments and referring to FIG. 5-1D, the disposable chip 5-140 can be mounted (e.g., via a socket connection) on an electronic circuit board 5-130, such as a printed circuit board (PCB) that can include additional instrument electronics. For example, the PCB 5-130 can include circuitry configured to provide electrical power, one or more clock signals, and control signals to the optoelectronic chip 5-140, and signal-processing circuitry arranged to receive signals representative of fluorescent emission detected from the reaction chambers. Data returned from the optoelectronic chip can be processed in part or entirely by electronics on the instrument 5-100, although data may be transmitted via a network connection to one or more remote data processors, in some implementations. The PCB 5-130 can also include circuitry configured to receive feedback signals from the chip relating to optical coupling and power levels of the optical pulses 5-122 coupled into waveguides of the optoelectronic chip 5-140. The feedback signals can be provided to one or both of the pulsed optical source 5-106 and optical system 5-115 to control one or more parameters of the output beam of optical pulses 5-122. In some cases, the PCB 5-130 can provide or route power to the pulsed optical source 5-106 for operating the optical source and related circuitry in the optical source 5-106.

According to some embodiments, the pulsed optical source 5-106 comprises a compact mode-locked laser module 5-113. The mode-locked laser can comprise a gain medium 5-105 (which can be solid-state material in some embodiments), an output coupler 5-111, and a laser-cavity end mirror 5-119. The mode-locked laser's optical cavity can be bound by the output coupler 5-111 and end mirror 5-119. An optical axis 5-125 of the laser cavity can have one or more folds (turns) to increase the length of the laser cavity and provide a desired pulse repetition rate. The pulse repetition rate is determined by the length of the laser cavity (e.g., the time for an optical pulse to make a round-trip within the laser cavity).

In some embodiments, there can be additional optical elements (not shown in FIG. 5-1D) in the laser cavity for beam shaping, wavelength selection, and/or pulse forming. In some cases, the end mirror 5-119 comprises a saturable-absorber mirror (SAM) that induces passive mode locking of longitudinal cavity modes and results in pulsed operation of the mode-locked laser. The mode-locked laser module 5-113 can further include a pump source (e.g., a laser diode, not shown in FIG. 5-1D) for exciting the gain medium 5-105. Further details of a mode-locked laser module 5-113 can be found in U.S. patent application Ser. No. 15/844,469, titled "Compact Mode-Locked Laser Module," filed Dec. 15, 2017, each application of which is incorporated herein by reference.

When the laser 5-113 is mode locked, an intracavity pulse 5-120 can circulate between the end mirror 5-119 and the output coupler 5-111, and a portion of the intracavity pulse can be transmitted through the output coupler 5-111 as an output pulse 5-122. Accordingly, a train of output pulses 5-122, as depicted in the graph of FIG. 5-2, can be detected at the output coupler as the intracavity pulse 5-120 bounces back-and-forth between the output coupler 5-111 and end mirror 5-119 in the laser cavity.

FIG. 5-2 depicts temporal intensity profiles of the output pulses 5-122, though the illustration is not to scale. In some embodiments, the peak intensity values of the emitted pulses may be approximately equal, and the profiles may have a Gaussian temporal profile, though other profiles such as a sech2 profile may be possible. In some cases, the pulses may not have symmetric temporal profiles and may have other temporal shapes. The duration of each pulse may be characterized by a full-width-half-maximum (FWHM) value, as indicated in FIG. 5-2. According to some embodiments of a mode-locked laser, ultrashort optical pulses can have FWHM values less than 100 picoseconds (ps). In some cases, the FWHM values can be between approximately 5 ps and approximately 30 ps.

The output pulses 5-122 can be separated by regular intervals T. For example, T can be determined by a round-trip travel time between the output coupler 5-111 and cavity end mirror 5-119. According to some embodiments, the pulse-separation interval T can be between about 1 ns and about 30 ns. In some cases, the pulse-separation interval T can be between about 5 ns and about 20 ns, corresponding to a laser-cavity length (an approximate length of the optical axis 5-125 within the laser cavity) between about 0.7 meter and about 3 meters. In embodiments, the pulse-separation interval corresponds to a round trip travel time in the laser cavity, so that a cavity length of 3 meters (round-trip distance of 6 meters) provides a pulse-separation interval T of approximately 20 ns.

According to some embodiments, a desired pulse-separation interval T and laser-cavity length can be determined by a combination of the number of reaction chambers on the chip 5-140, fluorescent emission characteristics, and the speed of data-handling circuitry for reading data from the optoelectronic chip 5-140. In embodiments, different fluorophores can be distinguished by their different fluorescent decay rates or characteristic lifetimes. Accordingly, there needs to be a sufficient pulse-separation interval T to collect adequate statistics for the selected fluorophores to distinguish between their different decay rates. Additionally, if the pulse-separation interval T is too short, the data handling circuitry cannot keep up with the large amount of data being collected by the large number of reaction chambers. Pulse-separation interval T between about 5 ns and about 20 ns is suitable for fluorophores that have decay rates up to about 2 ns and for handling data from between about 60,000 and 10,000,000 reaction chambers.

According to some implementations, a beam-steering module 5-150 can receive output pulses from the pulsed optical source 5-106 and is configured to adjust at least the position and incident angles of the optical pulses onto an optical coupler (e.g., grating coupler) of the optoelectronic chip 5-140. In some cases, the output pulses 5-122 from the pulsed optical source 5-106 can be operated on by a beam-steering module 5-150 to additionally or alternatively change a beam shape and/or beam rotation at an optical coupler on the optoelectronic chip 5-140. In some implementations, the beam-steering module 5-150 can further provide focusing and/or polarization adjustments of the beam of output pulses onto the optical coupler. One example of a beam-steering module is described in U.S. patent application Ser. No. 15/161,088 titled "Pulsed Laser and Bioanalytic System," filed May 20, 2016, which is incorporated herein by reference. Another example of a beam-steering module is described in a separate U.S. patent application No. 62/435,679, filed Dec. 16, 2016, and titled "Compact Beam Shaping and Steering Assembly," which is incorporated herein by reference.

Referring to FIG. 5-3, the output pulses 5-122 from a pulsed optical source can be coupled into one or more optical waveguides 5-312 on a bio-optoelectronic chip 5-140, for example. In some embodiments, the optical pulses can be coupled to one or more waveguides via a grating coupler 5-310, though coupling to an end of one or more optical waveguides on the optoelectronic chip can be used in some embodiments. According to some embodiments, a quad detector 5-320 can be located on a semiconductor substrate 5-305 (e.g., a silicon substrate) for aiding in alignment of the beam of optical pulses 5-122 to a grating coupler 5-310. The one or more waveguides 5-312 and reaction chambers or reaction chambers 5-330 can be integrated on the same semiconductor substrate with intervening dielectric layers (e.g., silicon dioxide layers) between the substrate, waveguide, reaction chambers, and photodetectors 5-322.

Each waveguide 5-312 can include a tapered portion 5-315 below the reaction chambers 5-330 to equalize optical power coupled to the reaction chambers along the waveguide. The reducing taper can force more optical energy outside the waveguide's core, increasing coupling to the reaction chambers and compensating for optical losses along the waveguide, including losses for light coupling into the reaction chambers. A second grating coupler 5-317 can be located at an end of each waveguide to direct optical energy to an integrated photodiode 5-324. The integrated photodiode can detect an amount of power coupled down a waveguide and provide a detected signal to feedback circuitry that controls the beam-steering module 5-150, for example.

The reaction chambers 5-330 or reaction chambers 5-330 can be aligned with the tapered portion 5-315 of the waveguide and recessed in a tub 5-340. There can be photodetectors 5-322 located on the semiconductor substrate 5-305 for each reaction chamber 5-330. In some embodiments, a semiconductor absorber (shown in FIG. 5-5 as an optical filter 5-530) may be located between the waveguide and a photodetector 5-322 at each pixel. A metal coating and/or multilayer coating 5-350 can be formed around the reaction chambers and above the waveguide to prevent optical excitation of fluorophores that are not in the reaction chambers (e.g., dispersed in a solution above the reaction chambers). The metal coating and/or multilayer coating 5-350 may be raised beyond edges of the tub 5-340 to reduce absorptive losses of the optical energy in the waveguide 5-312 at the input and output ends of each waveguide.

There can be a plurality of rows of waveguides, reaction chambers, and time-binning photodetectors on the optoelectronic chip 5-140. For example, there can be 128 rows, each having 512 reaction chambers, for a total of 65,536 reaction chambers in some implementations. Other implementations may include fewer or more reaction chambers, and may include other layout configurations. Optical power from the pulsed optical source 5-106 can be distributed to the multiple waveguides via one or more star couplers or multimode interference couplers, or by any other means, located between an optical coupler 5-310 to the chip 5-140 and the plurality of waveguides 5-312.

FIG. 5-4 illustrates optical energy coupling from an optical pulse 5-122 within a tapered portion 5-315 of waveguide 5-312 to a reaction chamber 5-330. The drawing has been produced from an electromagnetic field simulation of the optical wave that accounts for waveguide dimensions, reaction chamber dimensions, the different materials' optical properties, and the distance of the tapered portion 5-315 of waveguide 5-312 from the reaction chamber 5-330. The waveguide can be formed from silicon nitride in a surrounding medium 5-410 of silicon dioxide, for example. The waveguide, surrounding medium, and reaction chamber can be formed by microfabrication processes described in U.S. application Ser. No. 14/821,688, filed Aug. 7, 2015, titled "Integrated Device for Probing, Detecting and Analyzing Molecules." According to some embodiments, an evanescent optical field 5-420 couples optical energy transported by the waveguide to the reaction chamber 5-330.

A non-limiting example of a biological reaction taking place in a reaction chamber 5-330 is depicted in FIG. 5-5. The example depicts sequential incorporation of nucleotides or nucleotide analogs into a growing strand that is complementary to a target nucleic acid. The sequential incorporation can take place in a reaction chamber 5-330, and can be detected by an advanced analytic instrument to sequence DNA. The reaction chamber can have a depth between about 150 nm and about 250 nm and a diameter between about 80 nm and about 160 nm. A metallization layer 5-540 (e.g., a metallization for an electrical reference potential) can be patterned above a photodetector 5-322 to provide an aperture or iris that blocks stray light from adjacent reaction chambers and other unwanted light sources. According to some embodiments, polymerase 5-520 can be located within the reaction chamber 5-330 (e.g., attached to a base of the chamber). The polymerase can take up a target nucleic acid 5-510 (e.g., a portion of nucleic acid derived from DNA), and sequence a growing strand of complementary nucleic acid to produce a growing strand of DNA 5-512. Nucleotides or nucleotide analogs labeled with different fluorophores can be dispersed in a solution above and within the reaction chamber.

Figures 2, 3, 4, 5, 6, 6A:
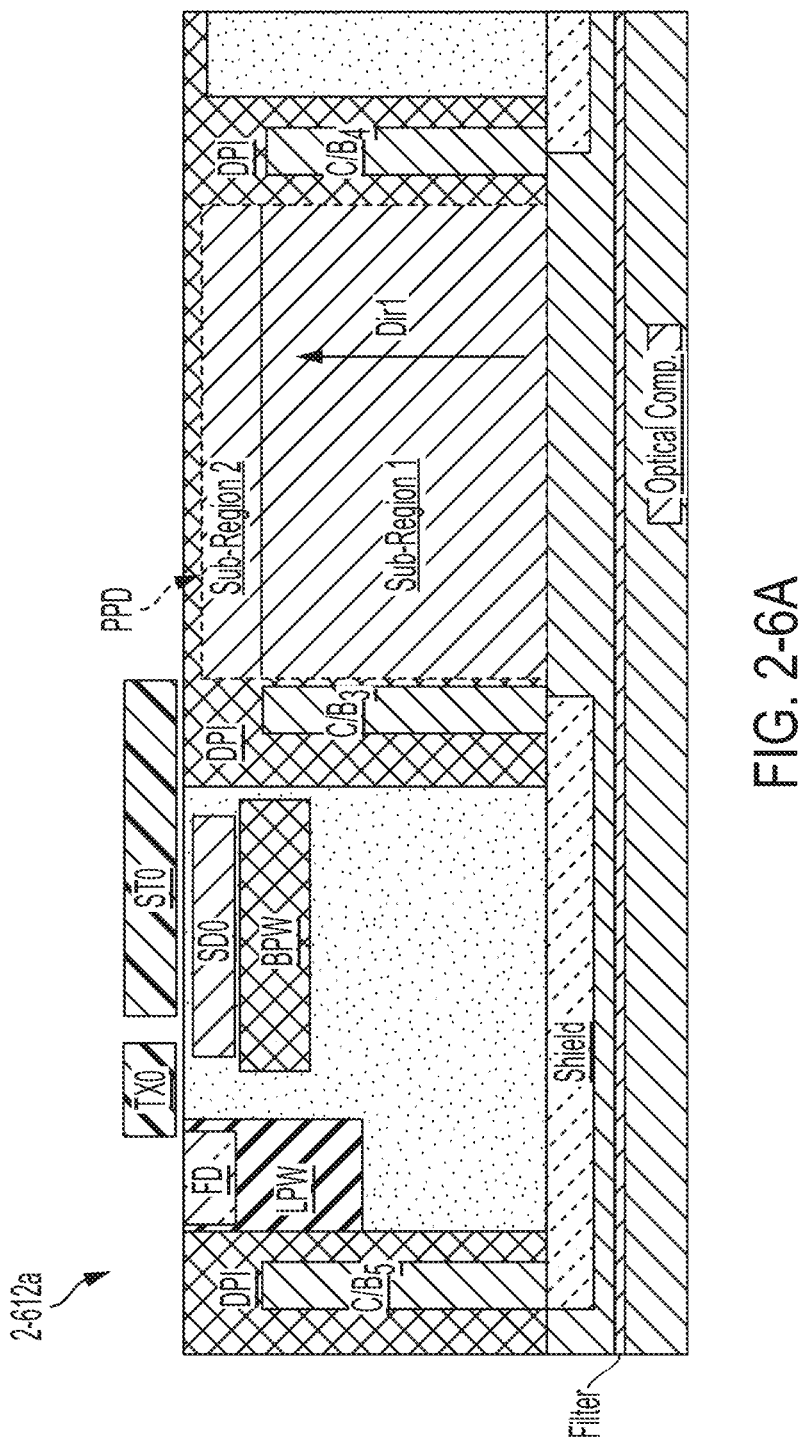
Figures 2, 3, 4, 5, 6, 6B:
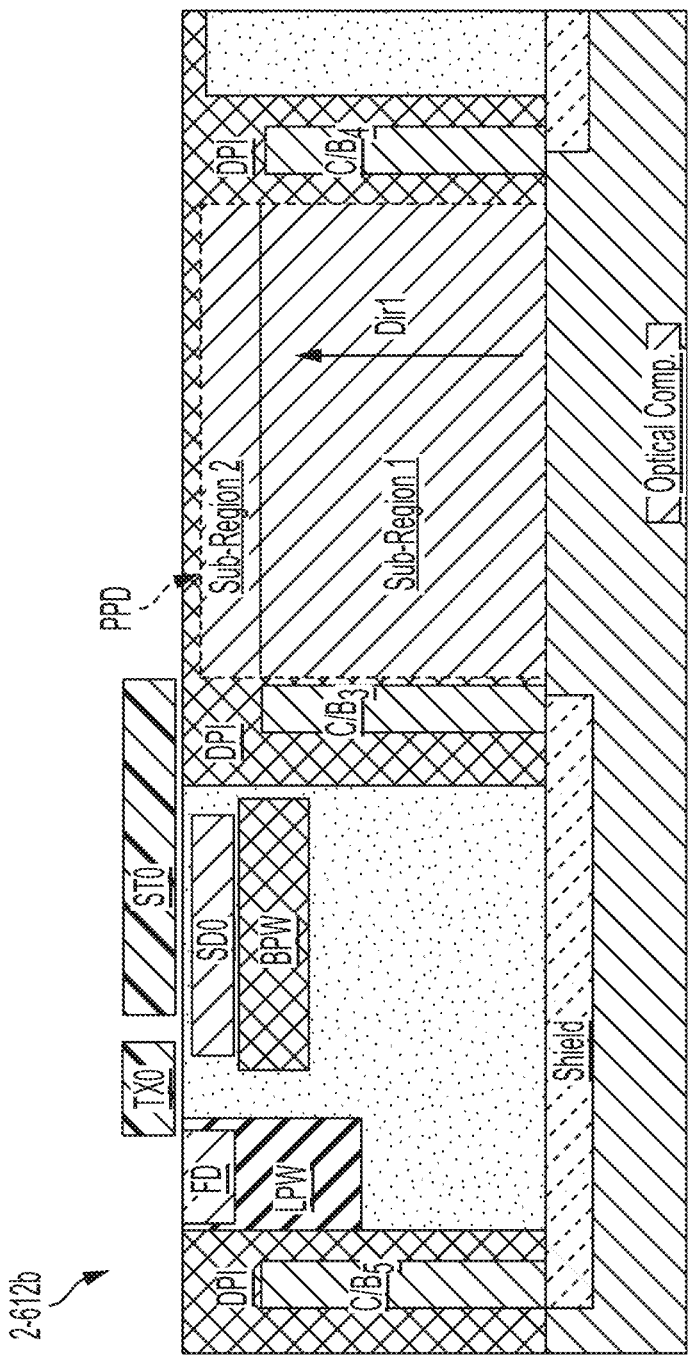

When a labeled nucleotide or nucleotide analog 5-610 is incorporated into a growing strand of complementary nucleic acid, as depicted in FIG. 5-6, one or more attached fluorophores 5-630 can be repeatedly excited by pulses of optical energy coupled into the reaction chamber 5-330 from the tapered portion 5-315. In some embodiments, the fluorophore or fluorophores 5-630 can be attached to one or more nucleotides or nucleotide analogs 5-610 with any suitable linker 5-620. An incorporation event may last for a period of time up to about 100 ms. During this time, pulses of fluorescent emission resulting from excitation of the fluorophore(s) by pulses from the mode-locked laser can be detected with a time-binning photodetector 5-322, for example. In some embodiments, there can be one or more additional integrated electronic devices 5-323 at each pixel for signal handling (e.g., amplification, read-out, routing, signal preprocessing, etc.). According to some embodiments, each pixel can include at least one optical filter 5-530 (e.g., a semiconductor absorber) that passes fluorescent emission and reduces transmission of radiation from the excitation pulse. Some implementations may not use the optical filter 5-530. By attaching fluorophores with different emission characteristics (e.g., fluorescent decay rates, intensity, fluorescent wavelength) to the different nucleotides (A,C,G,T), detecting and distinguishing the different emission characteristics while the strand of DNA 5-512 incorporates a nucleic acid and enables determination of the genetic sequence of the growing strand of DNA.

Figures 2, 3, 4, 5, 6, 7, 7A:
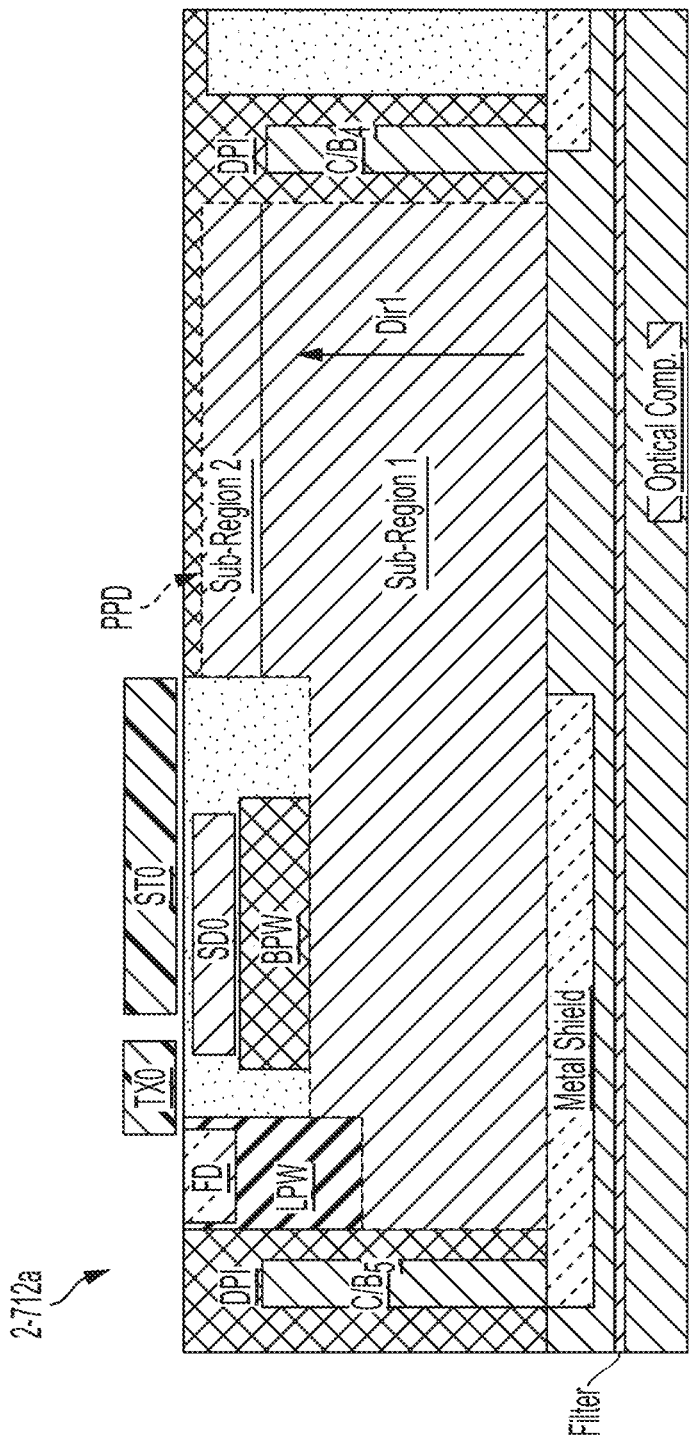
Figures 2, 3, 4, 5, 6, 7, 7B:
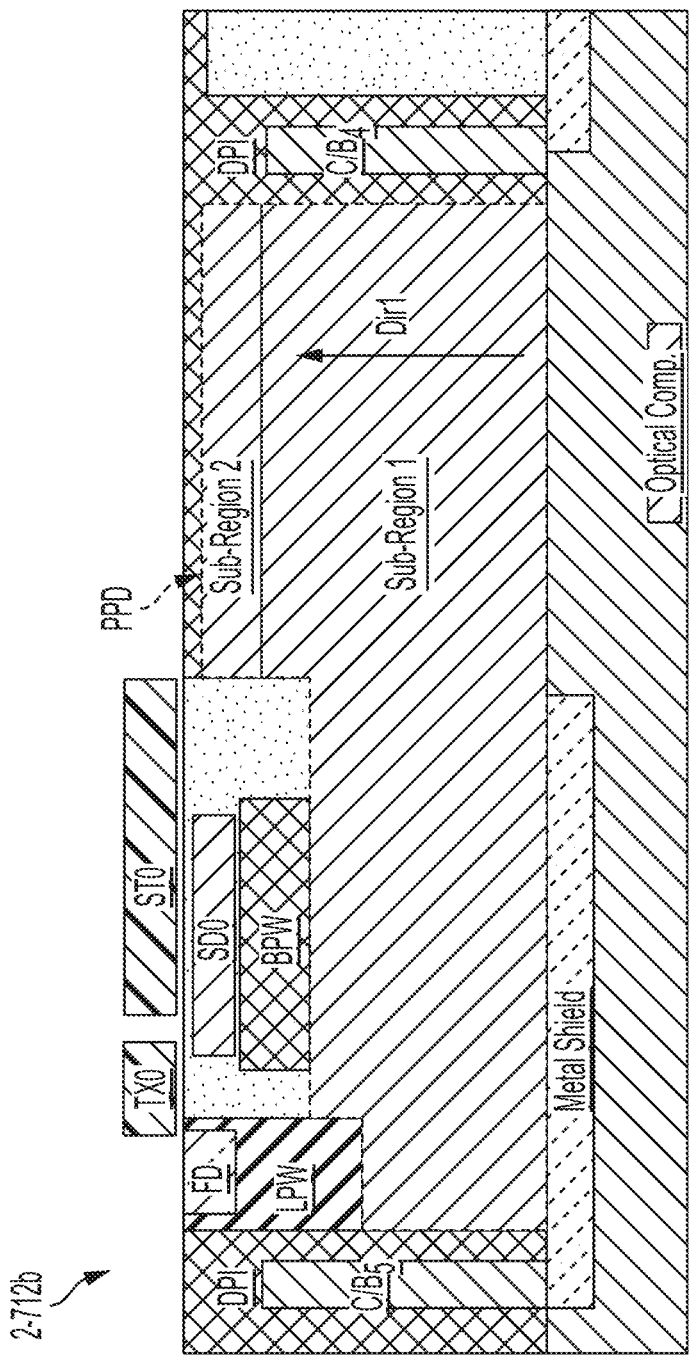
Figures 2, 3, 4, 5, 6, 7, 8:
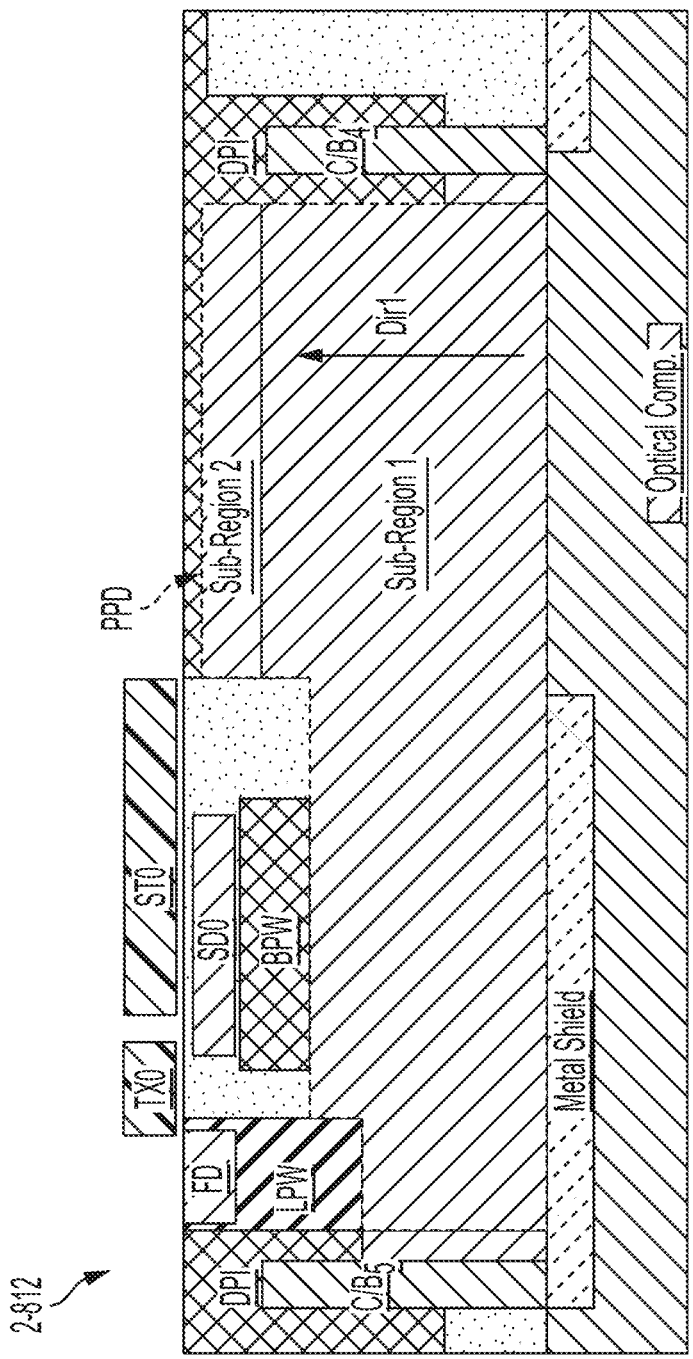
Figures 2, 3, 4, 5, 6, 7, 8, 9:
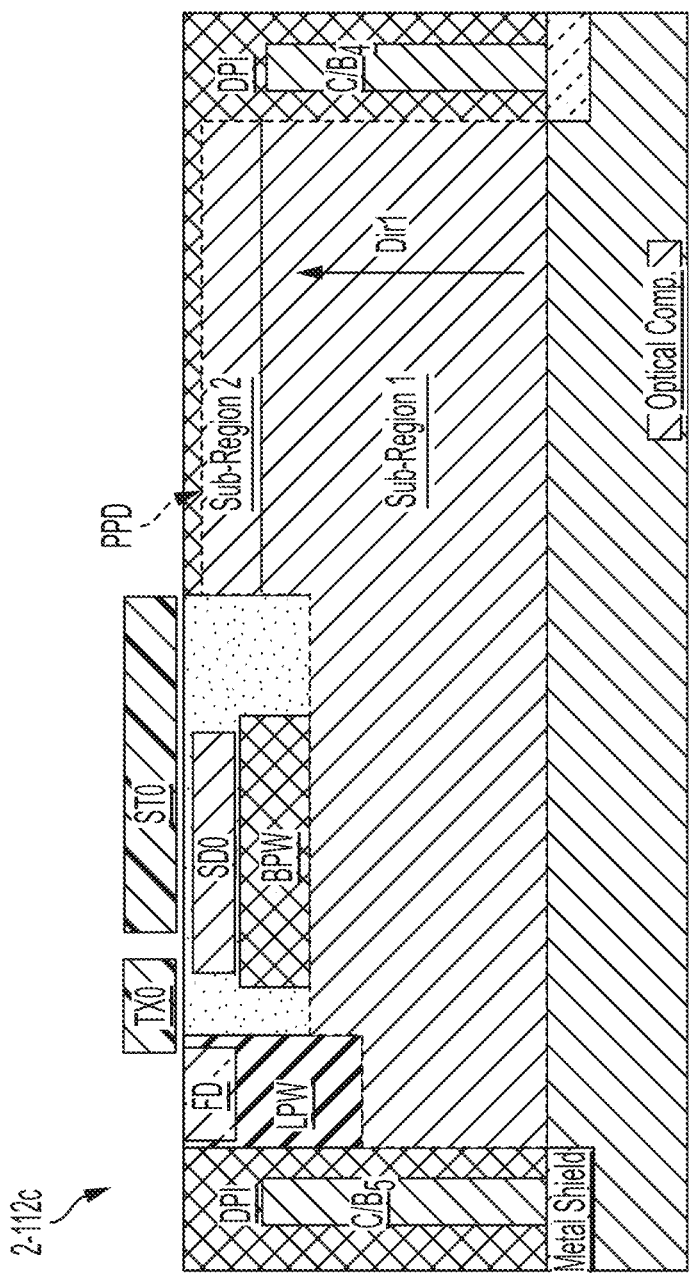
Figures 2, 3, 4, 5, 6, 7, 8, 9, 10:
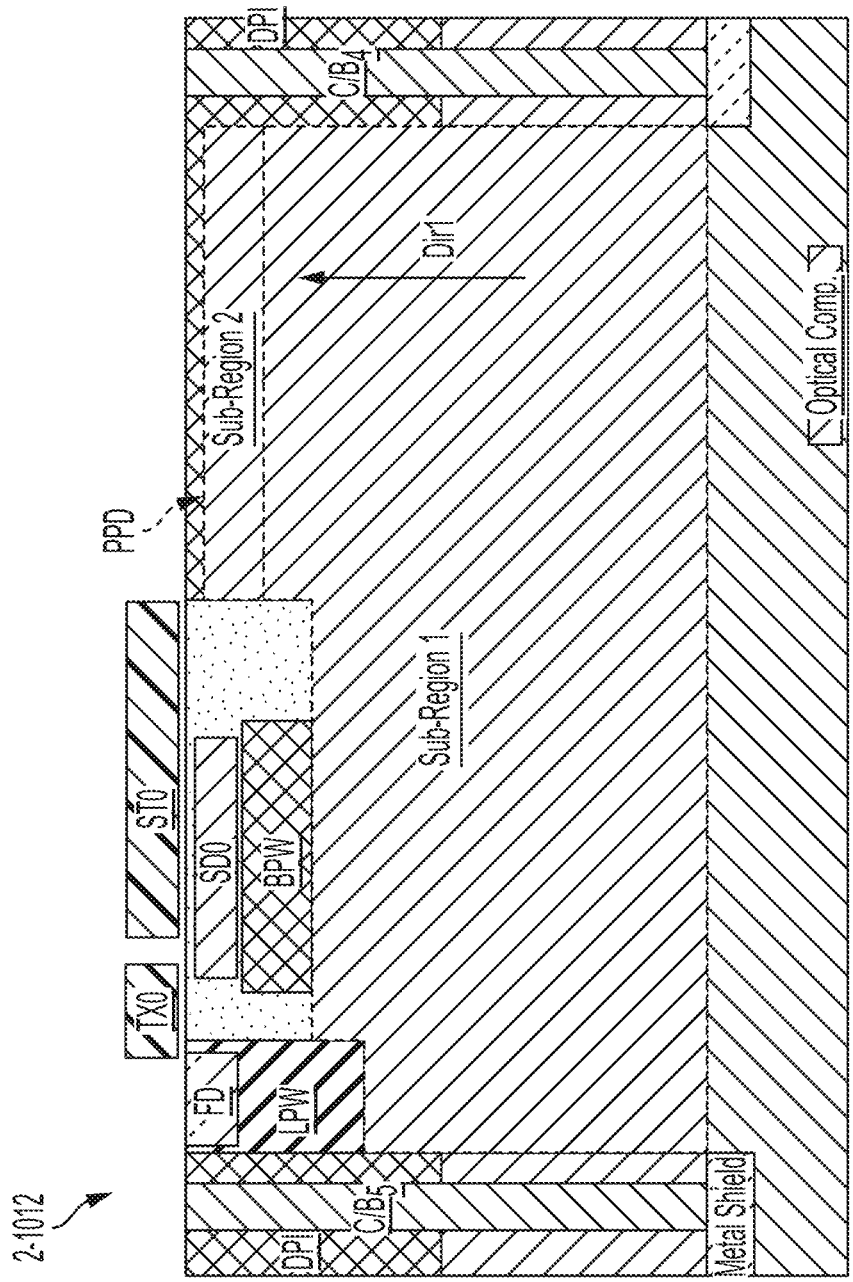
Figures 2, 3, 4, 5, 6, 7, 8, 9, 10, 11:
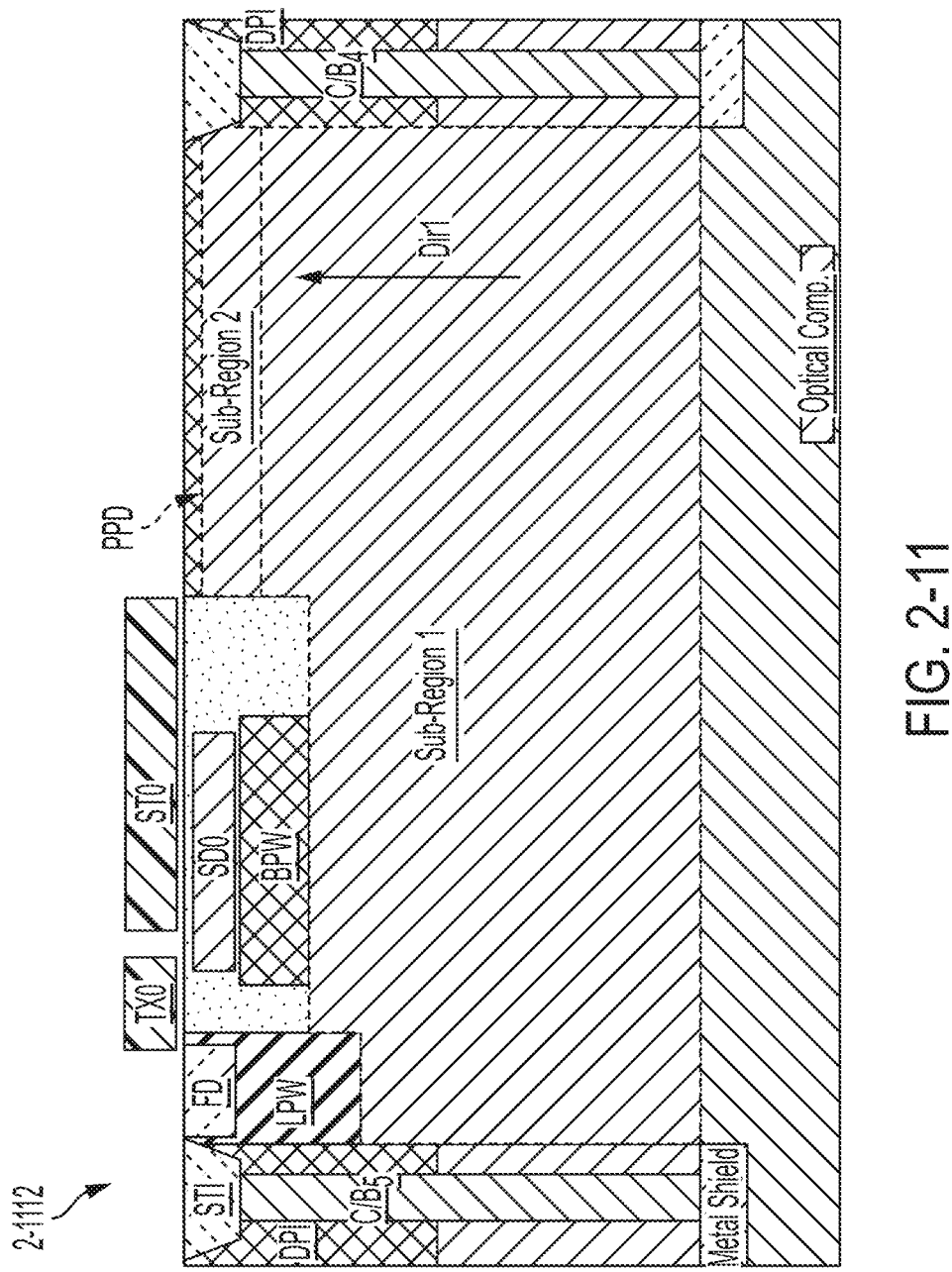
Figures 2, 3, 4, 5, 6, 7, 8, 9, 10, 11, 12, 13:
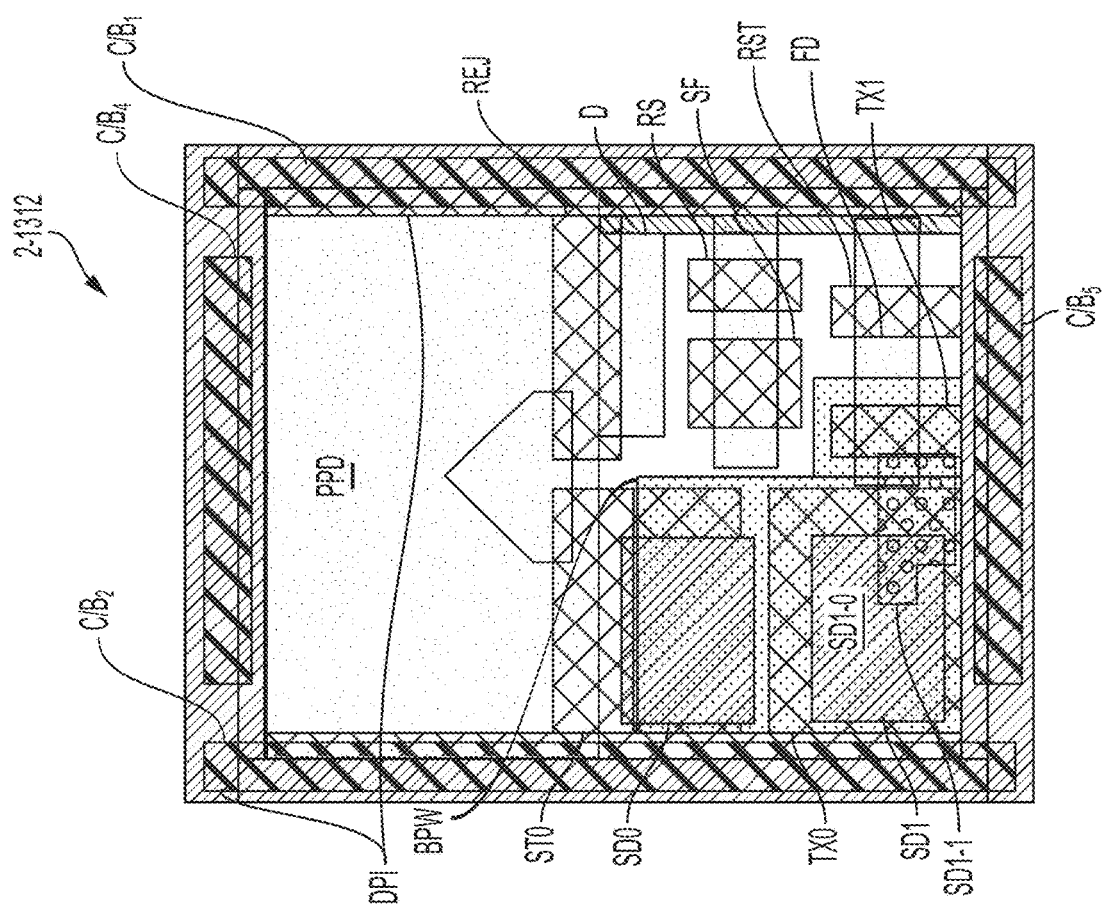
Figures 1, 3:
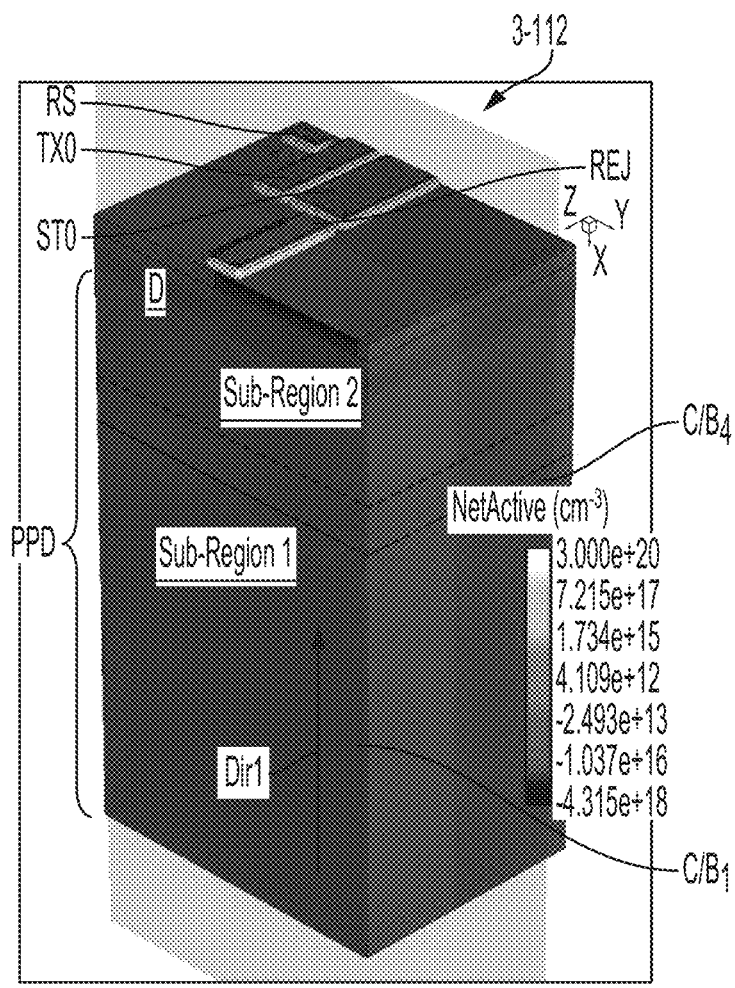
Figures 2, 3:
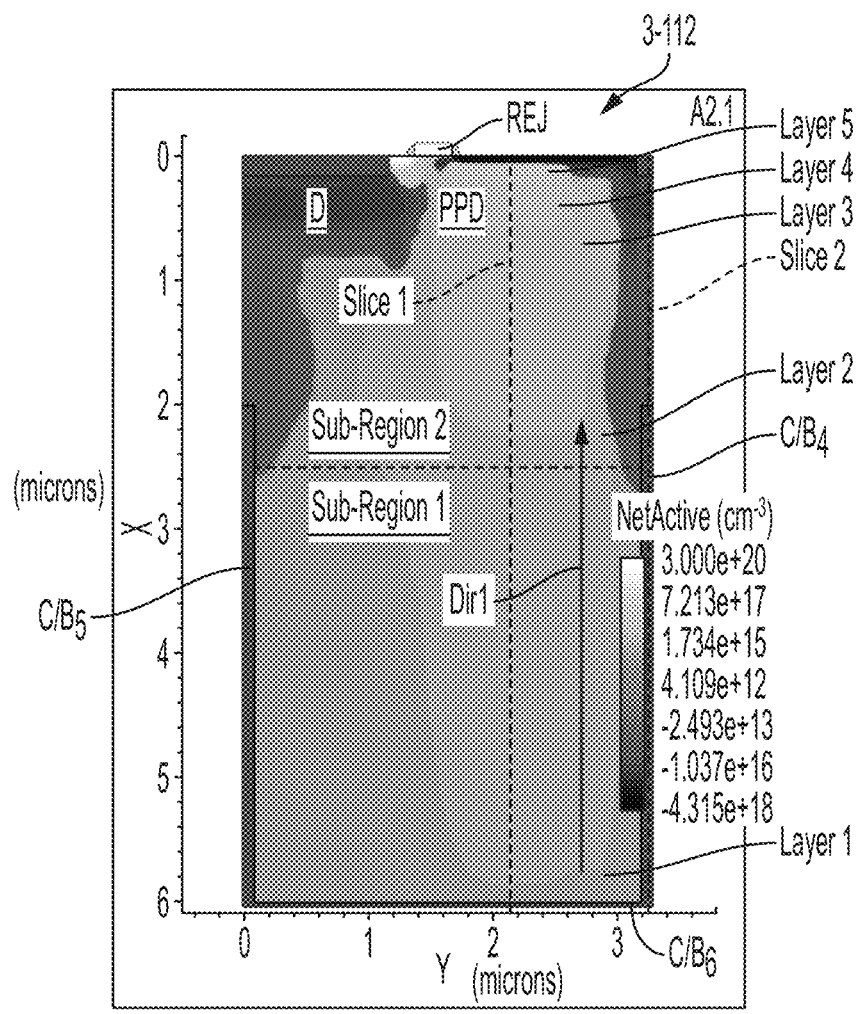
Figure 3:
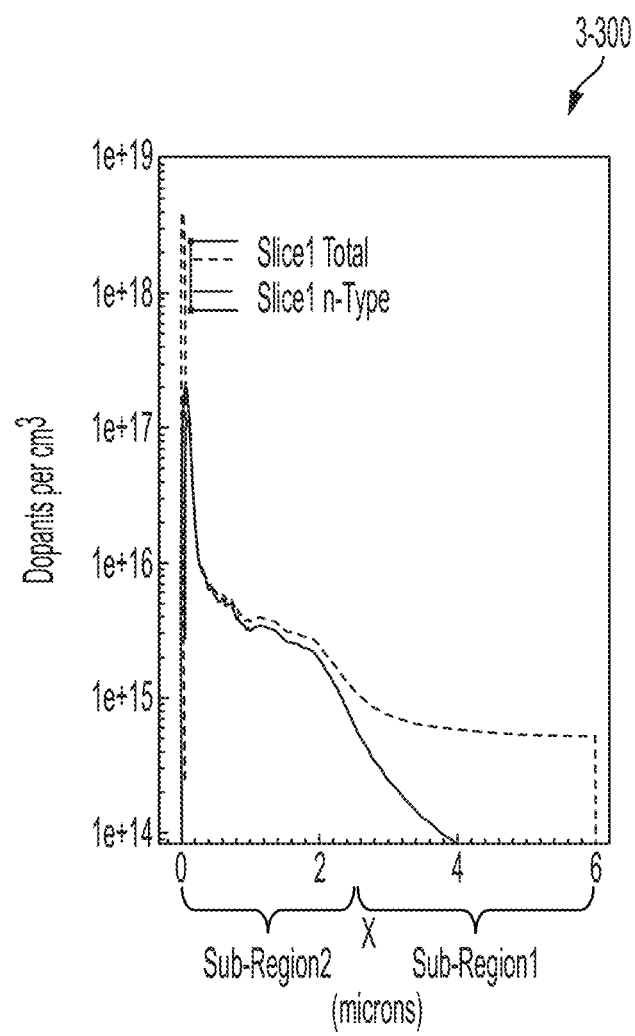
Figures 3, 4:
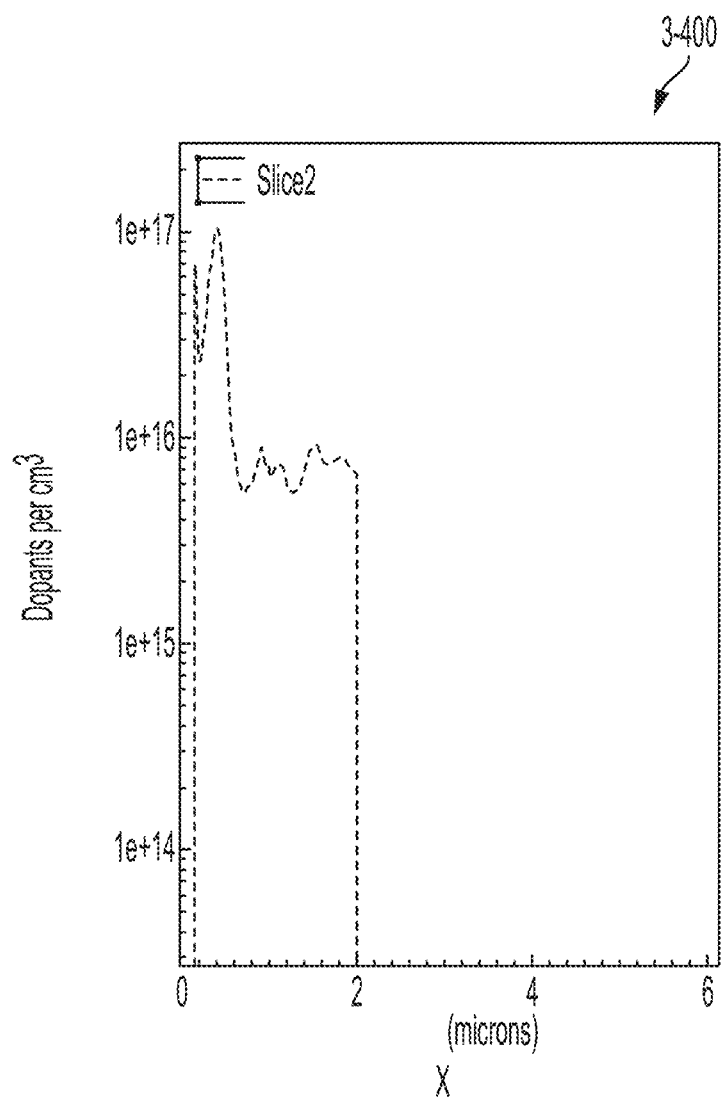
Figures 3, 4, 5, 5A, 5B:
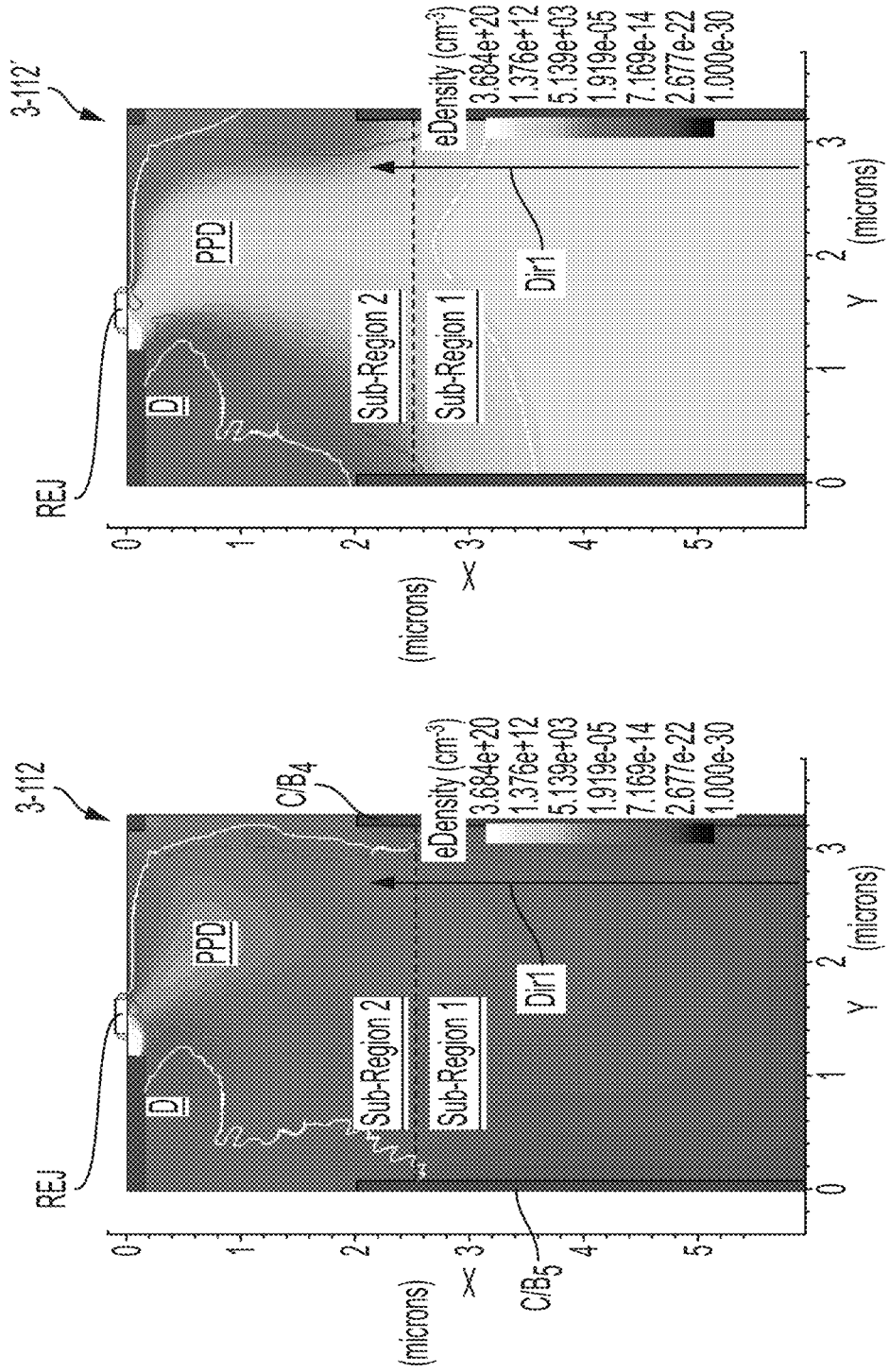
Figures 3, 4, 5, 6, 6B:
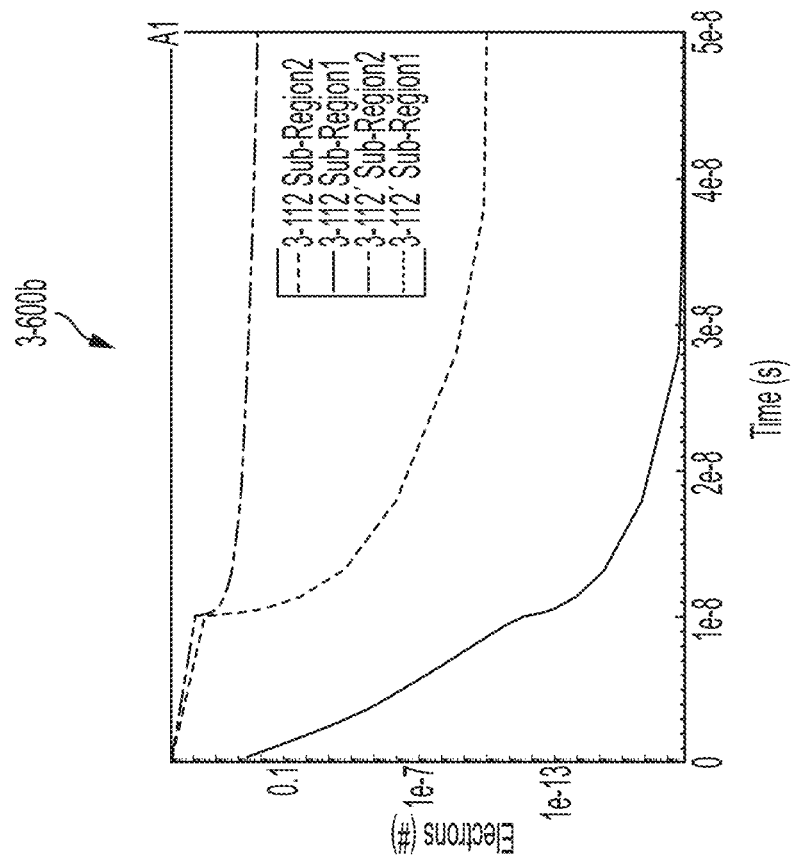
Figures 3, 4, 5, 6, 6A:
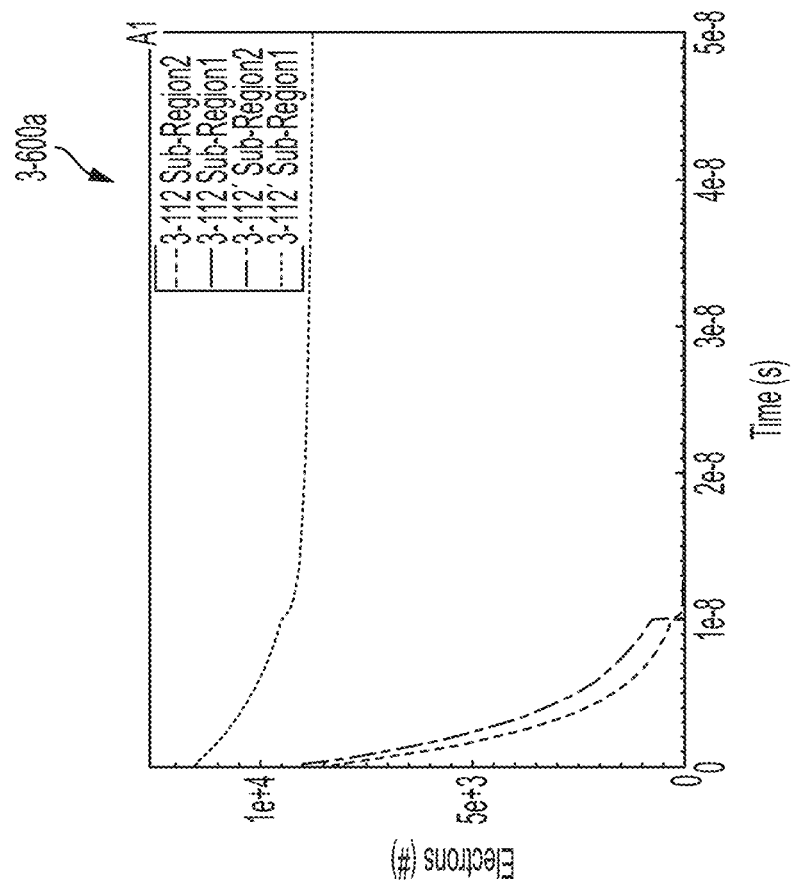
Figures 3, 4, 5, 6, 7, 7B:
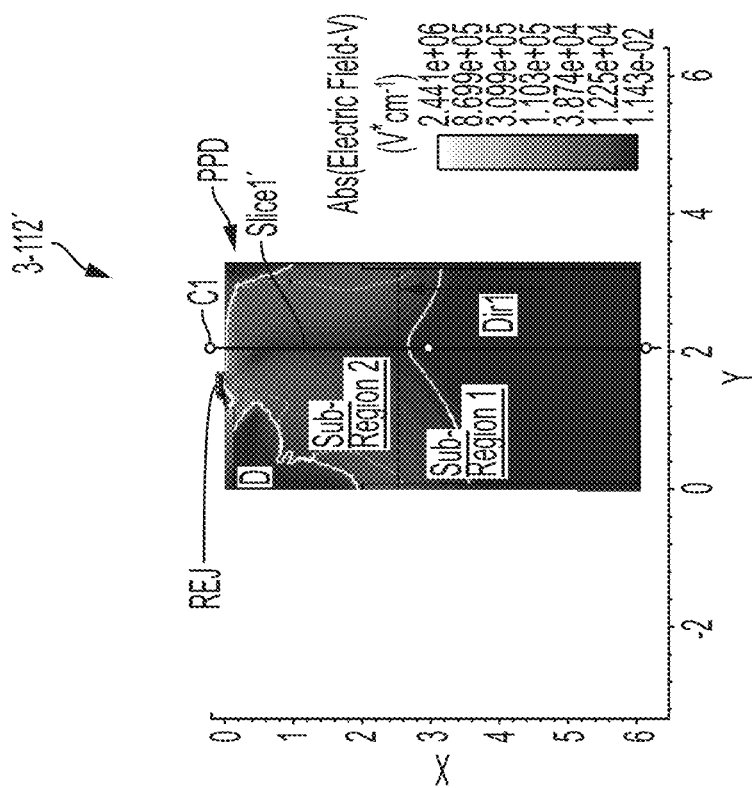
Figures 3, 4, 5, 6, 7, 7A:
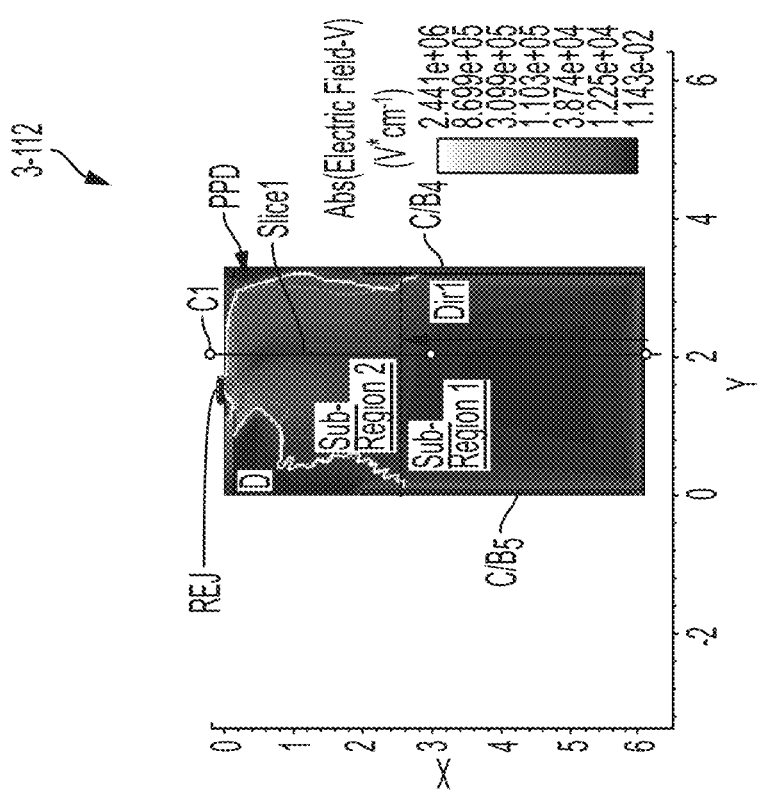
Figures 3, 4, 5, 6, 7, 8:
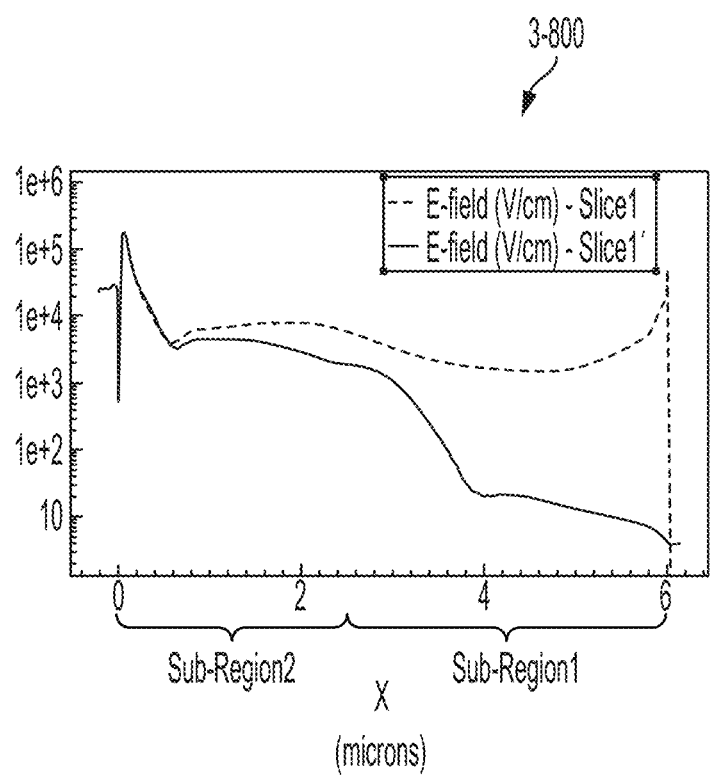
Figures 3, 4, 5, 6, 7, 8, 9, 9A:
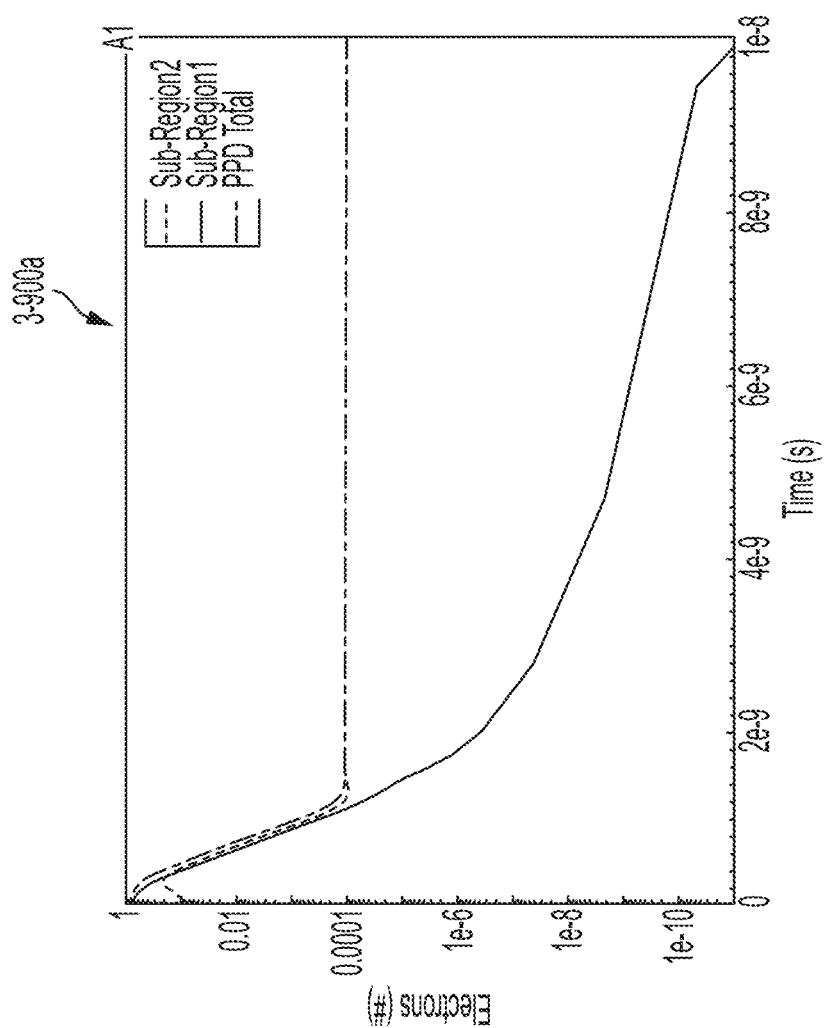
Figures 3, 4, 5, 6, 7, 8, 9, 9C:
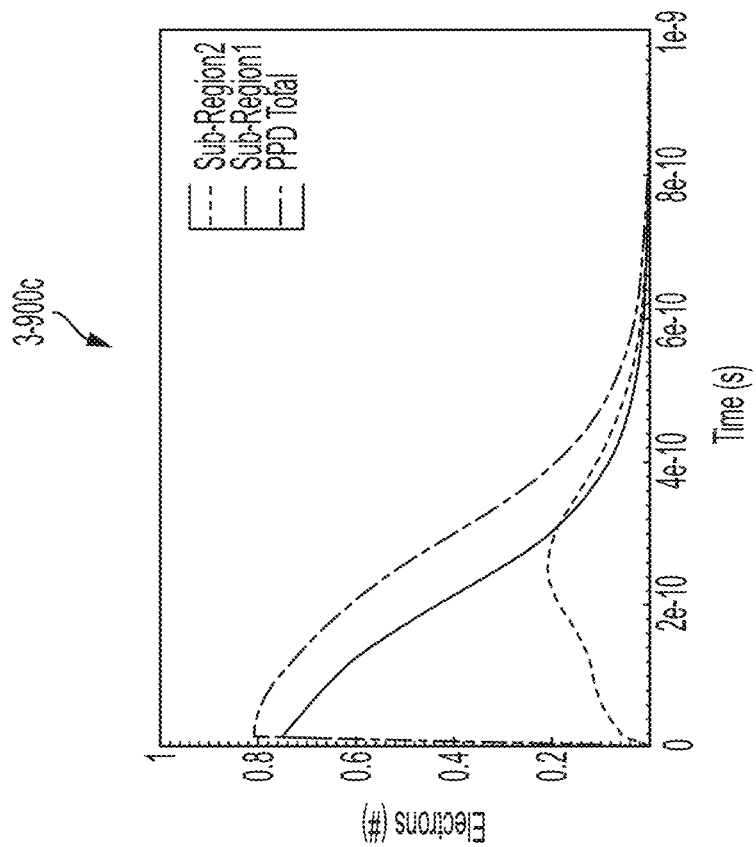
Figures 3, 4, 5, 6, 7, 8, 9, 9B:
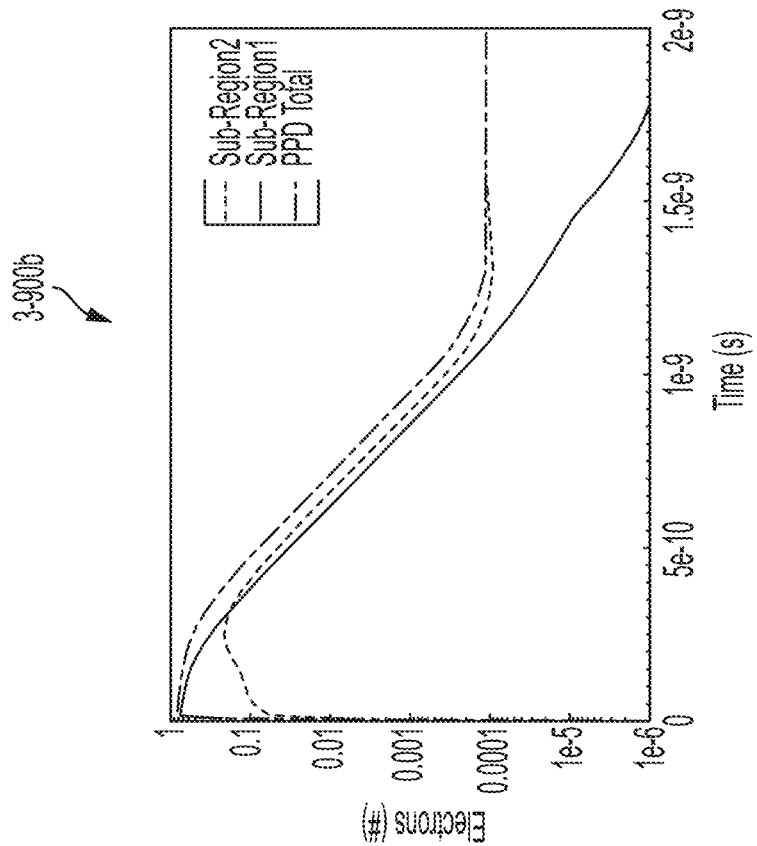
Figures 3, 4, 5, 6, 7, 8, 9, 10:
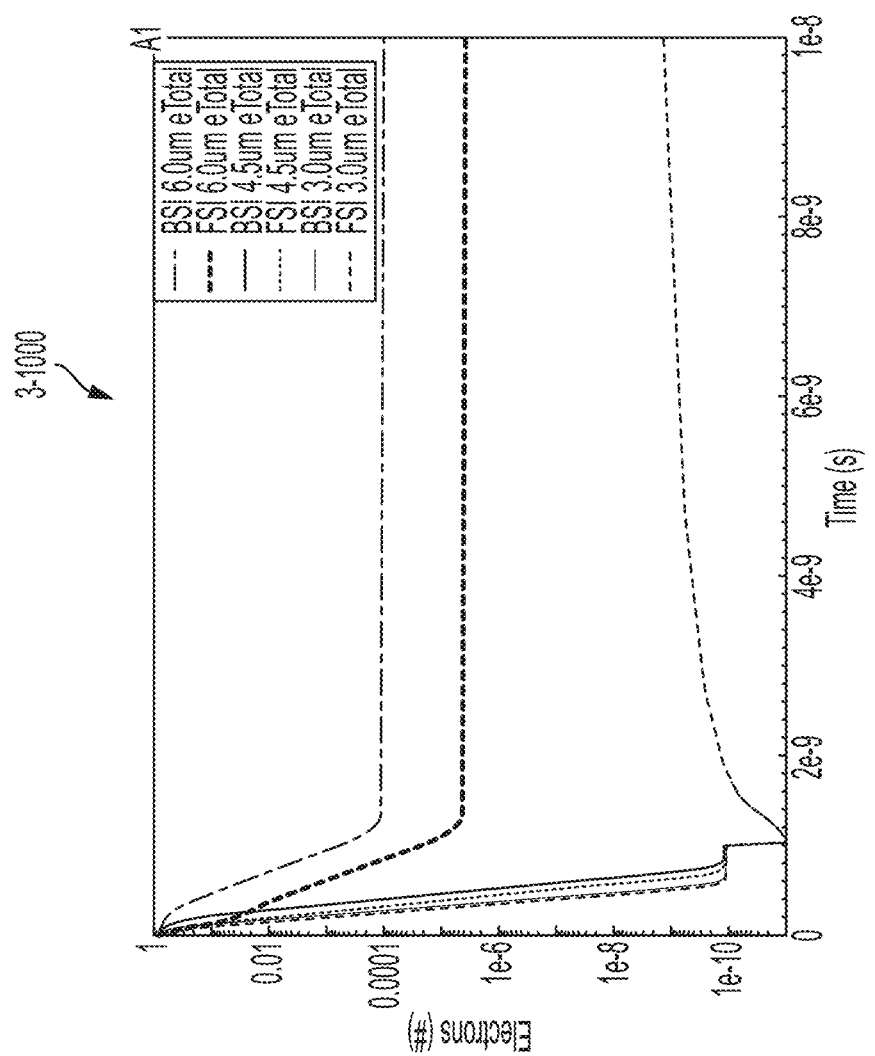
Figures 3, 4, 5, 6, 7, 8, 9, 10, 11, 11B:
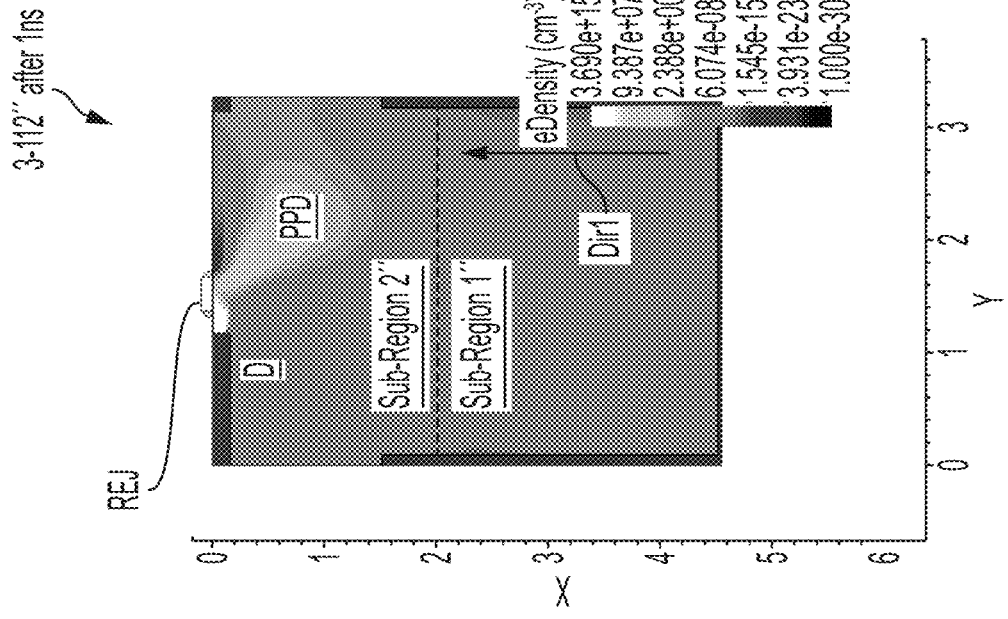
Figures 3, 4, 5, 6, 7, 8, 9, 10, 11, 11A:
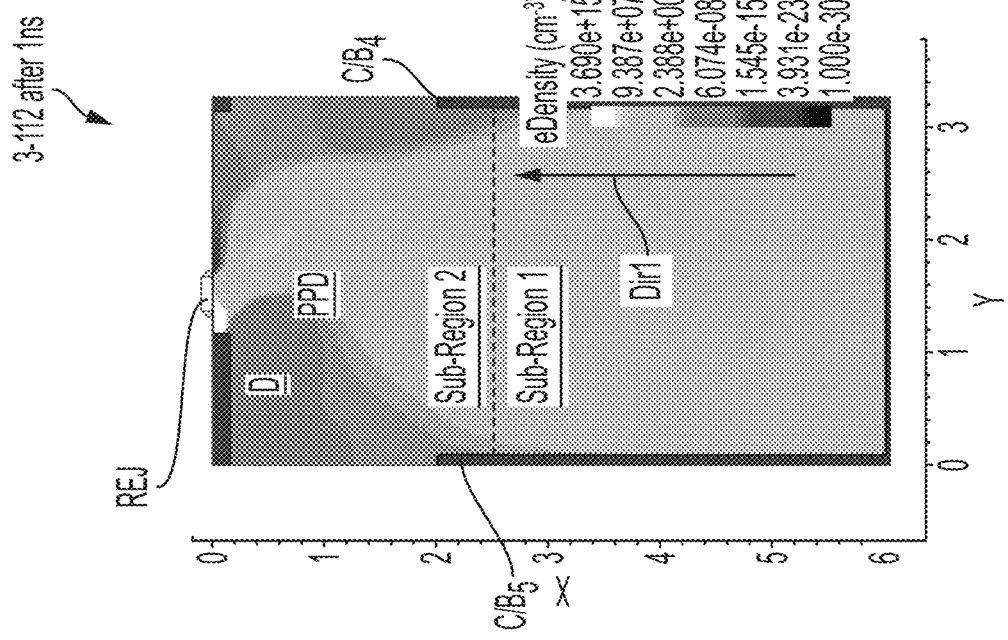
Figures 3, 4, 5, 6, 7, 8, 9, 10, 11, 12, 12A, 12B:
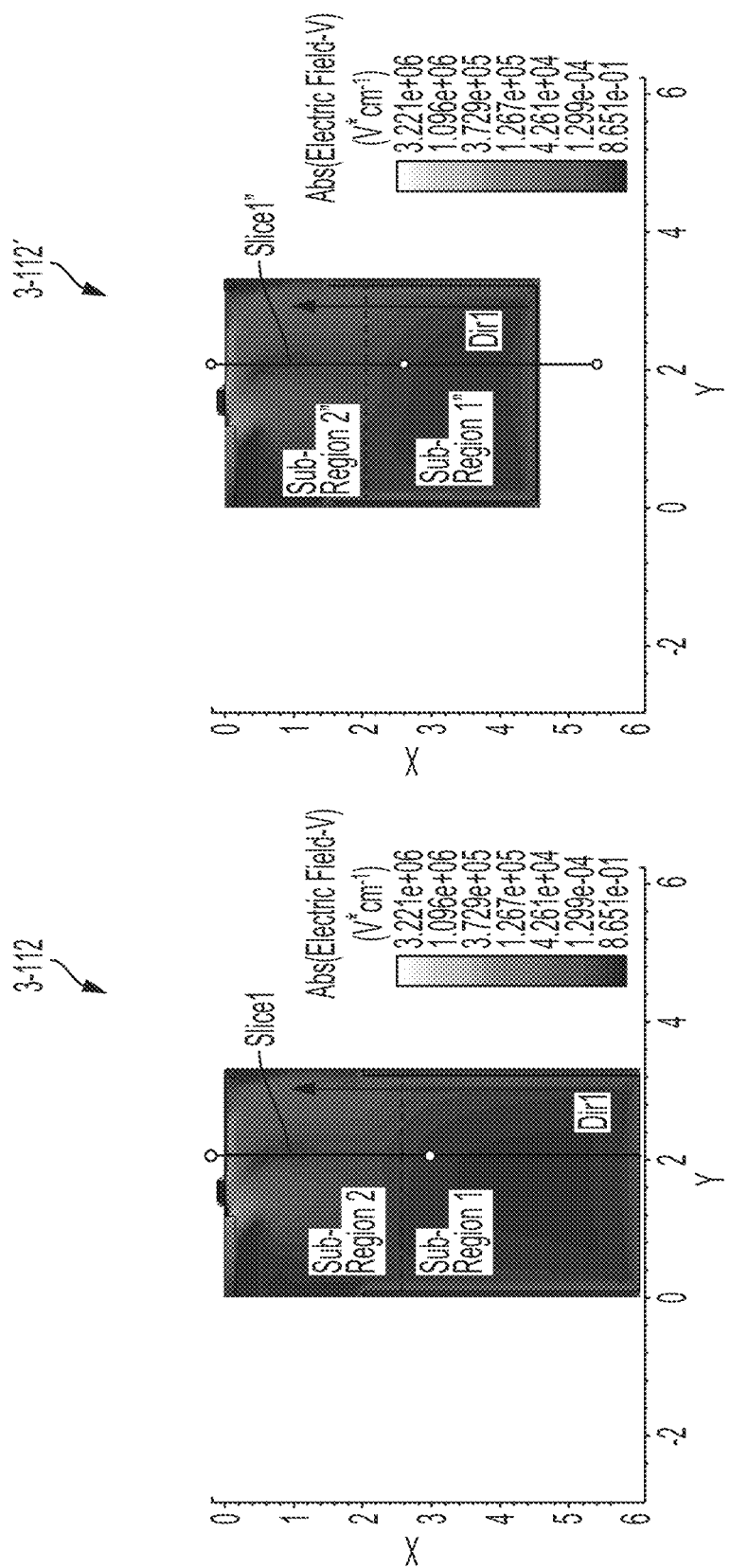
Figures 3, 4, 5, 6, 7, 8, 9, 10, 11, 12, 13:
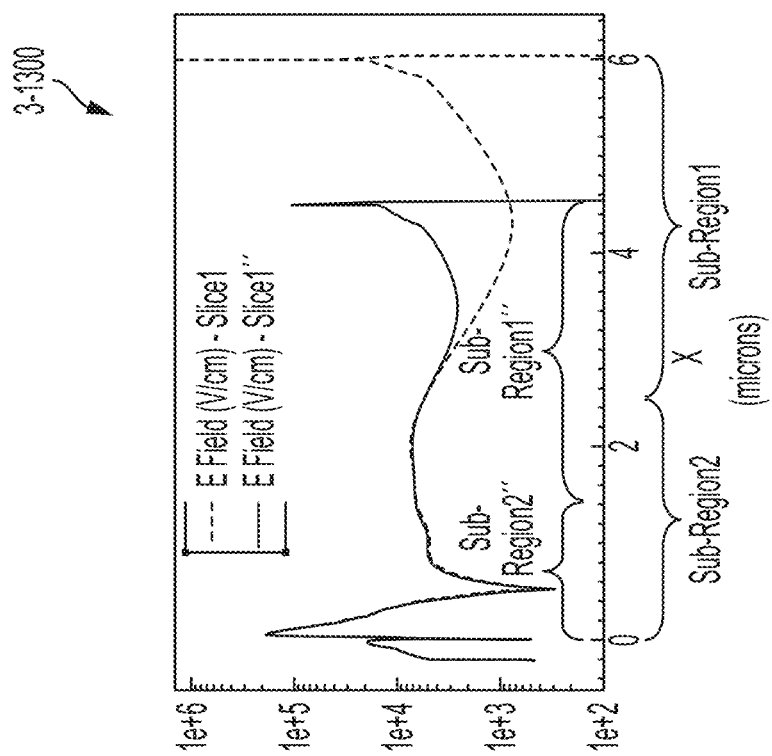
Figures 1, 4:
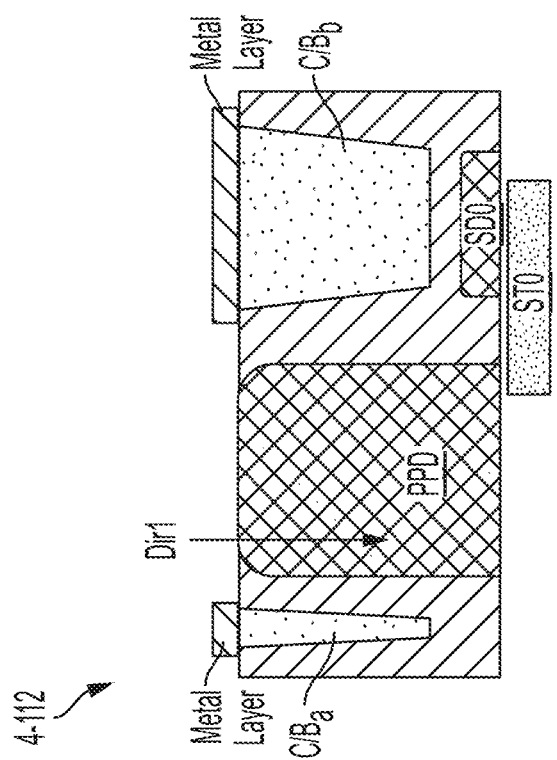
Figures 2, 4:
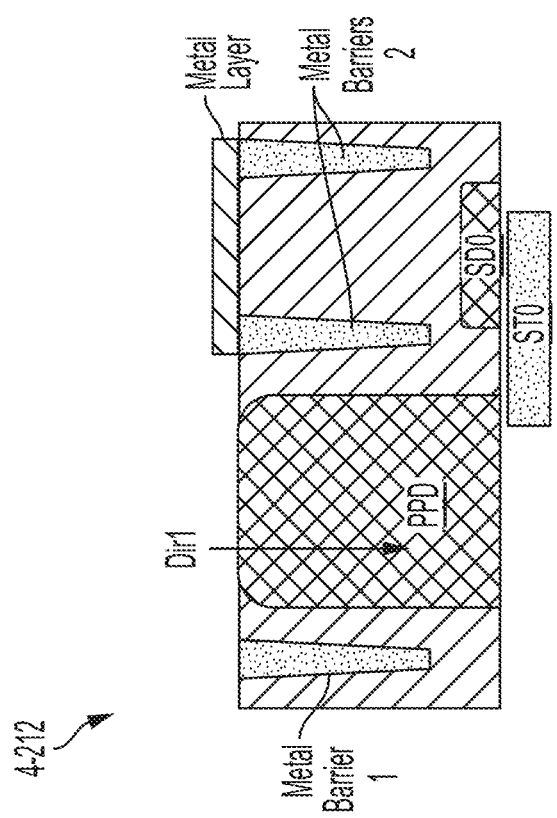
Figures 3, 4:
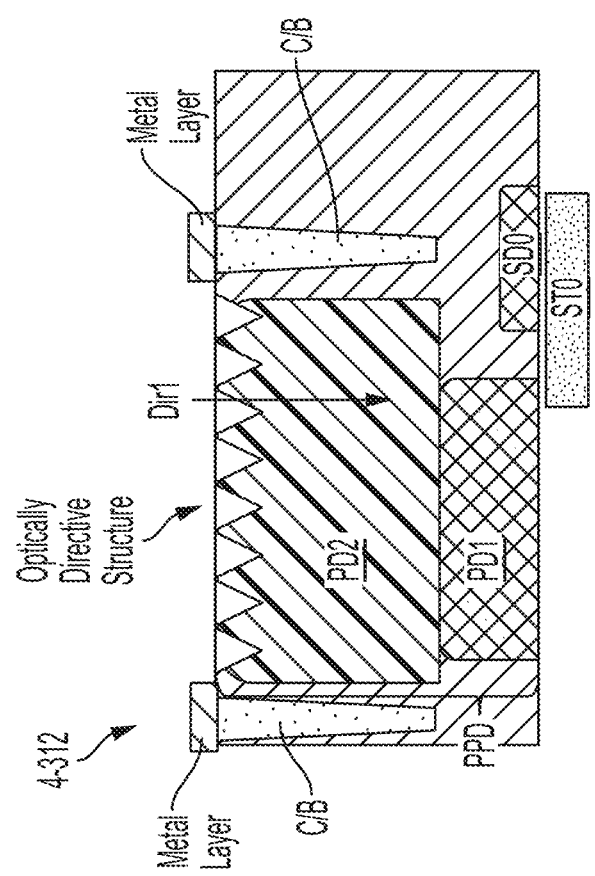

According to some embodiments, an advanced analytic instrument 5-100 that is configured to analyze samples based on fluorescent emission characteristics can detect differences in fluorescent lifetimes and/or intensities between different fluorescent molecules, and/or differences between lifetimes and/or intensities of the same fluorescent molecules in different environments. By way of explanation, FIG. 5-7 plots two different fluorescent emission probability curves (A and B), which can be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time can be represented by an exponential decay function $p_A(t)=P_{Ao}*e^{(-t/\tau_1)}$, where $P_{Ao}$ is an initial emission probability and $\tau_1$ is a temporal parameter associated with the first fluorescent molecule that characterizes the emission decay probability. $\tau_1$ may be referred to as the "fluorescence lifetime," "emission lifetime," or "lifetime" of the first fluorescent molecule. In some cases, the value of $\tau_1$ can be altered by a local environment of the fluorescent molecule. Other fluorescent molecules can have different emission characteristics than that shown in curve A. For example, another fluorescent molecule can have a decay profile that differs from a single exponential decay, and its lifetime can be characterized by a half-life value or some other metric.

A second fluorescent molecule may have a decay profile $p_B(t)$ that is exponential, but has a measurably different lifetime $\tau_2$, as depicted for curve B in FIG. 5-7. The initial emission probability for curve B is shown in FIG. 5-7 as $P_{Bo}$. In the example shown, the lifetime for the second fluorescent molecule of curve B is shorter than the lifetime for curve A, and the probability of emission $p_B(t)$ is higher sooner after excitation of the second molecule than for curve A. Different fluorescent molecules can have lifetimes or half-life values ranging from about 0.1 ns to about 20 ns, in some embodiments.

Differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of an analytical instrument 5-100. As an example, wavelength-discriminating optics (such as wavelength filters, dedicated detectors for each wavelength, dedicated pulsed optical sources at different wavelengths, and/or diffractive optics) can be reduced in number or eliminated when discerning fluorescent molecules based on lifetime. In some cases, a single pulsed optical source operating at a single characteristic wavelength can be used to excite different fluorescent molecules that emit within a same wavelength region of the optical spectrum but have measurably different lifetimes. An analytic system that uses a single pulsed optical source, rather than multiple sources operating at different wavelengths, to excite and discern different fluorescent molecules emitting in a same wavelength region can be less complex to operate and maintain, more compact, and can be manufactured at lower cost.

Although analytic systems based on fluorescent lifetime analysis can have certain benefits, the amount of information obtained by an analytic system and/or detection accuracy can be increased by allowing for additional detection techniques. For example, some analytic systems 5-160 can additionally be configured to discern one or more properties of a sample based on fluorescent wavelength and/or fluorescent intensity.

Referring again to FIG. 5-7, according to some embodiments, different fluorescent lifetimes can be distinguished with a photodetector that is configured to time-bin fluorescent emission events following excitation of a fluorescent molecule. The time binning can occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 5-8. At time te just prior to $t_1$, a fluorescent molecule or ensemble of fluorescent molecules of a same type (e.g., the type corresponding to curve B of FIG. 5-7) is (are) excited by a short or ultrashort optical pulse. For a large ensemble of molecules, the intensity of emission can have a time profile similar to curve B, as depicted in FIG. 5-8.

For a single molecule or a small number of molecules, however, the emission of fluorescent photons occurs according to the statistics of curve B in FIG. 5-7, for this example. A time-binning photodetector 5-322 can accumulate carriers generated from emission events into discrete time bins. Three bins are indicated in FIG. 5-8, though fewer bins or more bins may be used in embodiments. The bins are temporally resolved with respect to the excitation time te of the fluorescent molecule(s). For example, a first bin can accumulate carriers produced during an interval between times $t_1$ and $t_2$, occurring after the excitation event at time $t_e$. A second bin can accumulate carriers produced during an interval between times $t_2$ and $t_3$, and a third bin can accumulate carriers produced during an interval between times $t_3$ and $t_4$. When a large number of emission events are summed, carriers accumulated in the time bins can approximate the decaying intensity curve shown in FIG. 5-8, and the binned signals can be used to distinguish between different fluorescent molecules or different environments in which a fluorescent molecule is located.

Examples of a time-binning photodetector 5-322 are described in U.S. patent application Ser. No. 14/821,656, filed Aug. 7, 2015, titled "Integrated Device for Temporal Binning of Received Photons" and in U.S. patent application Ser. No. 15/852,571, filed Dec. 22, 2017, titled "Integrated Photodetector with Direct Binning Pixel," which are both incorporated herein by reference in their entirety. For explanation purposes, a non-limiting embodiment of a time-binning photodetector is depicted in FIG. 5-9. A single time-binning photodetector 5-322 can comprise a photon-absorption/carrier-generation region 5-902, a carrier-discharge channel 5-906, and a plurality of carrier-storage regions 5-908a, 5-908b all formed on a semiconductor substrate. Carrier-transport channels 5-907 can connect between the photon-absorption/carrier-generation region 5-902 and carrier-storage regions 5-908a, 5-908b. In the illustrated example, two carrier-storage regions are shown, but there may be more or fewer. There can be a read-out channel 5-910 connected to the carrier-storage regions. The photon-absorption/carrier-generation region 5-902, carrier-discharge channel 5-906, carrier-storage regions 5-908a, 5-908b, and read-out channel 5-910 can be formed by doping the semiconductor locally and/or forming adjacent insulating regions to provide photodetection capability, confinement, and transport of carriers. A time-binning photodetector 5-322 can also include a plurality of electrodes 5-920, 5-921, 5-922, 5-923, 5-924 formed on the substrate that are configured to generate electric fields in the device for transporting carriers through the device. Other examples of suitable photodetectors are described herein, including with a single charge storage region and with multiple sequentially-coupled charge storage regions, but embodiments described herein are not so limited.

In operation, a portion of an excitation pulse 5-122 from a pulsed optical source 5-106 (e.g., a mode-locked laser) is delivered to a reaction chamber 5-330 over the time-binning photodetector 5-322. Initially, some excitation radiation photons 5-901 may arrive at the photon-absorption/carrier-generation region 5-902 and produce carriers (shown as light-shaded circles). There can also be some fluorescent emission photons 5-903 that arrive with the excitation radiation photons 5-901 and produce corresponding carriers (shown as dark-shaded circles). Initially, the number of carriers produced by the excitation radiation can be too large compared to the number of carriers produced by the fluorescent emission. The initial carriers produced during a time interval $t_e$-$t_1$ can be rejected by gating them into a carrier-discharge channel 5-906 with a first transfer gate 5-920, for example.

At a later times mostly fluorescent emission photons 5-903 arrive at the photon-absorption/carrier-generation region 5-902 and produce carriers (indicated a dark-shaded circles) that provide useful and detectable signal that is representative of fluorescent emission from the reaction chamber 5-330. According to some detection methods, a second electrode 5-921 and third electrode 5-923 can be gated at a later time to direct carriers produced at a later time (e.g., during a second time interval $t_1$-$t_2$) to a first carrier-storage region 5-908a. Subsequently, a fourth electrode 5-922 and fifth electrode 5-924 can be gated at a later time (e.g., during a third time interval $t_2$-$t_3$) to direct carriers to a second carrier-storage region 5-908b. Charge accumulation can continue in this manner after excitation pulses for a large number of excitation pulses to accumulate an appreciable number of carriers and signal level in each carrier-storage region 5-908a, 5-908b. At a later time, the signal can be read out from the bins. In some implementations, the time intervals corresponding to each storage region are at the sub-nanosecond time scale, though longer time scales can be used in some embodiments (e.g., in embodiments where fluorophores have longer decay times).

The process of generating and time-binning carriers after an excitation event (e.g., excitation pulse from a pulsed optical source) can occur once after a single excitation pulse or be repeated multiple times after multiple excitation pulses during a single charge-accumulation cycle for the time-binning photodetector 5-322. After charge accumulation is complete, carriers can be read out of the storage regions via the read-out channel 5-910. For example, an appropriate biasing sequence can be applied to electrodes 5-923, 5-924 and at least to electrode 5-940 to remove carriers from the storage regions 5-908a, 5-908b. The charge accumulation and read-out processes can occur in a massively parallel operation on the optoelectronic chip 5-140 resulting in frames of data.

Although the described example in connection with FIG. 5-9 includes multiple charge storage regions 5-908a, 5-908b in some cases a single charge storage region may be used instead. For example, only bin1 may be present in a time-binning photodetector 5-322. In such a case, a single storage regions 5-908a can be operated in a variable time-gated manner to look at different time intervals after different excitation events. For example, after pulses in a first series of excitation pulses, electrodes for the storage region 5-908a can be gated to collect carriers generated during a first time interval (e.g., during the second time interval $t_1$-$t_2$), and the accumulated signal can be read out after a first predetermined number of pulses. After pulses in a subsequent series of excitation pulses at the same reaction chamber, the same electrodes for the storage region 5-908a can be gated to collect carriers generated during a different interval (e.g., during the third time interval $t_2$-$t_3$), and the accumulated signal can be read out after a second predetermined number of pulses. Carriers could be collected during later time intervals in a similar manner if needed. In this manner, signal levels corresponding to fluorescent emission during different time periods after arrival of an excitation pulse at a reaction chamber can be produced using a single carrier-storage region.

In some embodiments, carriers produced during the second and third time intervals may be collected and stored using sequentially-coupled charge-carrier storage regions. For example, charge carriers produced during the time interval $t_1$-$t_2$ may be collected in a first charge storage region and transferred to a second charge storage region, and then charge carriers produced during the time interval $t_2$-$t_3$ may be collected in the first charge storage region while the charge carriers collected during time interval $t_1$-$t_2$ are read out to readout region FD. Alternatively or additionally, the charge carriers produced during time interval $t_1$-$t_2$ can be further transferred to and read out from a third charge storage region, and then the charge carriers produced during time interval $t_2$-$t_3$ can be read out from the second charge storage region via the third charge storage region (e.g., without resetting the voltage of readout region FD in between).

Regardless of how charge accumulation is carried out for different time intervals after excitation, signals that are read out can provide a histogram of bins that are representative of the fluorescent emission decay characteristics, for example. An example process is illustrated in FIG. 5-10A and FIG. 5-10B, for which two charge-storage regions are used to acquire fluorescent emission from the reaction chambers. The histogram's bins can indicate a number of photons detected during each time interval after excitation of the fluorophore(s) in a reaction chamber 5-330. In some embodiments, signals for the bins will be accumulated following a large number of excitation pulses, as depicted in FIG. 5-10A. The excitation pulses can occur at times $t_{e1}$, $t_{e2}$, $t_{e3}$, ... teN which are separated by the pulse interval time T. In some cases, there can be between 105 and 107 excitation pulses 5-122 (or portions thereof) applied to a reaction chamber during an accumulation of signals in the electron-storage regions for a single event being observed in the reaction chamber (e.g., a single nucleotide incorporation event in DNA analysis). In some embodiments, one bin (bin 0) can be configured to detect an amplitude of excitation energy delivered with each optical pulse, and may be used as a reference signal (e.g., to normalize data). In other cases, the excitation pulse amplitude may be stable, determined one or more times during signal acquisition, and not determined after each excitation pulse so that there is no bin( ) signal acquisition after each excitation pulse. In such cases, carriers produced by an excitation pulse can be rejected and dumped from the photon-absorption/carrier-generation region 5-902 as described above in connection with FIG. 5-9.

In some implementations, only a single photon may be emitted from a fluorophore following an excitation event, as depicted in FIG. 5-10A. After a first excitation event at time $t_{e1}$, the emitted photon at time $t_{f1}$ may occur within a first time interval (e.g., between times $t_1$ and $t_2$), so that the resulting electron signal is accumulated in the first electron-storage region (contributes to bin 1). In a subsequent excitation event at time $t_{e2}$, the emitted photon at time $t_{f2}$ may occur within a second time interval (e.g., between times $t_2$ and $t_3$), so that the resulting electron signal contributes to bin 2. After a next excitation event at time tea, a photon may emit at a time $t_{f3}$ occurring within the first time interval.

In some implementations, there may not be a fluorescent photon emitted and/or detected after each excitation pulse received at a reaction chamber 5-330. In some cases, there can be as few as one fluorescent photon that is detected at a reaction chamber for every 10,000 excitation pulses delivered to the reaction chamber. One advantage of implementing a mode-locked laser 5-113 as the pulsed excitation source 5-106 is that a mode-locked laser can produce short optical pulses having high intensity and quick turn-off times at high pulse-repetition rates (e.g., between 50 MHz and 250 MHz). With such high pulse-repetition rates, the number of excitation pulses within a 10 millisecond charge-accumulation interval can be 50,000 to 250,000, so that detectable signal can be accumulated.

After a large number of excitation events and carrier accumulations, the carrier-storage regions of the time-binning photodetector 5-322 can be read out to provide a multi-valued signal (e.g., a histogram of two or more values, an N-dimensional vector, etc.) for a reaction chamber. The signal values for each bin can depend upon the decay rate of the fluorophore. For example and referring again to FIG. 5-8, a fluorophore having a decay curve B will have a higher ratio of signal in bin 1 to bin 2 than a fluorophore having a decay curve A. The values from the bins can be analyzed and compared against calibration values, and/or each other, to determine the particular fluorophore present. For a sequencing application, identifying the fluorophore can determine the nucleotide or nucleotide analog that is being incorporated into a growing strand of DNA, for example. For other applications, identifying the fluorophore can determine an identity of a molecule or specimen of interest, which may be linked to the fluorophore.

To further aid in understanding the signal analysis, the accumulated, multi-bin values can be plotted as a histogram, as depicted in FIG. 5-10B for example, or can be recorded as a vector or location in N-dimensional space. Calibration runs can be performed separately to acquire calibration values for the multi-valued signals (e.g., calibration histograms) for four different fluorophores linked to the four nucleotides or nucleotide analogs. As an example, the calibration histograms may appear as depicted in FIG. 5-11A (fluorescent label associated with the T nucleotide), FIG. 5-11B (fluorescent label associated with the A nucleotide), FIG. 5-11C (fluorescent label associated with the C nucleotide), and FIG. 5-11D (fluorescent label associated with the G nucleotide). A comparison of the measured multi-valued signal (corresponding to the histogram of FIG. 5-10B) to the calibration multi-valued signals can determine the identity "T" (FIG. 5-11A) of the nucleotide or nucleotide analog being incorporated into the growing strand of DNA.

In some implementations, fluorescent intensity can be used additionally or alternatively to distinguish between different fluorophores. For example, some fluorophores may emit at significantly different intensities or have a significant difference in their probabilities of excitation (e.g., at least a difference of about 35%) even though their decay rates may be similar. By referencing binned signals (bins 5-3) to measured excitation energy and/or other acquired signals, it can be possible to distinguish different fluorophores based on intensity levels.

In some embodiments, different numbers of fluorophores of the same type can be linked to different nucleotides or nucleotide analogs, so that the nucleotides can be identified based on fluorophore intensity. For example, two fluorophores can be linked to a first nucleotide (e.g., "C") or nucleotide analog and four or more fluorophores can be linked to a second nucleotide (e.g., "T") or nucleotide analog. Because of the different numbers of fluorophores, there may be different excitation and fluorophore emission probabilities associated with the different nucleotides. For example, there may be more emission events for the "T" nucleotide or nucleotide analog during a signal accumulation interval, so that the apparent intensity of the bins is significantly higher than for the "C" nucleotide or nucleotide analog.

Distinguishing nucleotides or any other biological or chemical specimens based on fluorophore decay rates and/or fluorophore intensities enables a simplification of the optical excitation and detection systems in an analytical instrument 5-100. For example, optical excitation can be performed with a single-wavelength source (e.g., a source producing one characteristic wavelength rather than multiple sources or a source operating at multiple different characteristic wavelengths). Additionally, wavelength-discriminating optics and filters may not be needed in the detection system to distinguish between fluorophores of different wavelengths. Also, a single photodetector can be used for each reaction chamber to detect emission from different fluorophores.

The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

Fluorophores having emission wavelengths in a range between about 560 nm and about 900 nm can provide adequate amounts of fluorescence to be detected by a time-binning photodetector (which can be fabricated on a silicon wafer using CMOS processes). These fluorophores can be linked to biological molecules of interest, such as nucleotides or nucleotide analogs for genetic sequencing applications. Fluorescent emission in this wavelength range can be detected with higher responsivity in a silicon-based photodetector than fluorescence at longer wavelengths. Additionally, fluorophores and associated linkers in this wavelength range may not interfere with incorporation of the nucleotides or nucleotide analogs into growing strands of DNA. In some implementations, fluorophores having emission wavelengths in a range between about 560 nm and about 660 nm can be optically excited with a single-wavelength source. An example fluorophore in this range is Alexa Fluor 647, available from Thermo Fisher Scientific Inc. of Waltham, Massachusetts. Excitation energy at shorter wavelengths (e.g., between about 500 nm and about 650 nm) may be used to excite fluorophores that emit at wavelengths between about 560 nm and about 900 nm. In some embodiments, the time-binning photodetectors can efficiently detect longer-wavelength emission from the reaction chambers, e.g., by incorporating other materials, such as Ge, into the photodetectors' active regions.

VIII. Protein Sequencing Applications

Some aspects of the present disclosure may be useful for protein sequencing. For example, some aspects of the present disclosure are useful for determining amino acid sequence information from polypeptides (e.g., for sequencing one or more polypeptides). In some embodiments, amino acid sequence information can be determined for single polypeptide molecules. In some embodiments, one or more amino acids of a polypeptide are labeled (e.g., directly or indirectly) and the relative positions of the labeled amino acids in the polypeptide are determined. In some embodiments, the relative positions of amino acids in a protein are determined using a series of amino acid labeling and cleavage steps.

In some embodiments, the identity of a terminal amino acid (e.g., an N-terminal or a C-terminal amino acid) is assessed, after which the terminal amino acid is removed and the identity of the next amino acid at the terminus is assessed, and this process is repeated until a plurality of successive amino acids in the polypeptide are assessed. In some embodiments, assessing the identity of an amino acid comprises determining the type of amino acid that is present. In some embodiments, determining the type of amino acid comprises determining the actual amino acid identity, for example by determining which of the naturally-occurring 20 amino acids is the terminal amino acid (e.g., using a recognition molecule that is specific for an individual terminal amino acid). However, in some embodiments assessing the identity of a terminal amino acid type can comprise determining a subset of potential amino acids that can be present at the terminus of the polypeptide. In some embodiments, this can be accomplished by determining that an amino acid is not one or more specific amino acids (and therefore could be any of the other amino acids). In some embodiments, this can be accomplished by determining which of a specified subset of amino acids (e.g., based on size, charge, hydrophobicity, binding properties) could be at the terminus of the polypeptide (e.g., using a recognition molecule that binds to a specified subset of two or more terminal amino acids).

Amino acids of a polypeptide can be indirectly labeled, for example, using amino acid recognition molecules that selectively bind one or more types of amino acids on the polypeptide. Amino acids of a polypeptide can be directly labeled, for example, by selectively modifying one or more types of amino acid side chains on the polypeptide with uniquely identifiable labels. Methods of selective labeling of amino acid side chains and details relating to the preparation and analysis of labeled polypeptides are known in the art (see, e.g., Swaminathan, et al. PLoS Comput Biol. 2015, 11(2):e 1004080). Accordingly, in some embodiments, the one or more types of amino acids are identified by detecting binding of one or more amino acid recognition molecules that selectively bind the one or more types of amino acids. In some embodiments, the one or more types of amino acids are identified by detecting labeled polypeptide.

In some embodiments, the relative position of labeled amino acids in a protein can be determined without removing amino acids from the protein but by translocating a labeled protein through a pore (e.g., a protein channel) and detecting a signal (e.g., a Förster resonance energy transfer (FRET) signal) from the labeled amino acid(s) during translocation through the pore in order to determine the relative position of the labeled amino acids in the protein molecule.

As used herein, sequencing a polypeptide refers to determining sequence information for a polypeptide. In some embodiments, this can involve determining the identity of each sequential amino acid for a portion (or all) of the polypeptide. However, in some embodiments, this can involve assessing the identity of a subset of amino acids within the polypeptide (e.g., and determining the relative position of one or more amino acid types without determining the identity of each amino acid in the polypeptide). However, in some embodiments amino acid content information can be obtained from a polypeptide without directly determining the relative position of different types of amino acids in the polypeptide. The amino acid content alone may be used to infer the identity of the polypeptide that is present (e.g., by comparing the amino acid content to a database of polypeptide information and determining which polypeptide (s) have the same amino acid content).

In some embodiments, sequence information for a plurality of polypeptide products obtained from a longer polypeptide or protein (e.g., via enzymatic and/or chemical cleavage) can be analyzed to reconstruct or infer the sequence of the longer polypeptide or protein. Accordingly, some embodiments provide compositions and methods for sequencing a polypeptide by sequencing a plurality of fragments of the polypeptide. In some embodiments, sequencing a polypeptide comprises combining sequence information for a plurality of polypeptide fragments to identify and/or determine a sequence for the polypeptide. In some embodiments, combining sequence information may be performed by computer hardware and software. The methods described herein may allow for a set of related polypeptides, such as an entire proteome of an organism, to be sequenced. In some embodiments, a plurality of single molecule sequencing reactions may be performed in parallel (e.g., on a single chip). For example, in some embodiments, a plurality of single molecule sequencing reactions are each performed in separate sample wells on a single chip.

In some embodiments, methods provided herein may be used for the sequencing and identification of an individual protein in a sample comprising a complex mixture of proteins. Some embodiments provide methods of uniquely identifying an individual protein in a complex mixture of proteins. In some embodiments, an individual protein is detected in a mixed sample by determining a partial amino acid sequence of the protein. In some embodiments, the partial amino acid sequence of the protein is within a contiguous stretch of approximately 5 to 50 amino acids.

Without wishing to be bound by any particular theory, it is believed that most human proteins can be identified using incomplete sequence information with reference to proteomic databases. For example, simple modeling of the human proteome has shown that approximately 98% of proteins can be uniquely identified by detecting just four types of amino acids within a stretch of 6 to 40 amino acids (see, e.g., Swaminathan, et al. PLoS Comput Biol. 2015, 11(2):e 1004080; and Yao, et al. Phys. Biol. 2015, 12(5): 055003). Therefore, a complex mixture of proteins can be degraded (e.g., chemically degraded, enzymatically degraded) into short polypeptide fragments of approximately 6 to 40 amino acids, and sequencing of this polypeptide library would reveal the identity and abundance of each of the proteins present in the original complex mixture. Compositions and methods for selective amino acid labeling and identifying polypeptides by determining partial sequence information are described in in detail in U.S. patent application Ser. No. 15/510,962, filed Sep. 15, 2015, titled "SINGLE MOLECULE PEPTIDE SEQUENCING," which is incorporated by reference in its entirety.

Sequencing in accordance with some embodiments can involve immobilizing a polypeptide on a surface of a substrate or solid support, such as a chip or integrated device. In some embodiments, a polypeptide can be immobilized on a surface of a sample well (e.g., on a bottom surface of a sample well) on a substrate. In some embodiments, a first terminus of a polypeptide is immobilized to a surface, and the other terminus is subjected to a sequencing reaction as described herein. For example, in some embodiments, a polypeptide is immobilized to a surface through a C-terminal end, and terminal amino acid recognition and degradation proceeds from an N-terminal end of the polypeptide toward the C-terminal end. In some embodiments, the N-terminal amino acid of the polypeptide is immobilized (e.g., attached to the surface). In some embodiments, the C-terminal amino acid of the polypeptide is immobilized (e.g., attached to the surface). In some embodiments, one or more non-terminal amino acids are immobilized (e.g., attached to the surface). The immobilized amino acid(s) can be attached using any suitable covalent or non-covalent linkage, for example as described herein. In some embodiments, a plurality of polypeptides are attached to a plurality of sample wells (e.g., with one polypeptide attached to a surface, for example a bottom surface, of each sample well), for example in an array of sample wells on a substrate.

Some aspects of the present disclosure provide a method of sequencing a polypeptide by detecting luminescence of a labeled polypeptide which is subjected to repeated cycles of terminal amino acid modification and cleavage. For example, FIG. 5-12 shows a method of sequencing a labeled polypeptide by Edman degradation in accordance with some embodiments. In some embodiments, the method generally proceeds as described herein for other methods of sequencing by Edman degradation. For example, in some embodiments, steps (1) and (2) shown in FIG. 5-12 may be performed as described elsewhere herein for terminal amino acid modification and terminal amino acid cleavage, respectively, in an Edman degradation reaction.

As shown in the example depicted in FIG. 5-12, in some embodiments, the method comprises a step of (1) modifying the terminal amino acid of a labeled polypeptide. As described elsewhere herein, in some embodiments, modifying comprises contacting the terminal amino acid with an isothiocyanate (e.g., PITC) to form an isothiocyanate-modified terminal amino acid. In some embodiments, an isothiocyanate modification 5-1210 converts the terminal amino acid to a form that is more susceptible to removal by a cleaving reagent (e.g., a chemical or enzymatic cleaving reagent, as described herein). Accordingly, in some embodiments, the method comprises a step of (2) removing the modified terminal amino acid using chemical or enzymatic means detailed elsewhere herein for Edman degradation.

In some embodiments, the method comprises repeating steps (1) through (2) for a plurality of cycles, during which luminescence of the labeled polypeptide is detected, and cleavage events corresponding to the removal of a labeled amino acid from the terminus may be detected as a decrease in detected signal. In some embodiments, no change in signal following step (2) as shown in FIG. 5-12 identifies an amino acid of unknown type. Accordingly, in some embodiments, partial sequence information may be determined by evaluating a signal detected following step (2) during each sequential round by assigning an amino acid type by a determined identity based on a change in detected signal or identifying an amino acid type as unknown based on no change in a detected signal.

Some aspects of the present disclosure provide methods of polypeptide sequencing in real-time by evaluating binding interactions of terminal amino acids with labeled amino acid recognition molecules and a labeled cleaving reagent (e.g., a labeled exopeptidase). FIG. 5-13 shows an example of a method of sequencing in which discrete binding events give rise to signal pulses of a signal output 5-1300. The inset panel of FIG. 5-13 illustrates a general scheme of real-time sequencing by this approach. As shown, a labeled amino acid recognition molecule 5-1310 selectively binds to and dissociates from a terminal amino acid (shown here as lysine), which gives rise to a series of pulses in signal output 5-1300 which may be used to identify the terminal amino acid. In some embodiments, the series of pulses provide a pulsing pattern which may be diagnostic of the identity of the corresponding terminal amino acid.

Without wishing to be bound by theory, labeled amino acid recognition molecule 5-1310 selectively binds according to a binding affinity (KD) defined by an association rate of binding (kon) and a dissociation rate of binding (koff). The rate constants koff and kon are the critical determinants of pulse duration (e.g., the time corresponding to a detectable binding event) and interpulse duration (e.g., the time between detectable binding events), respectively. In some embodiments, these rates can be engineered to achieve pulse durations and pulse rates that give the best sequencing accuracy.

As shown in the inset panel, a sequencing reaction mixture further comprises a labeled cleaving reagent 5-1320 comprising a detectable label that is different than that of labeled amino acid recognition molecule 5-1310. In some embodiments, labeled cleaving reagent 5-1320 is present in the mixture at a concentration that is less than that of labeled amino acid recognition molecule 5-1310. In some embodiments, labeled cleaving reagent 5-1320 displays broad specificity such that it cleaves most or all types of terminal amino acids.

As illustrated by the progress of signal output 5-1300, in some embodiments, terminal amino acid cleavage by labeled cleaving reagent 5-1320 gives rise to a uniquely identifiable signal pulse, and these events occur with lower frequency than the binding pulses of a labeled amino acid recognition molecule 5-1310. In this way, amino acids of a polypeptide can be counted and/or identified in a real-time sequencing process. As further illustrated in signal output 5-1300, in some embodiments, a labeled amino acid recognition molecule 5-1310 is engineered to bind more than one type of amino acid with different binding properties corresponding to each type, which produces uniquely identifiable pulsing patterns. In some embodiments, a plurality of labeled amino acid recognition molecules may be used, each with a diagnostic pulsing pattern which may be used to identify a corresponding terminal amino acid.

IX. Conclusion

Having thus described several aspects and embodiments of the technology of the present disclosure, it is to be appreciated that various alterations, modifications, and improvements will readily occur to those of ordinary skill in the art. Such alterations, modifications, and improvements are intended to be within the spirit and scope of the technology described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. An integrated circuit, comprising:
a photodetection region configured to:
receive, proximate a first surface of the integrated circuit, in a first direction, incident photons; and
generate, in response to receiving the incident photons, charge carriers;

one or more charge storage regions proximate a second surface opposite the first surface in the first direction and configured to receive the charge carriers from the photodetection region; and one or more charged and/or biased regions configured to induce a charge carrier depletion in the photodetection region for propagating the charge carriers, at least partially in the first direction, from the photodetection region toward the one or more charge storage regions, wherein the one or more charged and/or biased regions are elongated from the first surface in the first direction alongside the photodetection region.

2. The integrated circuit of claim 1, wherein the one or more charged and/or biased regions comprise a charge layer comprising a metal-oxide compound that induces the charge carrier depletion in the photodetection region.

3. The integrated circuit of claim 1, wherein the one or more charged and/or biased regions comprise one or more metal regions configured to, when the integrated circuit is electrically coupled to a power supply, receive, from the power supply, a voltage bias that induces the charge carrier depletion in the photodetection region.

4. The integrated circuit of claim 1, wherein the one or more charged and/or biased regions comprise:
 a first charged and/or biased region positioned on a first side of the photodetection region; and
 a second charged and/or biased region positioned on a second side of the photodetection region opposite the first side in a second direction perpendicular to the first direction.

5. The integrated circuit of claim 1, further comprising one or more transfer gates configured to control transfer of charge carriers between the photodetection region and the one or more charge storage regions and/or between the one or more charge storage regions and a readout region, wherein the one or more transfer gates are positioned, in the first direction, after the photodetection region and the one or more charge storage regions.

6. The integrated circuit of claim 1, further comprising one or more doped barriers positioned around the one or more charged and/or biased regions.

7. The integrated circuit of claim 1, further comprising a metal shield positioned, in the first direction, before the one or more charged and/or biased regions and comprising an opening aligned, in the first direction, with lateral ends of the photodetection region, the lateral ends separated from one another in a direction perpendicular to the first direction.

8. The integrated circuit of claim 1, wherein the one or more charged and/or biased regions are elongated, in the first direction, alongside substantially an entire depth, in the first direction, of the photodetection region.

9. A method, comprising:
 inducing in a photodetection region of an integrated circuit, using one or more charged and/or biased regions, a charge carrier depletion;
 receiving, proximate a first surface of the integrated circuit, in a first direction, incident photons at the photodetection region, wherein the one or more charged and/or biased regions are elongated from the first surface in the first direction alongside the photodetection region;
 generating, in the photodetection region in response to the incident photons, charge carriers;
 propagating, at least partially in the first direction, from the photodetection region toward one or more charge storage regions proximate a second surface opposite the first surface in the first direction, the charge carriers; and
 receiving, at the one or more charge storage regions of the integrated circuit, the charge carriers from the photodetection region.

10. The method of claim 9, wherein the charge carrier depletion is induced, at least in part, by one or more charged regions of the integrated circuit that comprise a charge layer having a metal-oxide compound.

11. The method of claim 9, wherein the charge carrier depletion is induced, at least in part, by one or more metal regions that receive a voltage bias to induce the charge carrier depletion in the photodetection region.

12. The method of claim 9, wherein the charge carrier depletion is induced from alongside the photodetection region in the first direction on at least a first side of the photodetection region and a second side of the photodetection region opposite the first side in a second direction perpendicular to the first direction.

13. The method of claim 9, further comprising controlling transfer of charge carriers between the photodetection region and the one or more charge storage regions and/or between the one or more charge storage regions and a readout region using one or more transfer gates that are positioned, in the first direction, after the photodetection region and the one or more charge storage regions.

14. The method of claim 9, further comprising receiving, at the photodetection region, the incident photons through an opening of a metal shield aligned, in the first direction, with lateral ends of the photodetection region, the lateral ends separated from one another in a second direction perpendicular to the first direction.

15. An integrated circuit, comprising:
 a first pixel comprising a first photodetection region configured to receive photons in a first direction;
 a second pixel comprising a second photodetection region configured to receive photons in the first direction; and
 one or more charged and/or biased regions positioned between the first photodetection region and the second photodetection region, wherein the one or more charged and/or biased regions are elongated in the first direction alongside the first photodetection region and the second photodetection region, and wherein the one or more charged and/or biased regions comprises a charge layer and/or one or more metal regions elongated in the first direction alongside the first photodetection region and the second photodetection region.

16. The integrated circuit of claim 15, wherein:
 the first pixel further comprises one or more charge storage regions configured to receive charge carriers generated in the first photodetection region in response to photons received, in the first direction, at the first photodetection region; and
 the second pixel further comprises one or more charge storage regions configured to receive charge carriers generated in the second photodetection region in response to the second photodetection region receiving photons in the first direction.

17. The integrated circuit of claim 15, wherein the one or more charged and/or biased regions are alongside the first photodetection region on at least a first side of the first photodetection region and a second side of the first photodetection region opposite the first side in a second direction perpendicular to the first direction.

18. The integrated circuit of claim 15, wherein the charge layer comprises a metal-oxide compound configured to induce charge carrier depletion in the first photodetection region.

19. The integrated circuit of claim 15, wherein the one or more metal regions are configured to, when the integrated circuit is electrically coupled to a power supply, receive, from the power supply, a voltage bias that induces charge carrier depletion in the first photodetection region.

20. The integrated circuit of claim 15, further comprising:
one or more charge storage regions and/or a readout region; and
one or more transfer gates configured to control transfer of charge carriers between the first photodetection region and the one or more charge storage regions and/or between the one or more charge storage regions and the readout region, wherein the one or more transfer gates are positioned, in the first direction, after the first photodetection region and the one or more charge storage regions and/or after the first photodetection region and the readout region.

21. The integrated circuit of claim 20, further comprising a metal shield positioned, in the first direction, before the one or more charged and/or biased regions and comprising an opening aligned, in the first direction, with lateral ends of the first photodetection region, the lateral ends separated from one another in a direction perpendicular to the first direction.

* * * * *